(12) United States Patent
Fukuda et al.

(10) Patent No.: US 7,291,491 B2
(45) Date of Patent: Nov. 6, 2007

(54) POLYPEPTIDES

(75) Inventors: Minoru Fukuda, San Diego, CA (US);
Katsutoshi Sasaki, Sagamihara (JP);
Kazumi Miura, Fujisawa (JP); Satoshi Nakagawa, Machida (JP); Tatsunari Nishi, Ohta-ku (JP); Susumu Sekine, Yokohama (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 696 days.

(21) Appl. No.: 10/166,098

(22) Filed: Jun. 11, 2002

(65) Prior Publication Data

US 2003/0166208 A1    Sep. 4, 2003

Related U.S. Application Data

(62) Division of application No. 09/182,450, filed on Oct. 30, 1998, now Pat. No. 6,420,149.

(30) Foreign Application Priority Data

Oct. 31, 1997    (JP) .................................. 9-300715

(51) Int. Cl.
*C12N 9/10* (2006.01)
*C07H 21/04* (2006.01)
*C12P 21/06* (2006.01)

(52) U.S. Cl. .............................. 435/193; 435/4; 435/6; 435/69.1; 435/183; 435/252.3; 435/320.1; 435/325; 536/23.2; 536/23.4; 536/23.5; 536/23.7

(58) Field of Classification Search .................... 435/4, 435/6, 69.1, 183, 193, 252.3, 320.1, 325; 536/23.2, 23.5
See application file for complete search history.

(56) References Cited

U.S. PATENT DOCUMENTS 6,222,029 B1 *    4/2001    Edwards et al. ........... 536/24.1

OTHER PUBLICATIONS

Edwards et al. US, 6,222,029, Sequence alignment.*
GenBank Accession No. AAQ61365, 1994, Venter et al.*
Kawashima, et al., "Purification and Characterization of UDP-GlcNAc:Galβ1-4Glc(NAc) . . . ", The Journal of Biological Chemistry, vol. 268, No. 36 (1993), pp. 27118-27126.
Hosomi, et al., "Human Serum Contains N-Acetyllactosamine: . . . ", J. Biochem., vol. 95 (1984), pp. 1655-1659.
Holmes, "Characterization of a β1→3-N-Acetylglucosaminyltransferase Associated with . . . ", Archives of Biochemistry and Biophysics, vol. 260, No. 1 (1988), pp. 461-468.
Kukowska-Latallo, et al., "A Cloned Human cDNA determines expression of a mouse stage-specific . . . ", Genes & Development (1990), pp. 1288-1303.
Lowe, et al., "Molecular Cloning of a Human Fucosyltransferase Gene . . . ", The Journal of Biological Chemistry, vol. 266, No. 26 (1991), pp. 17467-17477.
Weston, et al., "Isolation of a Novel Human α(1,3)Fucosyltransferase Gene and . . . ", The Journal of Biological Chemistry, vol. 267, No. 6 (1992), pp. 4152-4160.
Weston, et al., "Molecular Cloning of a Fourth Member of a Human . . . ", The Journal of Biological Chemistry, vol. 267, No. 34 (1992), pp. 24575-24584.
Sasaki, et al., "Expression Cloning of a Novel α-1,3-Fucosyltransferase That Is . . . ", The Journal of Biological Chemistry, vol. 269, No. 20 (1994), pp. 14730-14737.
Kudo, et al., "Expression Cloning and Characterization of a Novel Murine . . . ", The Journal of Biological Chemistry, vol. 273, No. 41 (1998), pp. 26729-26738.
Zhou, et al., "A β-1,3-N-acetylglucosaminyltransferase with . . . ", Proc. Natl. Acad. Sci., vol. 96 (1999), pp. 406-411.
Sasaki, et al., "Expression cloning of cDNA encoding a human . . . ", Proc. Natl. Acad. Sci., vol. 94 (1997), pp. 14294-14299.

* cited by examiner

*Primary Examiner*—Manjunath Rao
(74) *Attorney, Agent, or Firm*—Fitzpatrick, Cella, Harper & Scinto

(57) ABSTRACT

The present invention provides pharmaceutical preparations for anti-inflammation, anti-infection, inhibition of cancer metastasis etc., foods such as dairy products etc., and a method for improving proteins, as well as a method for diagnosis of inflammatory diseases and cancer malignancy. According to the present invention, there can be provided a polypeptide having poly-N-acetyllactosamine sugar chains synthesis-related activity, a process for producing the polypeptide, DNA coding for the polypeptide, a process for producing the DNA, a recombinant vector having the DNA integrated therein, a transformant carrying the recombinant vector, an antibody recognizing the polypeptide, a process for producing poly-N-acetyllactosamine sugar chains by use of the DNA or the polypeptide, diagnosis and treatment of diseases such as inflammations, cancers etc. by use of the DNA, the polypeptide or the antibody, determination and immunostaining of the polypeptide of the present invention by use of the antibody, a method for screening a compound varying the expression of a gene coding for the polypeptide, and a method for screening a substance varying the activity of the polypeptide.

23 Claims, 19 Drawing Sheets lane 1 Namalwa KJM-1/pAMoA
lane 2 Namalwa KJM-1/pAMoA-i52S lane 1 Namalwa KJM-1/pAMoF2 lane 2 Namalwa KJM-1/pAMoF2-i52S lane 1 Sf21/pVL1393 lane 2 Sf21/pVL1393-Ai52S lane 1 Sf21/pVL1393 lane 2 Sf21/pVL1393-F2i52S

SEQUENCE LISTING

<160> NUMBER OF SEQ ID NOS: 17

<210> SEQ ID NO 1
<211> LENGTH: 415
<212> TYPE: PRT
<213> ORGANISM: Homo sapiens

<400> SEQUENCE: 1

Met Gln Met Ser Tyr Ala Ile Arg Cys Ala Phe Tyr Gln Leu Leu Leu
 1               5                  10                  15

Ala Ala Leu Met Leu Val Ala Met Leu Gln Leu Leu Tyr Leu Ser Leu
            20                  25                  30

-continued

Leu Ser Gly Leu His Gly Gln Glu Gln Asp Gln Tyr Phe Glu Phe
         35                  40                  45

Phe Pro Pro Ser Pro Arg Ser Val Asp Gln Val Lys Ala Gln Leu Arg
     50                  55                  60

Thr Ala Leu Ala Ser Gly Val Leu Asp Ala Ser Gly Asp Tyr Arg
 65              70                  75                  80

Val Tyr Arg Gly Leu Leu Lys Thr Thr Met Asp Pro Asn Asp Val Ile
             85                  90                  95

Leu Ala Thr His Ala Ser Val Asp Asn Leu Leu His Leu Ser Gly Leu
            100                 105                 110

Leu Glu Arg Trp Glu Gly Pro Leu Ser Val Ser Val Phe Ala Ala Thr
            115                 120                 125

Lys Glu Glu Ala Gln Leu Ala Thr Val Leu Ala Tyr Ala Leu Ser Ser
        130                 135                 140

His Cys Pro Asp Met Arg Ala Arg Val Ala Met His Leu Val Cys Pro
145                 150                 155                 160

Ser Arg Tyr Glu Ala Ala Val Pro Asp Pro Arg Glu Pro Gly Glu Phe
                165                 170                 175

Ala Leu Leu Arg Ser Cys Gln Glu Val Phe Asp Lys Leu Ala Arg Val
                180                 185                 190

Ala Gln Pro Gly Ile Asn Tyr Ala Leu Gly Thr Asn Val Ser Tyr Pro
            195                 200                 205

Asn Asn Leu Leu Arg Asn Leu Ala Arg Glu Gly Ala Asn Tyr Ala Leu
        210                 215                 220

Val Ile Asp Val Asp Met Val Pro Ser Glu Gly Leu Trp Arg Gly Leu
225                 230                 235                 240

Arg Glu Met Leu Asp Gln Ser Asn Gln Trp Gly Gly Thr Ala Leu Val
                245                 250                 255

Val Pro Ala Phe Glu Ile Arg Arg Ala Arg Arg Met Pro Met Asn Lys
            260                 265                 270

Asn Glu Leu Val Gln Leu Tyr Gln Val Gly Glu Val Arg Pro Phe Tyr
        275                 280                 285

Tyr Gly Leu Cys Thr Pro Cys Gln Ala Pro Thr Asn Tyr Ser Arg Trp
    290                 295                 300

Val Asn Leu Pro Glu Glu Ser Leu Leu Arg Pro Ala Tyr Val Val Pro
305                 310                 315                 320

Trp Gln Asp Pro Trp Glu Pro Phe Tyr Val Ala Gly Lys Val Pro
                325                 330                 335

Thr Phe Asp Glu Arg Phe Arg Gln Tyr Gly Phe Asn Arg Ile Ser Gln
            340                 345                 350

Ala Cys Glu Leu His Val Ala Gly Phe Asp Phe Glu Val Leu Asn Glu
        355                 360                 365

Gly Phe Leu Val His Lys Gly Phe Lys Glu Ala Leu Lys Phe His Pro
    370                 375                 380

Gln Lys Glu Ala Glu Asn Gln His Asn Lys Ile Leu Tyr Arg Gln Phe
385                 390                 395                 400

Lys Gln Glu Leu Lys Ala Lys Tyr Pro Asn Ser Pro Arg Arg Cys
                405                 410                 415

<210> SEQ ID NO 2
<211> LENGTH: 2011
<212> TYPE: DNA
<213> ORGANISM: Homo sapiens
<220> FEATURE:

```
<221> NAME/KEY: CDS
<222> LOCATION: (80)..(1324)

<400> SEQUENCE: 2
gcggtaaatc cgggcttgcg gccgctggcg tagtctgtgg ccgggtggtc gttgctgcgc        60
gccccgagcc ccgagagcc atg cag atg tcc tac gcc atc cgg tgc gcc ttc       112
                    Met Gln Met Ser Tyr Ala Ile Arg Cys Ala Phe
                      1               5                      10 tac cag ctg ctg ctg gcc gcg ctc atg ctg gtg gcg atg ctg cag ctg       160
Tyr Gln Leu Leu Leu Ala Ala Leu Met Leu Val Ala Met Leu Gln Leu
             15                  20                  25 ctc tac ctg tcg ctg ctg tcc gga ctg cac ggg cag gag gag caa gac       208
Leu Tyr Leu Ser Leu Leu Ser Gly Leu His Gly Gln Glu Glu Gln Asp
         30                  35                  40 caa tat ttt gag ttc ttt ccc ccg tcc cca cgg tcc gtg gac cag gtc       256
Gln Tyr Phe Glu Phe Phe Pro Pro Ser Pro Arg Ser Val Asp Gln Val
     45                  50                  55 aag gcg cag ctc cgc acc gcg ctg gcc tct gga ggc gtc ctg gac gct       304
Lys Ala Gln Leu Arg Thr Ala Leu Ala Ser Gly Gly Val Leu Asp Ala
 60                  65                  70                  75 agc ggc gat tac cgc gtc tac agg ggc ctg ctg aag acc acc atg gac       352
Ser Gly Asp Tyr Arg Val Tyr Arg Gly Leu Leu Lys Thr Thr Met Asp
                 80                  85                  90 ccc aac gat gtg atc ctg gcc acg cac gcc agc gtg gac aac ctg ctg       400
Pro Asn Asp Val Ile Leu Ala Thr His Ala Ser Val Asp Asn Leu Leu
             95                 100                 105 cac ctg tcg ggt ctg ctg gag cgc tgg gag ggc ccg ctg tcc gtg tcg       448
His Leu Ser Gly Leu Leu Glu Arg Trp Glu Gly Pro Leu Ser Val Ser
        110                 115                 120 gtg ttc gcg gcc acc aag gag gag gcg cag ctg gcc acg gtg ctg gcc       496
Val Phe Ala Ala Thr Lys Glu Glu Ala Gln Leu Ala Thr Val Leu Ala
    125                 130                 135 tac gcg ctg agc agc cac tgc ccc gac atg cgc gcc agg gtc gcc atg       544
Tyr Ala Leu Ser Ser His Cys Pro Asp Met Arg Ala Arg Val Ala Met
140                 145                 150                 155 cac ctc gtg tgc ccc tcg cgt tac gag gca gcc gtg ccc gac ccc cgg       592
His Leu Val Cys Pro Ser Arg Tyr Glu Ala Ala Val Pro Asp Pro Arg
                160                 165                 170 gag ccg ggg gag ttt gcc ctg ctg cgg tcc tgc cag gag gtc ttt gac       640
Glu Pro Gly Glu Phe Ala Leu Leu Arg Ser Cys Gln Glu Val Phe Asp
            175                 180                 185 aag cta gcc agg gtg gcc cag ccc ggg att aat tat gcg ctg ggc acc       688
Lys Leu Ala Arg Val Ala Gln Pro Gly Ile Asn Tyr Ala Leu Gly Thr
        190                 195                 200 aat gtc tcc tac ccc aat aac ctg ctg agg aat ctg gct cgt gag ggg       736
Asn Val Ser Tyr Pro Asn Asn Leu Leu Arg Asn Leu Ala Arg Glu Gly
    205                 210                 215 gcc aac tat gcc ctg gtg atc gat gtg gac atg gtg ccc agc gag ggg       784
Ala Asn Tyr Ala Leu Val Ile Asp Val Asp Met Val Pro Ser Glu Gly
220                 225                 230                 235 ctg tgg aga ggc ctg cgg gaa atg ctg gat cag agc aac cag tgg gga       832
Leu Trp Arg Gly Leu Arg Glu Met Leu Asp Gln Ser Asn Gln Trp Gly
                240                 245                 250 ggc acc gcg ctg gtg gtg cct gcc ttc gaa atc cga aga gcc cgc cgc       880
Gly Thr Ala Leu Val Val Pro Ala Phe Glu Ile Arg Arg Ala Arg Arg
            255                 260                 265 atg ccc atg aac aaa aac gag ctg gtg cag ctc tac cag gtt ggc gag       928
Met Pro Met Asn Lys Asn Glu Leu Val Gln Leu Tyr Gln Val Gly Glu
        270                 275                 280
```

```
gtg cgg ccc ttc tat tat ggg ttg tgc acc ccc tgc cag gca ccc acc      976
Val Arg Pro Phe Tyr Tyr Gly Leu Cys Thr Pro Cys Gln Ala Pro Thr
285                 290                 295 aac tat tcc cgc tgg gtc aac ctg ccg gaa gag agc ttg ctg cgg ccc     1024
Asn Tyr Ser Arg Trp Val Asn Leu Pro Glu Glu Ser Leu Leu Arg Pro
300                 305                 310                 315 gcc tac gtg gta cct tgg cag gac ccc tgg gag cca ttc tac gtg gca     1072
Ala Tyr Val Val Pro Trp Gln Asp Pro Trp Glu Pro Phe Tyr Val Ala
                320                 325                 330 gga ggc aag gtg ccc acc ttc gac gag cgc ttt cgg cag tac ggc ttc     1120
Gly Gly Lys Val Pro Thr Phe Asp Glu Arg Phe Arg Gln Tyr Gly Phe
            335                 340                 345 aac cga atc agc cag gcc tgc gag ctg cat gtg gcg ggg ttt gat ttt     1168
Asn Arg Ile Ser Gln Ala Cys Glu Leu His Val Ala Gly Phe Asp Phe
        350                 355                 360 gag gtc ctg aac gaa ggt ttc ttg gtt cat aag ggc ttc aaa gaa gcg     1216
Glu Val Leu Asn Glu Gly Phe Leu Val His Lys Gly Phe Lys Glu Ala
    365                 370                 375 ttg aag ttc cat ccc caa aag gag gct gaa aat cag cac aat aag atc     1264
Leu Lys Phe His Pro Gln Lys Glu Ala Glu Asn Gln His Asn Lys Ile
380                 385                 390                 395 cta tat cgc cag ttc aaa cag gag ttg aag gcc aag tac ccc aac tct     1312
Leu Tyr Arg Gln Phe Lys Gln Glu Leu Lys Ala Lys Tyr Pro Asn Ser
                400                 405                 410 ccc cga cgc tgc tgagcccttc cctcccctaa tctgagaagt cagcctcttg         1364
Pro Arg Arg Cys
            415 gctcctcagg ccaccattta ggcctgactg ggtaagaaa tgtcgctcca ctttacagag    1424 gtagctgtgg tgttgaaaca ctggacttgg atatggggtg ctgggatcga ttcctagctt   1484 taccactaac tagctgtgtg gccttgagta aatcccgtta cctctctgag cctcggttac   1544 cctgtctgta aaagggagg tgagaatacc tacctcacgg aactgttggg aggctcagat    1604 gagatgctat atgtgaaaac attctgtaag cttcgtacaa atgtgaagta ttaatattat   1664 cgcagtatta ttgttgttat tattattgtt attattaaca atcttgggtg ggtagtagga   1724 gagcaaaaag tatgaatggg atggagctaa gaagtctgaa tacttaatga aatggacttt   1784 ttggaaagaa atcagatgaa ggcataaaat ttagttctta gctcttgaac agaagcctaa   1844 aattcctggt tctctcaggg cttcgccttc aagggttctg gaggagggaa gggtctgcag   1904 gttccatggg tgacagcctg agatctgtcc cttcaacggg ctgggctggg tatgtgccta   1964 ccgatgacaa tgtgtaaata aatgcgtgtt cacacccaca aaaaaa                  2011

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 3
ctttagagca c                                                          11

<210> SEQ ID NO 4
<211> LENGTH: 8
<212> TYPE: DNA
<213> ORGANISM: Artificial Sequence
<220> FEATURE:
<223> OTHER INFORMATION: Description of Artificial Sequence:
      Synthetic DNA
```

```
<400> SEQUENCE: 4 ctctaaag                                                              8

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 5
cgcggatcct ccccacggtc cgtggaccag                                     30

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 6
atagtttagc ggccgcggaa gggctcagca gcgtcg                              36

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 7
agcttgccgc caccatgcat tttcaagtgc agattttca                           39

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 8
gcttcctgct aatcagtgcc tcagtcataa tgtcacgtg                           39

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 9
gagattacaa ggacgacgat gacaaggcct acgtag                              36

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence:
      Synthetic DNA
```

<400> SEQUENCE: 10
gaagctgaaa atctgcactt gaaaatgcat ggtggcggca                    40

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 11
atctccacgt gacattatga ctgaggcact gattagcag                     39

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 12
gtacctacgt aggccttgtc atcgtcgtcc ttgta                         35

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 13
tggtgatcga tgtggacatg gtg                                      23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 14
caagaggctg acttctcaga ttag                                     24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 15
gatatcgccg cgctcgtcgt cgac                                     24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 16

```
caagaggctg acttctcaga ttag                                                24
```

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:
      commercially
      available amino acid sequence

<400> SEQUENCE: 17

```
Asp Tyr Lys Asp Asp Asp Asp Lys
 1               5
```

POLYPEPTIDES

This application is a divisional of application Ser. No. 09/182,450 filed Oct. 30, 1998, now U.S. Pat. No. 6,420,149.

FIELD OF THE INVENTION

The present invention relates to a polypeptide having poly-N-acetyllactosamine sugar chains synthesis-related activity, a process for producing the polypeptide, DNA coding for the polypeptide, a process for producing the DNA, a recombinant vector having the DNA integrated therein, a transformant carrying the recombinant vector, an antibody recognizing the polypeptide, a process for producing poly-N-acetyllactosamine sugar chains by use of the polypeptide, and a process for producing poly-N-acetyllactosamine sugar chains by use of the transformant carrying the recombinant vector.

BACKGROUND OF THE INVENTION

It is estimated that sugar chains are involved not only in life phenomena such as development, differentiation and cell recognition but also in occurrence and progress of inflammations, cancers, infections, auto-immune diseases and a number of other diseases [A. Kobata, S. Hakomori and K. Nagai: Glycobiology Series (1) to (6), Kodansha (1993), Glycobiology, 3, 97 (1993)].

Sugar chains exsist not only as glycoproteins, proteoglycans or glycolipids, in which they are added to proteins or lipids, but also as oligosaccharides.

The poly-N-acetyllactosamine sugar chain as the subject of the present invention is a sugar chain with the structure having N-acetyllactosamine as the repeating unit bound via β1,3 linkage [(Gal β1-4GlcNAc β1-3)n where n is 2 or more], and it exists not only in N-glycoside linked sugar chains and O-glycoside linked sugar chains on glycoproteins but also in sugar chains of glycolipids and in oligosaccharides.

The poly-N-acetyllactosamine sugar chain is synthesized by alternately reaction of β1,4-galactosyltransferases and β1,3-N-acetylglucosaminyltransferases. The gene coding for the former enzyme β1,4-galactosyltransferase has already been cloned, but the gene coding for the latter enzyme β1,3-N-acetylglucosaminyltransferase is still not cloned. With respect to β1,3-N-acetylglucosaminyltransferases having poly-N-acetyllactosamine synthesis-related activity, there are only reports on their partial purification resulting in no information of their amino acid sequences [J. Biol. Chem., 268, 27118 (1993), J. Biol. Chem., 267, 2994 (1992), J. Biol. Chem., 263, 12461 (1988), Jpn. J. Med. Sci. Biol., 42, 77 (1989)].

In some galactose residues in poly-N-acetyllactosamine sugar chains, an N-acetylglucosamine is bound via β31,6-linkage to synthesize poly-N-acetyllactosamine sugar chains having branched chains such as Galβ1-4GlcNAcβ1-3 (Galβ1-4GlcNAcβ1-6)Galβ1-4GlcNAc. A glycosyltransferase transferring such branched β1,6-bound N-acetylglucosamine is β1,6-N-acetylglucosaminyltransferase (I-branching enzyme). A gene for this enzyme has also been cloned. The linear poly-N-acetyllactosamine sugar chain (i-antigen) is recognized by anti-i antibody and the branched poly-N-acetyllactosamine sugar chain (I-antigen) is recognized by anti-I antibody [J. Biol. Chem., 254, 3221 (1979)].

Saccharides such as fucose, sialic acid, N-acetylgalactosamine, galactose etc. or sulfate groups etc are attached to linear or branched poly-N-acetyllactosamine sugar chains, and a wide variety of cell-specific or period-specific sugar chains (e.g. functional sugar chains, blood type sugar chains, cancer-related sugar chains) are formed [A. Kobata, S. Hakomori, K. Nagai: Glycobiology Series (1) to (6), Kodansha (1993), Japan].

It is known that poly-N-acetyllactosamine sugar chains having a sialyl-Lewis x sugar chain structure at their termini are present on granulocytes, monocytes or activated T cells, and these sugar chains function as ligands for E-selectin or P-selectin as adhesive molecules and are involved in accumulation of leukocytes into inflammation sites [A. Kobata, S. Hakomori, K. Nagai: Glycobiology Series (1) to (6), Kodansha (1993), Japan].

It is known that Poly-N-acetyllactosamine sugar chains having a sialyl-Lewis x sugar chain structure at their termini are present on cancer cells such as colon cancer cells, and it is suggested that these sugar chains also function as ligands for E-selectin or P-selectin and are involved in metastasis of cancer cells [A. Kobata, S. Hakomori, K. Nagai: Glycobiology Series (1) to (6), Kodansha (1993)].

It is known that the structure of poly-N-acetyllactosamine sugar chain is changed in the process of embryonic development, cell differentiation or cell transformation [A. Kobata, S. Hakomori, K. Nagai: GlycobiologySeries (1) to (6), Kodansha (1993)]. While linear poly-N-acetyllactosamine sugar chains are expressed in human embryonic erythrocytes, branched poly-N-acetyllactosamine sugar chains are expressed in human adult erythrocytes [A. Kobata, S. Hakomori, K. Nagai: Glycobiology Series (1) "World of Various Sugar Chains" Kodansha (1993)]. ABO-type blood group antigens are expressed at the termini of poly-N-acetyllactosamine sugar chains in these erythrocytes. Expression of blood group antigens at each terminus of branched poly-N-acetyllactosamine sugar chain results in multivalent antigens to increase the ability of the antigens to bind to antibodies against blood group sugar chains more than $10^3$-fold compared with that of the linear antigens.

It is known that a series of sugar-chain antigens are expressed in a regulated manner during developmental process of mouse early embryo. SSEA-1 (stage specific embryonic antigen-1) is a Lewis x sugar chain [Galβ1-4(Fuc α1-3)GlcNAc] which appears at the termini of poly-N-acetyllactosamine sugar chains, and expression of this antigen is initiated at the 8-cell stage, peaks at the morula stage, and disappears after the blastocyst stage [A. Kobata, S. Hakomori, K. Nagai: Glycobiology Series ③ "Glycobiology of Cellular Society", Kodansha (1993)]. The morula stage corresponds to the stage at which embryonic cells having increased merely numerically by repeated proliferation through cell division enter the blastocyst stage at which the cells come to have a differentiated "form". Morula cells adhere to each other just before forming a blastocyst to cause cell compaction. If an oligosaccharide having SSEA-1 antigen is added, this cell compaction is inhibited and normal development thereafter is also inhibited [J. Exp. Med., 160, 1591 (1984)]. It is also known that adhesion of mouse teratocarcinoma cells is inhibited by anti-SSEA-1 antibody [A. Kobata, S. Hakomori, K. Nagai: Glycobiology Series ③ "Glycobiology of Cellular Society", Kodansha (1993)]. The foregoing indicates that the SSEA-1 antigen acts as an adhesive molecule or a sugar chain signal to play an important role in development of early embryos.

It is known that poly-N-acetyllactosamine sugar chains are expressed at higher levels in cancer cells than in their corresponding normal cells [J. Biol. Chem., 259, 10834 (1984), J. Biol. Chem., 261, 10772 (1986), J. Biol. Chem., 266, 1772 (1991), J. Biol. Chem., 267, 5700 (1992)]. It is known that if N-ras protooncogene is expressed in NIH3T3 cells, the molecular weight of N-linked sugar chain on cells is increased, and the cells attain invasive activity, and at the same time, the amount of poly-N-acetyllactosamine sugar chains in the N-linked sugar chains is increased and simultaneously β1,4-galactosyltransferase and β1,3-N-acetylglucosaminyltransferase activities involved in synthesizing poly-N-acetyllactosamine sugar chains are increased [J. Biol. Chem., 266, 21674 (1991)].

Galectins are a family of lectins with affinity for β-galactoside, and are involved in cell adhesion and signal transduction, and their relation with diseases such as cancers is also suggested [Trends in Glycoscience and Glycotechnology, 9, 9 (1997)]. Ten types of Galectins have been found in mammals. Out of them, galectin-1 and galectin-3 are known to bind with high affinity to linear poly-N-acetyllactosamine sugar chains, and specific glycoproteins containing these sugar chains are estimated to be ligands for these galectins [Trends in Glycoscience and Glyotechology, 9, 9 (1997), Trends in Glycoscience and Glycotechnology, 9, 47 (1997)].

Poly-N-acetyllactosamine sugar chains having sialic acid residues at their termini serve as receptors for mycoplasma and microorganisms [Acta Paediatrica, 82, 903 (1993)].

As described above, poly-N-acetyllactosamine sugar chains play important roles in forming core sugar chains of many functional sugar chains (e.g. selectin ligand sugar chains, receptor sugar chains for microorganisms and viruses, SSEA-1 sugar chains and cancer-related sugar chains) and blood group. sugar chains to present these sugar chains effectively.

Poly-N-acetyllactosamine sugar chains having sialyl Lewis x sugar chains are expected to serve as a pharmaceutical product having anti-inflammatory effect or inhibitory effect for cancer metastasis.

It is known that an Poly-N-acetyllactosamine sugar chain having multivalent (4) sialyl Lewis x oligosaccharides (tetrasaccharides) has activity as selectin antagonist even at a low concentration of 1/100 or less relative to a non-multivalent sialyl Lewis x oligosaccharide (tetrasaccharide) [J. Exp. Med., 182, 1133 (1995), Glycobiology, 6, 65 (1996), Glycobiology, 7, 453 (1997), Eur. J. Immunol., 27, 1360 (1997)]. Partially purified β1,3-N-acetylglucosaminyltransferase was used for synthesis of poly-N-acetyllactosamine sugar chains in these oligosaccharides, however supply of this enzyme is rate-limiting, making it difficult to synthesize a large amount of poly-N-acetyllactosamine sugar chains [Glycobiology, 7, 453 (1997)].

Alternatively, poly-N-acetyllactosamine sugar chains can also be chemically synthesized, but their synthesis requires very complicated steps [Tetrahedron Letter, 24, 5223 (1997)].

From the foregoing, a method of efficiently synthesizing poly-N-acetyllactosamine sugar chains has been desired.

It is known that in human milk there are various oligosaccharides having the structure of poly-N-acetyllactosamine sugar chain [Acta Paediatrica, 82, 903 (1993)]. It is considered that these oligosaccharides have the function of preventing infants from being infected with viruses or microorganisms as well as the function of neutralizing toxins. They also have the activity of promoting growth of Bifidobacteria as good enterobacteria. On the other hand, the types of oligosaccharides present in milk of animals such as cattle or mice are limited, and most of them are composed of lactose, and there are few oligosaccharides containing poly-N-acetyllactosamine sugar chains [Acta Paediatrica, 82, 903 (1993), J. Biol. Chem., 270, 29515 (1995)].

It would be considered significantly advantageous if we could produce efficiently various oligosaccharides that are contained in human milk and are comprising a poly-N-acetyllactosamine sugar chain, as well as milk containing them; however, such a method has not been known.

Poly-N-acetyllactosamine sugar chains are also important for stabilization of glycoproteins. Lysosome associated membrane glycoprotein-1 (lamp-1) and lysosome associated membrane glycoprotein-2 (lamp-2) are glycoproteins present in lysosomes (some are present even on cell surfaces), with which almost all the inner face of the lysosome membrane is covered. A lot of sugar chains (some of which contain poly-N-acetyllactosamine sugar chains) are attached to lamp-1 and lamp-2, thus preventing lamp-1 and lamp-2 from being decomposed by hydrolyzing enzymes in lysosomes. If human promyelocytic leukemia cell line HL-60 is treated with dimethyl sulfoxide, it differentiated into granulocyte, and in this differentiation process it is known that the number of poly-N-acetyllactosamine sugar chains added to lamp-1 and lamp-2 is increased, and simultaneously the metabolic rate (decomposition rate) of lamp-1 and lamp-2 is decreased [J. Biol. Chem., 265, 20476 (1990)].

Because poly-N-acetyllactosamine sugar chains contribute to protein stabilization, it is considered that a protein of interest can be stabilized by artificially adding poly-N-acetyllactosamine sugar chains to the protein. Further, the clearance rate of a blood protein from kidney is decreased with an increasing effective molecular weight of the protein, thereby it would be possible to lower the clearance rate of a protein of interest from kidney and to increase its stability in blood by artificially adding poly-N-acetyllactosamine sugar chains to the protein. Furthermore, by adding poly-N-acetyllactosamine sugar chains to a protein of interest, the protein could be targeted to specific cells.

It is reported that if F9 cells are treated with retinoic acid or Swiss 3T3 are treated with TGF-β, poly-N-acetyllactosamine sugar chains are added to sugar chains of membrane-bound glycoproteins in the cells [J. Biol. Chem., 268, 1242 (1993), Biochim. Biophys. Acta., 1221, 330 (1994)].

It is known that if N-ras protooncogene is expressed in NIH3T3 cells, the activity of β1,4-galactosyltransferase and β1,3-N-acetylglucosaminyltransferase having poly-N-acetyllactosamine sugar chains synthesis-related activity is increased and the amount of the poly-N-acetyllactosamine sugar chains in the N-linked sugar chain of membrane protein is increased [J. Biol. Chem., 266, 21674 (1991)].

If a core β1,6-N-acetylglucosaminyltransferase gene is expressed in T-cell line EL-4, the molecular weight of CD43, CD45 or CD44 as a membrane protein on cell surface is increased [J. Biol. Chem., 271, 18732 (1996)]. This would be because sugar chains synthesized by core 2β1,6-N-acetylglucosaminyltransferase serve as good substrates for β1,3-N-acetylglucosaminyltransferase involved in synthesizing poly-N-acetyllactosamine sugar chains.

It is known that the amount of poly-N-acetyllactosamine sugar chains added to lamp-1 or lamp-2 is increased when HL-60 cells are cultured at 27° C. [J. Biol. Chem., 266, 23185 (1991)].

However, it is not clear whether the above method is effective or not in host cells suitable for production of recombinant glycoproteins. Accordingly, for host cells (e.g. Namalwa cells, Namalwa KJM-1 cells, CHO cells etc.) suitable for production of recombinant glycoproteins, improvement of their ability to synthesize poly-N-acetyllactosamine sugar chains is an industrially important subject.

In consideration of the mechanism of the above-described inflammatory reaction and cancer metastasis, it is expected that the inflammatory reaction can be inhibited and the cancer metastasis can be prevented by inhibiting expression of poly-N-acetyllactosamine sugar chains. However, a method of efficiently inhibiting expression of poly-N-acetyllactosamine sugar chains is not known.

It is expected that inflammatory diseases or cancer malignancy can be diagnosed by examining expression of genes (e.g. a gene for β1,3-N-acetylglucosaminyltransferase as a key enzyme in synthesis of poly-N-acetyllactosamine sugar chains) involved in synthesizing poly-N-acetyllactosamine sugar chains or by examining expression of polypeptides coded by their genes in inflammatory leukocytes, cancer cells or in serum. However, such a method is not known.

SUMMARY OF THE INVENTION

The present invention provides pharmaceutical for anti-inflammation, anti-infection, cancer-metastasis inhibition etc., foods such as dairy products etc., and a method of improving proteins, as well as a diagnostic method for inflammatory diseases and cancer malignancy.

The present invention relates to a polypeptide having poly-N-acetyllactosamine sugar chains synthesis-related activity, a process for producing the polypeptide, DNA coding for the polypeptide, a process for producing the DNA, a recombinant vector having the DNA integrated therein, a transformant carrying the recombinant vector, an antibody recognizing the novel peptide, a process for producing poly-N-acetyllactosamine sugar chains by use of the DNA or the polypeptide, diagnosis and treatment of diseases such as inflammations, cancers etc. by use of the DNA, the polypeptide or the antibody, determination and immunostaining of the polypeptide of the present invention by use of the antibody, a method of screening a compound varying the expression of a gene coding for the polypeptide, and a method of screening a substance varying the activity of the polypeptide.

Figure 1:
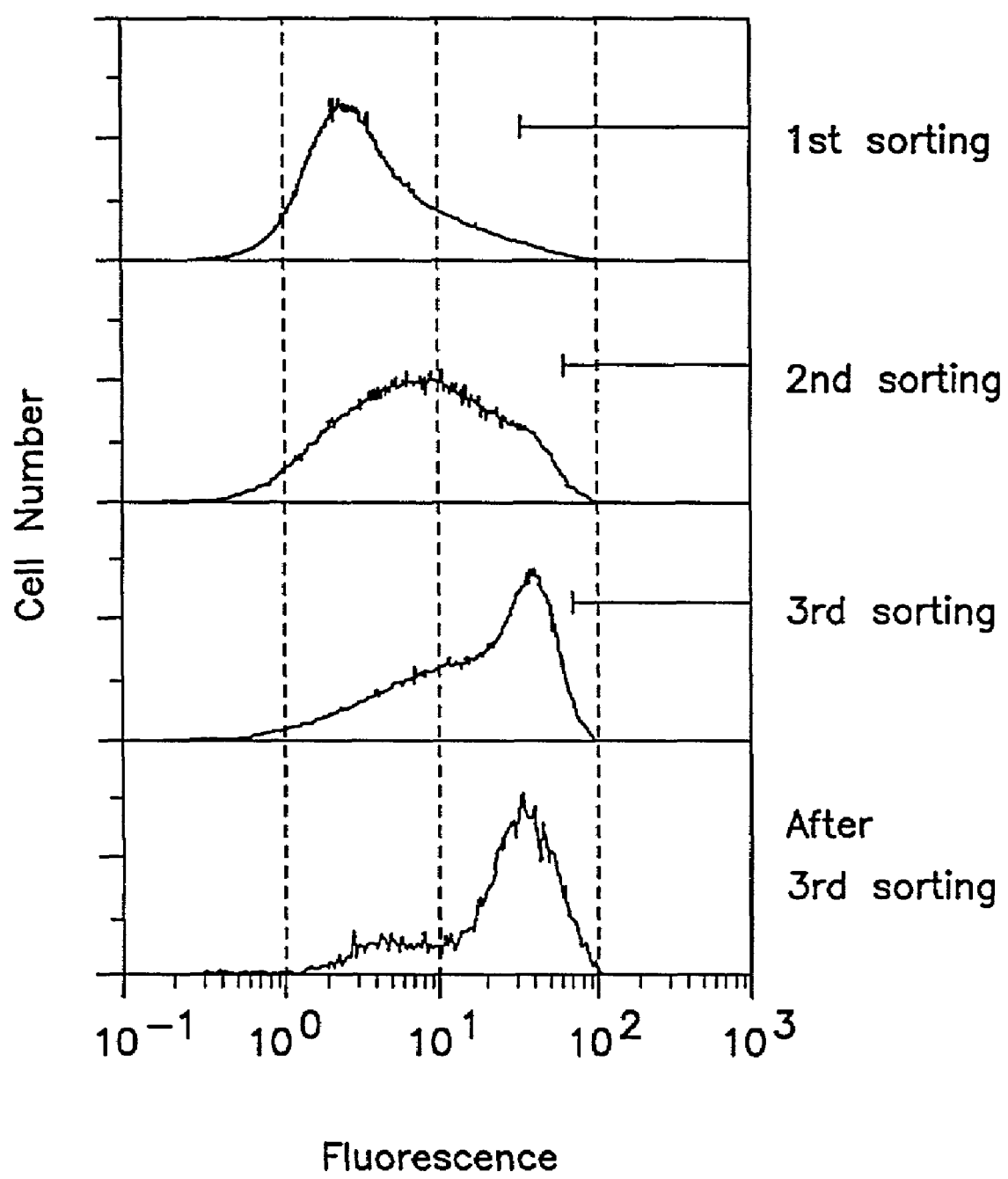
FIG. 1 shows the process of expression cloning. Namalwa KJM-1 cells to which cDNA libraries derived from WM266-4 and SW1116 had been introduced was subjected to fluorescence staining with anti-i antibody followed by FACS, and cells with high reactivity with the anti-i antibody were collected. The cells indicated by the bars were collected and subjected to next FACS. After three rounds of FACS, cells with high reactivity with the anti-i antibody were concentrated.

The meanings of the symbols are as follows:
bp: base pairs
kb: kilobase pairs
G418/km: transposon 5 (Tn5)-derived G418, kanamycin-resistant gene
Ap: pBR322-derived ampicillin resistant gene.
Tc: pBR322-derived tetracycline resistant gene.

P1: pBR322-derived P1 promoter.
Ptk: Herpes simplex virus (HSV) thymidine kinase (tk) gene promoter.
Sp. BG: rabbit β-globin gene splicing signal.
A. BG: rabbit β-globin gene polyadenylaton signal.
A. SE: simian virus 40 (SV40) early gene polyadenylaton signal.
Atk: Herpes simplex virus (HSV) thymidine kinase (tk) gene polyadenylaton signal.
Pse: simian virus 40 (SV40) early gene promoter.
Pmo: Moloney murine leukemia virus long terminal repeat (LTR) promoter.
EBNA-1: Epstein-Barr virus EBNA-1 gene.
oriP: replication origin of Epstein-Barr virus.
S: A gene coding for a signal peptide of human granulocyte colony stimulating factor or immunoglobulin κ.
A or ProA: A gene coding for a IgG-binding domain of *Staphylococcus aureus* protein A.
F: A gene coding for the Flag peptide.
iGnT: DNA obtained in the present invention, which codes for the full or a part of the polypeptide having poly-N-acetyllactosamine sugar chains synthesis-related activity.
cDNA: DNA obtained in the present invention, which codes for the full or a part of the polypeptide having poly-N-acetyllactosamine sugar chains synthesis-related activity.
cDNA del: Partial-length DNA obtained in the present invention, which has a deletion of about 0.2-kb DNA fragment and encodes a part of the polypeptide having poly-N-acetyllactosamine sugar chains synthesis-related activity.

DETAILED DESCRIPTION OF THE PREFERRED EMBODIMENTS

The DNA of the present invention is DNA coding for a polypeptide having poly-N-acetyllactosamine sugar chains synthesis-related activity, and mention can be made of DNA coding for a polypeptide having the amino acid sequence shown in SEQ ID NO:1, or DNA coding for a polypeptide having an amino acid sequence where in SEQ ID NO:1, one or more amino acids have been replaced, deleted or added and having poly-N-acetyllactosamine sugar chains synthesis-related activity, or DNA hybridizing with said DNA under stringent conditions and coding for a polypeptide having poly-N-acetyllactosamine sugar chains synthesis-related activity.

The polypeptide having poly-N-acetyllactosamine sugar a chains synthesis-related activity includes e.g. a polypeptide having β1,3-N-acetylglucosaminyltransferase activity.

The DNA capable of hybridizing under stringent conditions means a DNA obtained by colony hybridization, plaque hybridization, Southern blot hybridization or the like with said DNA as the probe. A specific example include DNA which can be identified by carrying out hybridization at 65° C. in the presence of 0.7 to 1.0 M NaCl using a filter on which a DNA prepared from colonies or plaques is immobilized and then washing the filter at 65° C. with a 0.1 to 2-fold conc. SSC solution (1-fold conc. SSC solution is composed of 150 mM sodium chloride and 15 mM sodium citrate). Hybridization can be effected according to a method described in e.g. Molecular Cloning, A laboratory Manual, Second Edition, Cold Spring Harbor Laboratory Press (1989) (abbreviated hereinafter to Molecular Cloning, 2nd edition). Specifically the DNA capable of hybridizing includes DNA having 60% or more homology, preferably 80% or more homology, more preferably 95% or more homology with a nucleotide sequence coding for a polypeptide having the amino acid sequence of SEQ ID NO:1.

The polypeptide of the present invention includes a polypeptide encoded by said DNA, and specifically, it includes e.g. a polypeptide having the amino acid sequence shown in SEQ ID NO:1, or a polypeptide having an amino acid sequence where in SEQ ID NO:1, one or more amino acids have been substituted, deleted or added and participating in synthesis of poly-N-acetyllactosamine sugar chains.

The polypeptide having an amino acid sequence wherein one or more amino acids substituted, deleted or added in the amino acid sequence of the polypeptide and participating in synthesis of poly-N-acetyllactosamine sugar chains can be prepared in accordance with known methods described in Nucleic Acids Research, 10, 6487 (1982), Proc. Natl. Acad. Sci., USA, 79, 6409 (1982), Proc. Natl. Acad. Sci., USA, 81, 5662 (1984), Science, 224, 1431 (1984), PCT WO85/00817 (1985), Nature, 316, 601 (1985), Gene, 34, 315 (1985), Nucleic Acids Research, 13, 4431 (1985), Current Protocols in Molecular Biology, 8 ch. Mutagenesis of Cloned DNA, John Wiley & Sons, Inc. (1989) etc.

The antibodies of the present invention includes antibodies recognizing the above-described polypeptides.

Hereinafter, the present invention is described in detail.

(1) Production of DNA Coding for a Polypeptide Related to Synthesis of poly-N-acetyllactosamine Sugar Chains A cDNA library is prepared in a usual manner from cells expressing poly-N-acetyllactosamine sugar chains.

The method of preparing the cDNA library includes methods described in Molecular Cloning, 2nd edition, Current Protocols in Molecular Biology, Supplements 1-34, Greene Publishing Associates and Wiley-Interscience, 1987-1996 edition (abbreviated hereinafter to Current Protocols in Molecular Biology Supplements 1-34) etc. or methods using commercially available kits such as SuperScript Plasmid System for cDNA Synthesis and Plasmid Cloning (Gibco BRL) and ZAP-cDNA Synthesis Kit (Stratagene) etc.

Cells expressing poly-N-acetyllactosamine sugar chains may be any cells expressing poly-N-acetyllactosamine sugar chains, and examples are human melanoma cell line WM266-4 (ATCC CRL 1676), human colon cancer cell line SW1116 (ATCC CRL 233), human monocyte cell line THP-1 (ATCC TIB 202), human hisiticocytic lymphoma cell line U-937 (ATCC CRL 1593), human promyelocytic leukemia cell line HL-60 (ATCC CCL 240) etc.

The cloning vector for preparing the cDNA library may be any phage vectors, plasmid vectors etc. insofar as they can be autonomously replicated in *E. coli* K12. Specific examples includes ZAP Express [Strategies, 5, 58 (1992), a product of Stratagene], pBluescript II SK(+) [Nucleic Acids Research, 17, 9494 (1989)], λ zap II (Stratagene), λ gt10, λ gt11 [DNA Cloning, A Practical Approach, 1, 49 (1985)], Lambda BlueMid (Clonetech), λ ExCell (Pharmacia), pT7T3 18U (Pharmacia), pcD2 (Mol. Cell. Biol., 3, 280 (1983), pUC18 [Gene, 33, 103 (1985)], pAMo [J. Biol. Chem., 268, 22782-22787 (1993), also called pAMoPRC3Sc (Japanese Published Unexamined Patent Application No. 336963/93)] etc.

The host microorganisms may be any microorganisms belonging to *Escherichia coli*. Specifically, use is made of *Escherichia coli* XL1-Blue MRF' [Strategies, 5, 81 (1992), a product of Stratagene], *Escherichia coli* C600 [Genetics, 39, 440 (1954)], *Escherichia coli* Y1088 [Science, 222, 778 (1983)], *Escherichia coli* Y1090 [Science, 222, 778 (1983)], *Escherichia coli* NM522 [J. Mol. Biol., 166, 1 (1983)],

*Escherichia coli* K802 [J. Mol. Biol., 16, 118 (1996)] and *Escherichia coli* JM105 [Gene, 38, 275 (1985)].

As the cDNA library, mention can be made of a cDNA library prepared by synthesizing cDNA with a cDNA synthesis system (GIBCO BRL) using mRNA derived from WM266-4 or SW1116, then linking a SfiI linker to both termini of the cDNA, inserting the resulting cDNA between SfiI sites of cloning vector pAMo and transforming the resulting plasmid into *E. coli* LE392.

The inserted DNA is cut off from the cDNA library and integrated into a vector for expression in animal cells or insect cells. If a vector for expression in animal cells or insect cells is used at the time of constructing the cDNA library, the product can be used as the expression vector described below without conducting said operation.

Any vector capable of expressing the cDNA integrated therein can be used as the vector, and for example, mention can be made of pcDNAI/Amp, pcDNAI, pCDM8 (which all are available from Funakoshi K. K.), pAGE107 [Japanese Published Unexamined Patent Application No. 22979/91, Cytotechnology, 3, 133 (1990)], pREP4 (Invitrogen), pAGE103 [J. Biochem., 101, 1307 (1987)], pAMo, pAMoA [J. Biol. Chem., 268, 22782-22787 (1993), also called pAMoPRSA (Japanese Published Unexamined Patent Application No. 336963/93], pAS3-3 (Japanese Published Unexamined Patent Application No. 227075/90), pVL1392 (Invitrogen), pVL1393 (Invitrogen), and pBlueBacIII (Invitrogen) etc.

The expression vector into which the DNA excised from the cDNA library has been integrated is introduced into animal cells or insect cells capable of expressing the objective DNA in the expression vector to obtain transformant.

The method of introducing the recombinant vector may be any method of introducing DNA into animal cells or insect cells, and mention can be made of e.g. the electroporation method [Cytotechnology, 3, 133 (1990)], the calcium phosphate method (Japanese Published Unexamined Patent Application No. 227075/90), the lipofection method [Proc. Natl. Acad. Sci. USA, 84, 7413 (1987)] and methods described in Baculovirus Expression Vectors, W. H. Freeman and Company, New York (1992); Molecular Biology, A Laboratory Manual; Current Protocols in Molecular Biology; Bio/Technology, 6, 47 (1988) etc.

The animal cells or insect cells used include Namalwa cells that are human cells, COS cells that are monkey cells, CHO cells that are Chinese hamster cells, HBT5637 (Japanese Published Unexamined Patent Application No. 299/88), Sf9 and Sf21 that are ovary cells from *Spodoptera frugiperda* [Baculovirus Expression Vectors (1992)], High 5 (Invitrogen) that is ovary cells from *Trichoplusia ni* etc. Preferable host cells are Namalwa cells.

The resulting transformed cells were subjected to fluorescence staining with an antibody against poly-N-acetyllactosamine sugar chains or a lectin recognizing poly-N-acetyllactosamine sugar chains, followed by sorting with fluorescence activated cell sorter (hereinafter abbreviated to FACS) to concentrate and separate the cells with increased binding of the antibody or lectin recognizing linear poly-N-acetyllactosamine sugar chains.

The antibody against poly-N-acetyllactosamine sugar chains may be any antibody which can react with poly-N-acetyllactosamine sugar chains, and for example, anti-i antibody recognizing linear poly-N-acetyllactosamine sugar chains [J. Biol. Chem., 254, 3221 (1979)] can be used. Furthermore, the lectin recognizing poly-N-acetyllactosamine sugar chains can be used in place of the antibody, and for example, Datura stramonium lectin (DSA), *Lycopersicon esculentum* lectin (LEA) and *Phytolacca americana* lectin (PWA) can be used.

From the cells concentrated and separated in this manner, the plasmid carring the DNA of the present invention can be recovered using e.g. the Hart method [Mol. Cell. Biol., 8, 2837 (1988)] to give a DNA fragment containing the DNA.

The plasmid containing the DNA of the present invention includes e.g. pVL1393-i. *Escherichia coli* MM294/pVL1393-i that is *E. coli* harboring pVL1393-i was deposited as FERM BP-6145 on Oct. 16, 1997 with the National Institute of Bioscience and Human-Technology, Agency of Industrial Science and Technology, Japan, under the Budapest Treaty.

The nucleotide sequence of the DNA thus obtained can be determined by conventional nucleotide sequence analyses using the dideoxy termination method of Sanger et al. [Proc. Natl. Acad. Sci. USA, 74, 5463 (1977)] or a nucleotide sequencer such as 373A•DNA sequencer [Perkin Elmer] with the DNA fragment as is or inserted into a vector after digestion with appropriate restriction enzymes etc.

The DNA obtained by said method includes e.g. DNA coding for the peptide of SEQ ID NO:1, and specifically, DNA having the nucleotide sequence of SEQ ID NO:2 can be mentioned.

The DNA can also be prepared by chemical synthesis in a DNA synthesizer on the basis of the determined nucleotide sequence. The DNA synthesizer may be a DNA synthesizer using the thiophosphite method (Shimadzu Corporation), a DNA synthesizer model 392 using the phosphoamidite method (Perkin Elmer) or the like.

The objective DNA can also be preparedbypolymerase chain reaction (abbreviated hereinafter to PCR) where oligonucleotides described below are used as sense and antisense primers and cDNA prepared from mRNA of cells expressing mRNA complementary to the DNA is used as a template [Molecular Cloning, 2nd edition and PCR Protocols Academic Press (1990)].

The DNA and DNA fragment obtained in the above-described methods can be used to prepare oligonucleotides such as antisense oligonucleotide, sense oligonucleotide etc. having a partial sequence of the DNA of the present invention. The oligonucleotides include DNA having the same sequence as a sequence of contiguous 10 to 50 nucleotides in the objective DNA, or DNA having a complementary sequence to said DNA, and specific examples include DNA having the same sequence as a contiguous 10- to 50-nucleotide sequence in the nucleotide sequence of SEQ ID NO:2, or DNA having a complementary sequence to said DNA. If these are used as sense and antisense primers, two oligonucleotides described above having similar melting temperatures (Tm) and similar numbers of nucleotides are preferably used.

These oligonucleotides can also be mentioned as the DNA of the present invention.

Furthermore, derivatives of these oligonucleotides can also be mentioned as the DNA of the present invention. The derivative DNA includes derivative DNA whose phosphate diester linkage was replaced by a phosphorothioate linkage, derivative DNA whose phosphate diester linkage was replaced by a N3'-P5' phosphoamidate linkage, derivative DNA whose ribose and phosphate diester linkage was replaced by a peptide-nucleic-acid linkage, derivative DNA whose uracil was replaced by C-5 propinyl uracil, derivative DNA whose uracil was replaced by C-5 thiazol uracil, derivative DNA whose cytosine was replaced by C-5 propinyl cytosine, derivative DNA whose cytosine was replaced by phenoxazine-modified cytosine, derivative DNA whose ribose was replaced by 2'-O-propyl ribose, or derivative DNA whose ribose was replaced by 2'-methoxyethoxyribose [Saibo Kogaku, 16, 1463 (1997)].

(2) Production of a Polypeptide Having poly-N-acetyllactosamine Sugar Chains Synthesis-related Activity To express thus obtained DNA of the present invention thus obtained in host cells and to produce the polypeptide of the prsent invention, the methods described in Molecular Cloning, 2nd edition or Current Protocols in Molecular Biology Supplements 1-34 etc. can be used.

That is, the polypeptide of the present invention can be produced by inserting the DNA of the present invention into a site downstream from a promoter in a suitable expression vector to construct a recombinant vector, then introducing the vector into host cells to prepare a transformant expressing the polypeptide of the present invention, and culturing the transformant.

The host calls may be any of prokaryotes, yeasts, animal cells, insect cells, plant cells insofar as they can express the objective gene. Animals or plants can be used as such.

The expression vector used is the one being capable of autonomous replication in the host cells or capable of integration into the chromosome and containing a promoter at a site suitable for transcription of the gene involved in synthesizing poly-N-acetyllactosamine sugar chains.

If prokaryotes such as bacteria are used as the host, it is preferable that an expression vector of the gene relating to synthesizing poly-N-acetyllactosamine sugar chains is autonomously replicable in the prokaryotes and thevector is composed of a promoter, a ribosome-binding sequence, the gene relating to synthesizing poly-N-acetyllactosamine sugar chains, and a transcription termination sequence. The vector may also contain a gene for regulating the promoter.

The expression vector includes e.g. pBTrp2, pBTac1, pBTac2 (which all are commercially available from Boehringer Mannheim), pSE280 (Invitrogen), pGEMEX-1 (Promega), pQE-8 (Qiagen), pKYP10(Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescript II SK(−)(Stratagene), pTrs30 (FERM BP-5407), pTrs32 (FERM BP-5408), pGHA2 (FERM BP-400), pGKA2 (FERM BP-6798), pTerm2 (Japanese Published Unexamined Patent Application No. 22979/91, U.S. Pat. No. 4,686,191, U.S. Pat. No. 4,939,094, U.S. Pat. No. 5,160,735), pKK233-2 (Pharmacia), pGEX (Pharmacia), pET system (Novagen), pSupex, pUB110, pTP5, pC194, pTrxFus (Invitrogen), pMAL-c2 (NewEnglandBiolabs), pEG400[J. Bacteriol., 172, 2392 (1990)] etc.

The promoter may be any one insofar as it is capable of working in hosts such as $E.\ coli$ etc. Examples are promoters derived from $E.\ coli$, phage etc., such as trp promoter (Ptrp), lac promoter (Plac), $P_L$ promoter, $P_R$ promoter, PletI promoter, $P_{SE}$ promoter etc. as well as SP01 promoter, SPO2 promoter, penP promoter etc. Artificially designed and modified promoters such as a Ptrp×2 promoter having two trp promoters in tandem, tac promoter etc. can also be used.

A plasmid in which the distance between a Shine-Dalgarno sequence and an initiation codon is adjusted to an appropriate distance (e.g. 6 to 18 nucleotides)may be preferably used.

Although a transcription termination sequence is not necessarily required to express the DNA of the present invention, it is preferable to locate the transcription termination sequence just downstream from the structural gene.

The host cells include microorganisms belonging to the genus *Escherichia, Serratia, Corynebacterium, Brevibacterium, Pseudomonas, Bacillus, Microbacterium* etc. Specific examples are *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* GI698, *Escherichia coli* GI724, *Escherichia coli* TB1, *Bacillus subtilis, Bacillus amyloliquefacines, Brevibacterium ammoniagenes, Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium glutamicum* ATCC14297, *Corynebacterium glutamicum* ATCC13869, *Corynebacterium acetoacidophilum* ATCC13870, *Microbacterium ammoniaphilum* ATCC15354, *Pseudomonas putida, Pseudomonas* sp. D-0110, *Serratia marcescens, Serratia ficaria, Serratia fonticola, Serratia liquefaciens* etc.

The method of introducing the recombinant vector may be any method of introducing DNA into the host cells described above, and for example, mention can be made of a method of using calcium ions [Proc. Natl. Acad. Sci. USA, 69, 2110 (1972)], the protoplast method (Japanese Published Unexamined Patent Application No. 248394/88), methods described in Gene, 17, 107 (1982) and Molecular & General Genetics, 168, 111 (1979).

If yeasts are used as the host cells, expression vectors such as YEp13 (ATCC37115), YEp24 (ATCC37051), YCp50 (ATCC37419), pHS19, pHS15 etc. can be exemplified.

Any promoters can be used insofar as they are capable of working in yeasts. For example, mention can be made of promoters such as PHO5 promoter, PGK promoter, GAP promoter, ADH promoter, gal 1 promoter, gal 10 promoter, heat shock protein promoter, MF α1 promoter, CUP 1 promoter etc.

The host cells include yeast strains belonging to the genus *Kluyveromyces, Saccharomyces, Schizosaccharomyces, Trichosporon, Schwanniomyces* etc. Specifically, mention can be made of *Saccharomyces cerevisiae, Schizosaccharomyces pombe, Kluyveromyces lactis, Trichosporon pullulans, Schwanniomyces alluvius* etc.

The method of introducing the recombinant vector may be any method of introducing DNA into yeast, and examples include the electoporation method [Methods Enzymol., 194, 182 (1990)], the spheroplast method [Proc. Natl. Aad. Sci. USA, 75, 1929 (1978)], the lithium acetate method [J. Bacteriol., 153, 163 (1983)], a method described in Proc. Natl. Acad. Sci. USA, 75, 1929 (1978) and the like.

If animal cells are used as the host cells, expression vectors such as pcDNAI/Amp (manufactured by Invitrogen), pcDNAI, pCDM8 [Nature, 329, 840 (1987)], pAGE107 (Japanese Published Unexamined Patent Application No. 22979/91), pREP4 (manufactured by Invitogen), pAGE103 [J. Biochem., 101, 1307 (1987)], pAMo, pAMoA, pAS3-3 (Japanese Published Unexamined Patent Application No. 227075/90) etc. can be used.

The promoter used may be any promoter capable of working in animal cells. Examples are a promoter of IE (immediate early) gene of cytomegalovirus (human CMV), SV40 early promoter, long terminal repeat promoter of moloney murine leukemia virus, a retrovirus promoter, a heat shock promoter, SR α promoter and a metallothionein promoter. Furthermore, an enhancer of the IE gene of human CMV may be used together with the promoter.

The host cells include mouse myeloma cells, rat myeloma cells, mouse hybridoma cells, CHO cells that are Chinese hamster cells, BHK cells, African green monkey renal cells, Namalwa cells that are human cells, human embryonic renal cells, human leukemia cells, HBT5637 (Japanese Published Unexamined Patent Application No. 299/88) etc.

The mouse myeloma cells include SP2/0, NS0 etc.; the rat myeloma cells include YB2/0 etc.; the human embryonic renal cells include HEK293 (ATCC: CRL-1573), etc.; human leukemia cells include BALL-1 etc.; and the African green monkey renal cells include COS-1, COS-7 etc.

The method of introducing the recombinant vector may be any method of introducing DNA into animal cells. For example, it is possible to use the electroporation method [Cytotechnology, 3, 133 (1990)], the calcium phosphate method (Japanese Published Unexamined Patent Application No. 227075/90), the lipofection method [Proc. Natl. Acad. Sci. USA, 84, 7413 (1987)], a method described in Virology, 52, 456 (1973) and so on.

If insect cells are used as the host, the protein can be expressed by methods described in Baculovirus Expression Vectors, A Laboratory Manual, W. H. Freeman and Company, New York (1992); Molecular Biology, A Laboratory Manual; Current Protocols in Molecular Biology Supplements 1-38; Bio/Technology, 6, 47 (1988) and so on That is, the vector for transferring the recombinant gene and baculovirus are simultaneously introduced into insect cells so that a recombinant virus is obtained in the culture supernatant of the insect cells, and then insect cells are infected with the recombinant virus whereby the protein can be expressed.

The gene transfer vector used in this method includes e.g. pLV1392, pVL1393, pBlueBacIII (which all are products of Invitrogen) and so on.

As the baculovirus, it is possible to employ e.g. Autographa californica nuclear polyhedrosis virus, that is, a virus infecting insects of the family Barathra.

As the insect cells, it is possible to use *Spodopetera frugiperda* oocytes, *Trichoplusia ni* oocytes, cultured cells derived from silkworm ovaries etc.

*Spodoptera frugiperda* oocytes include Sf9, Sf21 (Baculovirus Expression Vectors, A Laboratory Manual) etc.; *Trichoplusia ni* oocytes include High 5, BTI-TN-5B1-4 (Invitrogen) etc.; and the cultured cells derived from silkworm ovaries include *Bombyx mori* N4 etc.

As co-transfer methods of both the aforesaid vector for transferring the recombinant gene and the aforesaid baculovirus to prepare the recombinant virus, for example, the calcium phosphate method (Japanese Published Unexamined Patent Application No. 227075/1990), the lipofection method [Proc. Natl. Acad. Sci. USA, 84, 7413 (1987)] etc. may be used.

The same method as for introducing DNA into animal cells can be used for introducing DNA into insect cells. For example, mention can be made of the electroporation method [Cytotechnology, 3, 133 (1990)], the calcium phosphate method (Japanese Published Unexamined Patent Application No. 227075/90), the lipofection method [Proc. Natl. Acad. Sci. USA, 84, 7413 (1987)] etc.

If plant cells or plants themselves are used as the host, the protein can be produced according to methods known in the art [Soshiki Baiyo (tissue culture), 20 (1994), Soshiki Baiyo (tissue culture), 21 (1995), Trends in Biotechnology, 15, 45 (1997)].

Any promoter capable of working in plant cells can be used as the promoter used for gene expression, and examples include 35S promoter of cauliflower mosaic virus (CaMV), rice actin 1 promoter etc. Furthermore, the efficiency of expression of the gene can also be raised by inserting e.g. intron 1 of a corn alcohol dehydrogenase gene into a region between the promoter and the gene to be expressed.

The host cells include plant cells such as potato, tobacco, corn, rice, rape, soybean, tomato, wheat, barley, rye, alfalfa, linum etc.

The method of introducing the recombinant vector may be any method of introducing DNA into plant cells. For example, it is possible to use a method using *Agrobacterium*, the electroporation method [Cytotechnology, 3, 133 (1990)] or a method using a particle gun (gene gun).

The plant cells or organs to which the gene was introduced can be cultured in large scale in a jar fermenter. Furthermore, plant cells to which the gene was introduced can be re-differentiated to produce a plant (transgenic plant) having the gene introduced to it.

An animal can also be used to produce the protein of the present invention. For example, the protein of the present invention can be produced according to methods known in the art [American Journal of Clinical Nutrition, 63, 639S (1996), American Journal of Clinical Nutrition, 63, 627S (1996), Bio/Technology, 9, 830 (1991)] in an animal to which the gene was introduced.

The promoter used may be any promoter capable of working in an animal. For example, mammary gland cell-specific promoters such as α-casein promoter, β-casein promoter, β-lactoglobulin promoter, whey acidic protein promoter etc. are preferably used.

A transformant harboring recombinant vector containing DNA coding for the polypeptide of the present invention is cultured in a usual culture method until the polypeptide is expressed and accumulated, and the polypeptide is recovered from the culture whereby said polypeptide can be produced.

If the transformant is an animal or plant, it is raised or cultured in a usual manner until the polypeptide is expressed and accumulated, and the polypeptide is recovered from the animal or plant whereby said polypeptide can be produced.

That is, in the case of the animal, for example, a non-human transgenic animal carrying the DNA of the present invention is raised so that the polypeptide, which is encoded by said recombinant DNA and has poly-N-acetyllactosamine sugar chains synthesis-related activity, is expressed and accumulated in the animal, and said polypeptide is recovered from the animal whereby the polypeptide having poly-N-acetyllactosamine sugar chains synthesis-related activity can be produced. The place where the polypeptide is expressed and accumulated in the animal is for example milk, egg etc. of the animal.

In the case of the plant, for example, a transgenic plant carrying the DNA of the present invention is cultured so that the polypeptide, which is encoded by said recombinant DNA and has poly-N-acetyllactosamine sugar chains synthesis-related activity, is expressed and accumulated in the plant, and said polypeptide is recovered from the plant whereby the polypeptide having poly-N-acetyllactosamine sugar chains synthesis-related activity can be produced.

If the transformants for producing the polypeptide of the present invention are prokaryotes such as *E. coli* etc. or eukaryotes such as yeast etc., the medium for culture of these organisms may be natural or synthetic mediun insofar as the medium contains a carbon source, a nitrogen source, inorganic salts etc. which can be assimilated by the said organisms and in which the transformants can be efficiently cultured.

Any carbon source can be used insofar as it can be assimilated by the microorganisms, and the following can be used: carbohydrates such as glucose, fructose, sucrose, molasses containing them, starch or starch hydrolysates; organic acids such as acetic acid, propionic acid; alcohols such as ethanol, propanol, and the like.

As a nitrogen source, the following can be used: ammonium salts of various inorganic acids and organic acids, such as ammonia, ammonium chloride, ammonium sulfate, ammonium acetate, and ammonium phosphate; other nitrogen-containing compounds; and peptone, meat extracts, yeast extracts, corn steep liquor, casein hydrolysates, soy bean meal, soy bean meal hydrolysates, various fermented cells and hydrolysates thereof and the like.

The inorganic salts used include potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

The culturing is conducted under aerobic conditions using e.g. shake culture or aeration stirring culture or the like means. The culturing temperature is preferably 15 to 40° C., and the culturing period is usually 16 hours to seven days. During culturing, pH is maintained at 3.0 to 9.0. Adjustment of the medium pH is conducted using an inorganic or organic acid, an alkaline solution, urea, calcium carbonate, ammonia and the like.

If necessary, additionally, antibiotics such as ampicillin and tetracycline may be added to the medium during the culturing.

For culturing a microorganism transformed with an expression vector using an inductive promoter as a promoter, an inducer maybe added to the medium, if necessary. For example, for culturing a microorganism transformed with an expression vector using lac promoter, isopropyl-β-D-thiogalactopyranoside (IPTG) or the like may be added to the medium; for culturing a microorganism transformed with an expression vector using trp promoter, indole acrylic acid (IAA) or the like may satisfactorily be added to the medium.

If the transformants for producing the polypeptide of the present invention are animal cells, the medium for culturing the cells is a generally used medium such as RPMI1640 medium [The Journal of the American Medical Association, 199, 519 (1967)], Eagle's MEM medium [Science, 122, 501 (1952)], DMEM medium [Virology, 8, 396 (1959)], 199 medium [Proceeding of the Society for the Biological Medicine, 73, 1 (1950)] or any one of these media further supplemented with fetal calf serum.

The culturing is conducted usually for 1 to 7 days at pH 6 to 8, at 30 to 40° C. in the presence of 5% $CO_2$.

If necessary, antibiotics such as kanamycin and penicillin may be added to the medium during the culturing.

The medium for culturing the transformant obtained from insect cells as host may be a generally used medium such as TNM-FH medium (Pharmingen), Sf-900 II SFM medium (Life Technologies), ExCell 400 and ExCell 405 [both are products of JRH Biosciences], Grace's Insect Medium [Grace, T. C. C., Nature, 195, 788 (1962)] or the like.

The culturing is conducted preferably at pH 6 to 7, at a temperature of 25 to 30° C. for a period of usually 1 to 5 days.

If necessary, antibiotics such as gentamycin may be added to the medium during the culturing.

The method of expressing the gene includes secretion-type expression, fusion protein expression etc. in accordance with the methods described in Molecular Cloning, 2nd edition, in addition to direct expression.

The method of producing the polypeptide of the present invention includes intracellular production by host cells, extracellular secretion by host cells or production on outer membranes by host cells, and the method can be selected depending on the host cells used or on alternation of the structure of the polypeptide to be produced.

If the polypeptide of the present invention is produced in host cells or on outer membranes of host cells, the polypeptide can be efficiently secreted to extracellular portion from the host cells by use of the method of Paulson et al. [J. Biol. Chem., 264, 17619 (1989)], the method of Lowe et al. [Proc. Nat. Acad. Sci., USA, 86, 8227 (1989), Genes Develop., 4, 1288 (1990)] or methods described in e.g. Japanese Published Unexamined Patent Application Nos. 336963/93 and 823021/94.

That is, the polypeptide of the present invention can be efficiently secreted by expressing it as a form in which a signal peptide was added upstream of a polypeptide portion containing the active site of the polypeptide of the present invention, which can be achieved using gene manipulation techniques.

The amount of the polypeptide produced can be increased by a gene amplification system using a dihydrofolate reductase gene or the like according to a method described in Japanese Published Unexamined Patent Application No. 227075/90.

For isolation and purification of the polypeptide of the present invention from a culture of the transformant for producing the polypeptide of the present invention, conventional methods for the isolation and purification of enzymes can be used.

For example, if the polypeptide of the present invention is accumulated as soluble forms in cells of the transformant for producing the polypeptide of the present invention, the cells are recovered from the culture by centrifuging the culture, then washed and disrupted with ultrasonic disrupter, French Press, Manton-Gaulin homogenizer, Dynomill or the like, to obtain a cell-free extract.

A purified preparation can be obtained by centrifuging the cell free extract to obtain the supernatant and then by subjecting the supernatant to solvent extraction, salting-out or desalting with sulfate ammonium etc., precipitation with organic solvent, anion-exchange chromatography on resin such as diethylaminoethyl (DEAE)-Sepharose, DIAION HPA-75 (Mitsubishi Chemical Industries Ltd.) or the like, anion-exchange chromatography on resin such as S-Sepharose FF (Pharmacia) or the like, hydrophobic chromatography on resin such as butyl Sepharose, phenyl Sepharose or the like, gel filtration using molecular sieve, affinity chromatography, chromatofocusing, and electrophoresis such as isoelectric focusing.

If said polypeptide is expressed as an inclusion body in cells, the cells are similarly recovered, disrupted and centrifuged to give a precipitated fraction. From the fraction the polypeptide is then recovered in a usual manner, and the inclusion body of the polypeptide is solubilized with a polypeptide denaturing agent. The solubilized solution is then diluted with or dialyzed against a solution not containing the polypeptide denaturing agent or a solution containing the polypeptide denaturing agent at the low concentration enough not to denature the polypeptide whereby the solubilized polypeptide is renatured to have normal tertiary structure, and its purified preparation can be obtained by use of the same isolation and purification methods as described above.

If said polypeptide is extracellularly secreted, the culture is subjected to means such as centrifugation to give a soluble fraction. From the soluble fraction, a purified preparation of said polypeptide can be obtained in the same manner as for isolation and purification from the cell-free extract as described above.

Furthermore, a method for purifying glycosyltransferases can also be used. The purification method includes e.g. methods used for partial purification of β1,3-N-acetylglucosaminyltransferase [Methods Enzymol., 83, 458 (1982), J. Biol. Chem., 268, 27118 (1993), J. Biol. Chem., 267, 2994 (1992), J. Biol. Chem., 263, 12461 (1988), Jpn. J. Med. Sci. Biol., 42, 77 (1993)].

Furthermore, the polypeptide of the present invention may be produced as a fusion protein with another protein so that it can be purified by affinity chromatography using a substance having affinity for the fused protein. For example, the polypeptide of the present invention is produced as a fusion protein with protein A so that it can be purified by affinity chromatography using immunoglobulin G, according to the method of Lowe et al. [Proc. Natl. Acad. Sci., USA, 86, 8227 (1989), Genes Develop., 4, 1288 (1990)] or methods described in Japanese Published Unexamined Patent Application Nos. 336963/93 and 823021/94. Furthermore, the polypeptide of the present invention is produced as a fusion protein with a Flag peptide so that it can be purified by affinity chromatography using anti-Flag antibody [Proc. Natl. Acad. Sci., USA, 86, 8227 (1989), Genes Develop., 4, 1288 (1990)]. Furthermore, the polypeptide can also be purified by affinity chromatography using an antibody against said polypeptide itself.

If the polypeptide of the present invention possesses β1,3-N-acetylglucosaminyltransferase activity, β1,3-N-acetylglucosaminyltransferase activity can be determined using conventional measurement methods [J. Biol. Chem., 268, 27118 (1993), J. Biol. Chem., 267, 2994 (1992), J. Biol. Chem., 263, 12461 (1988), Jpn. J. Med. Sci. Biol., 42, 77 (1989)].

(3) Production of Glycoproteins, Glycolipids or Oligosaccharides Having poly-N-acetyllactosamine Sugar Chains or Their Modified Sugar Chains Among the transformants capable of producing the polypeptide of the present invention described in item (2) above, the transformants capable of producing sugar chains are cultured in a medium until glycoproteins having poly-N-acetyllactosamine-containing sugar chains, glycolipids having poly-N-acetyllactosamine-containing sugar chains or oligosaccharides containing poly-N-acetyllactosamine are formed and accumulated, and the glycoproteins having poly-N-acetyllactosamine-containing sugar chains, the glycolipids having poly-N-acetyllactosamine-containing sugar chains or the oligosaccharides containing poly-N-acetyllactosamine are recovered from the culture, whereby the glycoproteins having poly-N-acetyllactosamine-containing sugar chains, the glycolipids having poly-N-acetyllactosamine-containing sugar chains or the oligosaccharides containing poly-N-acetyllactosamine can be produced.

The culturing can be conducted according to item (2) above.

Further, if the above transformant expresses a glycosyltransferase gene (e.g. β1,4-galactosyltransferase gene) simultaneously, then glycoproteins, glycolipids or oligosaccharides having poly-N-acetyllactosamine-containing sugar chains can be effectively produced.

Furthermore, the polypeptide of the present invention and a recombinant glycoprotein of interest (e.g. pharmaceutical recombinant protein) are simultaneously produced in a transformant whereby poly-N-acetyllactosamine-containing sugar chains can be added to the recombinant glycoprotein.

Furthermore, if the transformant expresses a glycosyltransferase gene (e.g. β1,4-galactosyltransferase gene) simultaneously, then recombinant glycoproteins having poly-N-acetyllactosamine-containing sugar chains can be effectively produced.

From the glycoproteins, glycolipids or oligosaccharides having poly-N-acetyllactosamine-containing sugar chains produced by the method described above, a part of the oligosaccharides can be cleaved off by conventional enzymatic or chemical means ["Zoku Seikagaku Jikken Koza" (Sequel to Lecture of Experiments in Biochemistry), Vol. 4, "Fukugotoshitsu Kenkyuho I & II" (Method for Study of Complex Carbohydrates), ed. by Japanese Biochemistry Society and published by Tokyo Kagaku Dojin K. K. (1986); N. Taniguchi, A. Suzuki, K. Furukawa, K. Sugawara: Experimental Protocol in Glycobiology, published by Shujunsha (1996)].

If the polypeptide of the present invention is a polypeptide having β1,3-N-acetylglucosaminyltransferase activity, the polypeptide of the present invention, UDP-GlcNAc, and a receptor substrate selected from a glycoprotein having a lactosamine structure (Galβ1-4GlcNAc structure) at the non-reducing terminus of a sugar chain, a glycolipid having the lactosamine structure at the non-reducing terminus of a sugar chain, an oligosaccharide having the lactosamine structure at the non-reducing terminus of a sugar chain and lactose (Galβ1-4Glc) are allowed to be present in an aqueous medium, and a reaction product having N-acetylglucosamine added via a β1,3-linkage to galactose residue present at the terminus of the lactosamine structure of said receptor substrate is formed and accumulated in the aqueous medium, and the reaction product is recovered from the aqueous medium whereby the reaction product having N-acetylglucosamine added via a β1,3-linkage to galactose residue present at the terminus of the lactosamine structure of said receptor substrate can be produced.

Furthermore, the product obtained in aforesaid production process, UDP-Gal and β1,4-galactosyltransferase are allowed to be present in an aqueous medium, and a reaction product having galactose added via a β1,4-linkage to N-acetylglucosamine in the aforesaid product is formed and accumulated in the aqueous medium, and this reaction product is recovered from the aqueous medium whereby the reaction product having galactose added via a β1,4-linkage to N-acetylglucosamine in the aforesaid product can be produced.

Furthermore, the polypeptide of the present invention, UDP-GlcNAc, UDP-Gal, β1,4-galactosyltransferase and a receptor substrate selected from a glycoprotein having the lactosamine structure at the non-reducing terminus of a sugar chain, a glycolipid having the lactosamine structure at the non-reducing terminus of a sugar chain, an oligosaccharide having the lactosamine structure at the non-reducing terminus of a sugar, and lactose, are allowed to be present in an aqueous medium, and a reaction product having a poly-N-acetyllactosamine sugar chain [(Galβ1-4GlcNAcβ1-3)n where n is 2 or more] added to the terminus of the lactosamine structure of said receptor substrate is formed and accumulated in the aqueous medium, and the reaction product is recovered from the aqueous medium whereby the reaction product having the poly-N-acetyllactosamine sugar chain added to the terminus of the lactosamine structure of said receptor substrate can be produced.

As β1,4-galactosyltransferases, an enzyme purified from bovine or human milk (commercially available from Sigma) or a recombinant enzyme (commercially available from Calbiochem) can be used.

Furthermore, by use of an animal or a plant, glycoproteins having poly-N-acetyllactosamine-containing sugar chains, glycolipids having poly-N-acetyllactosamine-containing sugar chains, and oligosaccharides containing poly-N-acetyllactosamine can be produced according to the method described in item (2) above.

That is, in the case of an animal, for example, non-human transgenic animals carrying the DNA of the present invention are raised, and glycoproteins having poly-N-acetyllactosamine-containing sugar chains, glycolipids having poly-N-acetyllactosamine-containing sugar chains or oligosaccharides containing poly-N-acetyllactosamine are formed and accumulated in the animals, and the glycoproteins having poly-N-acetyllactosamine-containing sugar chains, the glycolipids having poly-N-acetyllactosamine-containing sugar chains or the oligosaccharides containing poly-N-acetyllactosamine are recovered from the animal whereby the glycoproteins having poly-N-acetyllactosamine-containing sugar chains, the glycolipids having poly-N-acetyllactosamine-containing sugar chains or the oligosaccharides containing poly-N-acetyllactosamine can be produced. The place where they are formed and accumulated in the animal is for example milk, egg etc. of the animal.

In the case of a plant, for example, transgenic plants carrying the DNA of the present invention are cultured, and glycoproteins having poly-N-acetyllactosamine-containing sugar chains, glycolipids having poly-N-acetyllactosamine-containing sugar chains or oligosaccharides containing poly-N-acetyllactosamine are formed and accumulated in the plant, and the glycoproteins having poly-N-acetyllactosamine-containing sugar chains, the glycolipids having poly-N-acetyllactosamine-containing sugar chains or the oligosaccharides containing poly-N-acetyllactosamine are recovered from the plant whereby the glycoproteins having poly-N-acetyllactosamine-containing sugar chains, the glycolipids having poly-N-acetyllactosamine-containing sugar chains or the oligosaccharides containing poly-N-acetyllactosamine can be produced.

(4) Application of the DNA or Oligonucleotide of the Present Invention to Treatment, Diagnosis etc. of Diseases The DNA of the present invention can be applied to treatment of diseases such as inflammations, cancers etc. by use of antisense RNA/DNA technology [Bioscience and Industry, 50, 322 (1992); "Kagaku" (Chemistry), 46, 681 (1991); Biotechnology, 9, 358 (1992); Trends in Biotechnology, 10, 87 (1992); Trends in Biotechnology, 10, 152 (1992); "Saibo Kogaku" (Cell Engineering), 16, 1463 (1997)] or by use of triple helix technology [Trends in Biotechnology, 10, 132 (1992)] as well as to diagnosis of such diseases by use of Northern hybridization or PCR techniques.

For example, production of the polypeptide of the present invention can be inhibited by administering the oligonucleotide of the present invention described in item (1) above or its derivative.

Furthermore, expression level of DNA coding for the polypeptide of the present invention can be determined by Northern hybridization or PCR using the DNA of the present invention or the above oligonucleotide prepared from the DNA.

A promoter region of said gene can be obtained by using the DNA of the present invention as a probe in a known method ["Shin Saibo Kogaku Jikken Protocol" (New Experimental Protocol in Cell Engineering), edited by Department of Anticancer Research, Medical Research Institute, Tokyo University and published by Shujunsha (1993)].

The promoter region may be any promoter region participating in transcription of the gene coding for the polypeptide of the present invention in mammalian cells. For example, mention can be made of promoter regions participating in transcription of the gene coding for the polypeptide of the present invention in human melanoma cells, human colon cancer cells, or human leukocytes. These promoters can be used in the screening method described below.

(5) Preparation of an Antibody Recognizing the Polypeptide of the Present Invention (i) Preparation of a Polyclonal Antibody Polyclonal antibody can be prepared by using a purified product of the whole length or a partial fragment of the protein obtained by the method described in the above in (2) as the antigen and administering the antigen to animal by subcutaneous, intravenous or intraperitoneal injection together with an appropriate adjuvant (for example, complete Freund's adjuvant, aluminum hydroxide gel, pertussis vaccine, or the like).

The peptide synthesized using a peptide synthesizer and having a partial amino acid sequence of the protein of the present invention can also be used as the antigen.

Examples of the animals used include rabbits, goats, 3- to 20-week-old rats, mice, hamsters and the like.

Preferable dosage of antigen is 50 to 100 μg per animal.

When a peptide is used as the antigen, it is preferred to use the peptide as the antigen after binding it covalently to a carrier protein, such as keyhole limpet haemocyanin, bovine thyroglobulin or the like.

Administration of the antigen is carried out 3 to 10 times at one- to two-week intervals after the first administration. A blood sample is recovered from the fundus of the eye 3 to 7 days after each administration, and the serum is tested, for example, by enzyme immunoassay [Enzyme-linked Immunosorbent Assay (ELISA), published by Igaku Shoin (1976); Antibodies—A Laboratory Manual, Cold Spring Harbor Laboratory (1988)] as to whether it is reactive with the antigen used for immunization.

A polyclonal antibody can be prepared by obtaining the serum from a non-human mammal whose serums shows a sufficient antibody titer against the antigen used for immunization, isolating and purifying it from the serum.

With regard to the method for the isolation and purification of the polyclonal antibody, centrifugation, salting-out method with 40 to 50% saturated ammonium sulfate, caprylic acid precipitation method[Antibodies,A Laboratory manual,Cold Spring Harbor Laboratory, (1988)], or chromatographic methods using a DEAE-Sepharose column, an anion exchange column, a protein A or G column, a gel filtration column and the like may be employed alone or in combination.

(ii) Preparation of a Monoclonal Antibody (a) Preparation of Antibody-producing Cells The non-human mammal whose serum showed adequate antibody titer against a partial fragment of the polypeptide of the present invention used in immunization are used as a source of antibody-producing cells.

On day 3 to 7 after the final administering with the antigen to the non-human mammal with the antibody titer, the spleen is excised from the non-human mammal.

The spleen is cut into pieces in MEM medium (manufactured by Nissui Pharmaceuticals, Co.) and the pieces are then loosened with tweezers, followed by centrifugation at 1,200 rpm for 5 minutes, to discard the resulting supernatant.

The spleen cells in the resulting precipitated fraction are treated with a Tris-ammonium chloride buffer (pH 7.65) for 1 to 2 minutes to remove erythrocytes, followed by washing 3 times with MEM medium to give spleen cells as antibody-producing cells.

(b) Preparation of Myeloma Cells

As myeloma cells, cell lines obtained from mice or rats are used. For example, 8-azaguanine-resistant mice (BALB/c)-derived myeloma cell line P3-X63Ag8-U1 (hereinafter abbreviated to P3-U1) [Curr. Topics. Microbiol. Immunol., 81, 1 (1978), Europ. J. Immunol., 6, 511 (1976)], SP2/0-Ag14 (SP-2) [Nature, 276, 269 (1978)], P3-X63-Ag8653 (653) [J. Immunol., 123, 1548 (1979)], P3-X63-Ag8(X63) [Nature, 256, 495 (1975)] etc. can be used. These cell lines are further subjected to subculture in 8-azaguanine medium [medium prepared by adding 8-azaguanine (15 µg/ml) to a medium (referred to hereinafter as normal medium) having glutamine (1.5 mM), 2-mercaptoethanol ($5 \times 10^{-5}$ M), gentamicin (10 µg/ml) and fetal calf serum (FCS) (a product of CSL Ltd.; 10%) added to RPMI-1640 medium], and 3 to 4 days before cell fusion, they are cultured in the normal medium and at least $2 \times 10^7$ cells are used for fusion.

(c) Preparation of Hybridoma

The antibody-producing cells obtained in item (a) above and myeloma cells obtained in item (b) above are washed well with MEM medium or PBS (1.83 g of disodium phosphate, 0.21 g of monopotassium phosphate, 7.65 g of common salt, 1 L of distilled water, pH 7.2) and mixed such that the ratio of the antibody-producing cells/myeloma cells ranges from 5/1 to 10/1, and these cells are centrifuged at 1,200 r.p.m. for 5 minutes and the supernatant is discharged.

The cell pellet obtained as the precipitated fraction is well loosened, and a mixture containing of 2 g of polyethylene glycol-1000 (PEG-1000), 2 ml of MEM and 0.7 ml of dimethyl sulfoxide (DMSO) is added to the cells in a volume of 0.2 to 1 ml/$10^8$ antibody-producing cells with starring at 37° C., and 1 to 2 ml of MEM medium is added thereto several times at 1- to 2-minute intervals.

After addition, MEM medium is added to adjust the total volume to 50 ml.

The solution thus prepared is centrifuged at 900 r.p.m. for 5 minutes, and the supernatant is discarded.

The cells obtained in the precipitated fraction are gently loosened and suspended by pipetting in 100 ml of HAT medium [the medium prepared by adding hypoxanthine ($10^{-4}$ M), thymidine ($1.5 \times 10^{-5}$ M) and aminopterin ($4 \times 10^{-7}$ M) to the normal medium].

The suspension is divided into 96-well culture plates (100 µl/well) and is cultured at 37° C. in a 5% $CO_2$ incubator for 7 to 14 days.

After culturing, an aliquot of the supernatant is sampled and a hybridoma reacting specifically to a partial fragment of the polypeptide of the present invention is selected by enzyme immunoassays described in e.g. "Antibodies" [Antibodies, A Laboratory Manual, Cold Spring Harbor Laboratory, Chapter 14 (1988)].

Specifically, enzyme immunoassays are conducted as follows:

An appropriate plate is coated with a partial fragment of the polypeptide of the present invention, which was used as an antigen for immunization, followed by reaction with a culture supernatant of the hybridoma or with the purified antibody obtained in (d) below as a first antibody and then with anti-rat or anti-mouse immunoglobulin antibody as a second antibody labeled with biotin, an enzyme, a chemiluminescent substance or a radioisotope. Then, reaction depending on the labeling substance is conducted, and a hybridoma reacting specifically with the polypeptide of the present invention is selected as a hybridoma producing a monoclonal antibody against the polypeptide of the present invention.

Using the hybridoma, cloning is repeated two times by limiting dilution [for first dilution, HT culture medium (aminopterin-free HAT medium) is used; for second dilution, the normal medium is used]. A hybridoma showing a stable and strong antibody titer is selected as the hybridoma producing an antibody against the polypeptide of the present invention.

(d) Preparation of a Monoclonal Antibody

The hybridoma cells producing a monoclonal antibody against the polypeptide of the present invention, obtained in item (c) above, are injected at a dose of $5-20 \times 10^6$ cells/animal into the abdomens of 8 to 10-week-old mice or nude mice treated with 0.5 ml Pristane [animals raised for 2 weeks after intraperitoneal administration of 2,6,10,14-tetramethylpentadecane (Pristane)]. The hybridoma forms ascites tumor in 10 to 21 days.

From the mouse with the ascites tumor, the ascites is collected and centrifuged at 3,000 rpm for 5 minutes, to remove the solid matters from the fluid.

From the resulting supernatant, the monoclonal antibody can be purified and obtained according to the same method in the polyclonal antibody. Further, from the supernatant of the hybridoma which produces the monoclonal antibody, the monoclonal antibody can be purified and obtained according to the same method.

The class and subclass of the antibody are determined using a mouse monoclonal antibody typing kit or a rat monoclonal antibody typing kit. The protein content is determined by the Lowry method or calculated from absorbance at 280 nm.

The class of the antibody means isotype of the antibody, and for example, mention can be made of IgG, IgA, IgM, IgD and IgE in human. The subclass of the antibody means isotype in the class, and for example, mention can be made of IgG1, IgG2a, IgG2b and IgG3 in mouse, and IgG1, IgG2, IgG3 and IgG4 in human.

(6) Use of the Antibody of the Present Invention (a) The antibody of the present invention can be used to detect the polypeptide of the present invention. Specifically, it is used in detection methods such as ELISA/fluorescent antibody techniques using a microtiter plate, Western blotting techniques etc.

(b) The antibody of the present invention can be used for immunostaining of tissues of cells expressing the polypeptide of the present invention.

(c) The antibody of the present invention can be used for diagnosis or treatment of diseases such as inflammations, cancers etc.

(7) Application to Screening Methods

Because the polypeptide of the present invention has poly-N-acetyllactosamine sugar chains synthesis-related activity, a compound enhancing or inhibiting the activity of said polypeptide can be used to increase or decrease the amount of poly-N-acetyllactosamine sugar chains synthesized in cells.

Furthermore, a compound promoting or inhibiting the transcriptional process of a gene coding for said polypeptide or the translational process of the resulting transcript into a protein can regulate expression of said polypeptide to regulate the amount of poly-N-acetyllactosamine sugar chains synthesized in cells.

The above compound is useful for treatment of diseases such as inflammations or cancers or for synthesis of poly-N-acetyllactosamine sugar chains.

The compound can be obtained by the following methods (a) to (e):

(a) The polypeptide of the present invention described in item (2) above, an extract from cells capable of synthesizing poly-N-acetyllactosamine sugar chains, a test sample, UDP-GlcNAc, UDP-Gal, and a sugar chain as an acceptor substrate (a sugar chain having the lactosamine structure at the terminus) are reacted and measured according to known methods [J. Biol. Chem., 268, 27118 (1993); J. Biol. Chem., 267, 2994 (1992); J. Biol. Chem., 263, 12461 (1988); Jpn. J. Med. Sci. Biol., 42, 77 (1989)], whereby a test compound which increased or decreased the amount of the product formed by this reaction is selected and obtained;

(b) If the polypeptide of the present invention is a polypeptide having $\beta$1,3-N-acetylglucosaminyltransferase activity, the polypeptide (a cell extract or a purified polypeptide from the transformant expressing said polypeptide) prepared by the method described in item (2) above is used as the enzyme, and $\beta$1,3-N-acetylglucosaminyltransferase activity is measured in the presence of a test sample by the above-described method, whereby a test compound which increased or decreased $\beta$1,3-N-acetylglucosaminyltransferase activity is selected and obtained;

(c) Cells expressing the polypeptide of the present invention or the transformant described in item (2) above is cultured for 2 hours to 1 week in the presence of a test sample by the culture method described in item (2) above, and then the amount of poly-N-acetyllactosamine sugar chains on cell surface is determined using the anti-i antibody, whereby a test compound which increased or decreased the amount of the sugar chains is selected and obtained;

The measurement method using the anti-i antibody includes e.g. detection methods such as ELISA/fluorescence antibody technique using microtiter plate, Western blotting, immunohistostaining, etc.;

(d) Cells expressing the polypeptide of the present invention are cultured for 2 hours to 1 week in the presence of a test sample by the culture method described in item (2) above, and the amount of said polypeptide in the cells is determined using the antibody of the present invention described in item (5) above, whereby a test compound which increased or decreased the amount of said polypeptide is selected and obtained.

The measurement method using the antibody of the present invention includes e.g. detection methods such as ELISA/fluorescence antibody technique using a micro titer plate, Western blotting, immunostaining etc.;

(e) Cells expressing the polypeptide of the present invention are cultured for 2 hours to 1 week in the presence of a test sample by the culture method described in item (2) above, and then the amount of transcripts produced from the gene coding for said polypeptide in cells is determined by the method described in item (4) above such as Northern hybridization, PCR or the like, whereby a test compound which increased or decreased the amount of the transcripts is selected and obtained; and (f) A plasmid that carries the DNA to which a reporter gene ligated downstream of a promoter obtained in item (4) above is prepared in the known method, and the plasmid is introduced into the animal cells described in item (2) above by use of the method described in item (2) above whereby a transformant is obtained. The transformant is cultured for 2 hours to 1 week in the presence of a test sample by the culture method described in item (2) above, and the expression level of the reporter gene in the cells is determined by the known method ["Shin Saibo Kogaku Jikken Protocol" (New Experimental Protocol in Cell Engineering), edited by Department of Anticancer Research, Medical Research Institute, Tokyo University and published by Shujunsha (1993); Biotechniques, 20, 914 (1996); J. Antibiotics, 49, 453 (1996); Trends in Biochemical Sciences, 20, 448 (1995); "Saibo Kogaku" (Cell Engineering), 16, 581 (1997)], whereby a test compound which increased or decreased the expression level is selected and obtained.

Examples of reporter genes are a chloramphenicol acetyl transferase gene, a $\beta$-galactosidase gene, a luciferase gene, a green fluorescent protein (GFP) gene etc.

EXAMPLES

Examples are shown below. Unless otherwise specified, the known methods described in Molecular Cloning, 2nd edition were used as techniques in genetic manipulation.

Example 1

Cloning of a Gene (cDNA) Which Increase Reactivity with Anti-i Antibody (Den)

(1) Preparation of mRNAs from Human Melanoma Cell Line WM266-4 and Human Colon Cancer Cell Line SW1116

About 30 μg of mRNA was obtained respectively from $1\times10^8$ cells each of human melanoma cell line WM266-4 (ATCC CRL 1676) and human colon cancer cell line SW1116 (ATCC CRL 233) by use of a mRNA extraction kit, Fast Track® (Product No. K1593-02, a product of Invitrogen). Specific reagents and method followed instructions attached to the kit.

(2) Construction of cDNA Libraries of WM266-4 and SW1116

Eight micrograms each of the mRNAs derived from WM266-4 and SW1116, obtained in item (1) above, and a cDNA synthesis system kit (Gibco BRL) were used to synthesize double-stranded cDNA by use of oligo-dT as a primer. However, the reverse transcriptase used was not the moloney murine leukemia virus (M-MLV) reverse transcriptase contained in the kit but Super Script™ RNase H-reverse transcriptase available from the same manufacture.

Sfi I linkers were added to both terminus of these double-stranded cDNAs in the following manner.

[Addition of Sfi I Linkers]

The single-stranded DNA shown in SEQ ID NO:3 and the single-stranded DNA shown in SEQ ID NO:4 were synthesized by 380A•DNA synthesizer (Applied Biosystems).

Each of the synthesized single-stranded DNAs (50 μg) was separately dissolved in 50 μl of buffer containing 50 mM Tris-HCl buffer (pH 7.5), 10 mM $MgCl_2$, 5 mM dithiothreitol (abbreviated hereinafter to DTT), 0.1 mM EDTA and 1 mM ATP (this buffer is referred hereinafter to T4 kinase buffer), followed by addition of 30 U of T4 polynucleotide kinase (Takara Shuzo Co., Ltd.) to allow phosphorylation reaction at 37° C. for 16 hours whereby 11-bp and 8-bp linkers were obtained respectively.

Four micrograms of the 11-bp linker, 2.9 μg of the 8-bp linker and the double-stranded cDNAs synthesized above were dissolved in 45 μl of T4 ligase buffer, and 1050 U of T4 DNA ligase was added thereto followed by reaction at 16° C. for 16 hours, and the Sfi I linkers were added to each of the double-stranded cDNAs.

The resulting reaction mixture were subjected to agarose gel electrophoresis and about 1.6-kb or more DNA fragments were recovered respectively.

Eight micrograms of the mRNA derived from WM266-4 obtained above was used to synthesize double-stranded cDNA by use of a cDNA synthesis system kit (Gibco BRL) with random primers as primers. The reverse transcriptase used in this synthesis reaction was Super Script™ RNase H-reverse transcriptase (Gibco BRL).

After Sfi I linkers were added to both terminus of the cDNA in the same manner as described above, it was subjected to agarose gel electrophoresis and about 1.2-kb or more DNA fragments were recovered.

Twenty-four micrograms of expression cloning vector pAMo [J. Biol. Chem., 268, 22782 (1993), also called pAMoPRC3Sc (Japanese Published Unexamined Patent Application No. 336963/93)] was dissolved in 590 μl of buffer containing 10 mM Tris-HCl (pH 7.5), 6 mM $MgCl_2$, 50 mM NaCl and 6 mM 2-mercaptoethanol (this buffer is referred to hereinafter as Y-50 buffer), and 80 U of restriction enzyme Sfi I (a product of Takara Shuzo Co., Ltd.; all restriction enzymes used hereinafter are products of Takara Shuzo Co., Ltd. unless otherwise specified) was added to allow digestion reaction at 37° C. for 16 hours.

Forty units of Bam HI was added to the reaction mixture, followed by digestion reaction at 37° C. for 2 hours.

The reaction mixture was subjected to agarose gel electrophoresis, and about 8.8-kb DNA fragments were recovered.

Each of the three kinds of DNAs prepared above (each derived from 8 μg of mRNA) having Sfi I linkers added thereto was separately dissolved in 250 μl of T4 ligase buffer, and to each mixture were added 2 μg of about 8.8-kb DNA fragments obtained above and 2000 U of T4 DNA ligase, followed by ligation reaction at 16° C. for 16 hours.

After the reaction, 5 μg of transfer RNA (tRNA) was added to each reaction mixture, and the sample was precipitated with ethanol and obtained precipitate was dissolved in 20 μl of buffer containing 10 mM Tris-HCl buffer (pH 8.0) and 1 mM EDTA (sodium ethylenediamine tetraacetate) (this buffer is referred to hereinafter TE buffer).

The reaction solution was used to transform E. coli LE392 (Molecular Cloning, 2nd edition) by the electroporation method [Nucleic Acids Res., 16, 6127 (1988)], and about 260,000 ampicillin-resistant transformants were obtained using the DNA derived from WM266-4 with the oligo-dT primer, about 300,000 ampicillin-resistant transformants were obtained using the DNA derived from WM266-4 with the random primer, and about 480,000 ampicillin-resistant transformants were obtained using the DNA derived from SW1116 with the oligo-dT primer, to prepare cDNA libraries derived from the respective DNAs.

(3) Cloning of the Gene (cDNA) which Increase Reactivity with Anti-i Antibody (Den)

A plasmid for each cDNA library obtained in item (2) above was prepared using a plasmid maxi kit (Product No. 41031), that is, a plasmid preparation kit produced by Qiagen.

These plasmids were precipitated with ethanol and dissolved at a concentration of 1 μg/μl in TE buffer.

The plasmid solution was used to introduce the plasmids by the lipofection method into Namalwa cells (Namalwa KJM-1 cells) that were adapted to serum-free medium culturing [Cytotechnology, 1, 151 (1988)]. For introduction of the plasmid, lipofectin (Gibco BRL) was used according to the lipofection method described in the manufacture's instructions. The serum-free medium used in this method was penicillin- and streptomycin-free RPMI1640 ITPSGF medium [RPMI1640 medium (Nissui Seiyaku K. K.) containing a 1/40 volume of 7.5% $NaHCO_3$, 3% of 200 mM L-glutamine solution (Gibco), 0.5% of penicillin/streptomycin solution (5000 units/ml penicillin, 5000 μg/ml streptomycin, produced by Gibco), N-2-hydroxyethylpiperazine-N'-2-ethanesulfonic acid (HEPES) (10 mM), insulin (3 μg/ml), transferrin (5 μg/ml), sodium pyruvate (5 mM), sodium selenite (125 nM), and galactose (1 mg/ml)].

Specifically, 3.25 μl of lipofectin and 2 μg of plasmid were added to 0.8 ml of the cell suspension ($1.0 \times 10^6$ cells/ml) in the penicillin- and streptomycin-free RPMI1640 ITPSGF medium and the cells were cultured overnight in a $CO_2$ incubator (37° C.).

After culturing, 6.5 ml of PRMI1640 ITPSGF medium was added thereto, and the cells were further cultured for 2 days, and then 10-fold excess RPMI1640 ITPSGF medium and G418 (final concentration of 0.5 mg/ml, Gibco BRL) were added thereto, followed by further culturing for 10 days to give stably trans.

By this method, about 33 μg of the plasmid for the cDNA library derived from WM266-4 using the oligo-dT primer, about 39 μg of the plasmid for the cDNA library derived from WM266-4 using the random primer, and about 60 μg of the plasmid for the cDNA library derived from SW1116 using the oligo-dT primer were introduced respectively into Namalwa KJM-1 cells to give stably transformed cells.

The resulting transformed cells for each library were mixed and then subjected to indirect fluorescence antibody staining with anti-i antibody (Den) recognizing linear poly-N-acetyllactosamine sugar chains [J. Biol. Chem., 254, 3221 (1979)]. The method specifically described is as follows:

About $4 \times 10^7$ stably transformed cells were placed in a 50-ml centrifuge tube (2059 tubes, Falcon Co., Ltd.) and the cells were collected by centrifugation (130×g, 10 minutes).

The cells were washed with 20 ml of phosphate buffer solution (A-PBS) containing 0.1% sodium azide (A-PBS: 8 g/l NaCl, 0.2 g/l KCl, 1.15 g/l $Na_2HPO_4$ (anhydride), 0.2 g/l $KH_2PO_4$, 0.1% sodium azide).

The washed cells were suspended in 0.5 ml of anti-i antibody (Den) previously diluted 100-fold with A-PBS, followed by reaction at 4° C. for 1 hour.

After the reaction, the cells were washed once with 20 ml of A-PBS and were suspended in 300 μl of a solution which was prepared by diluting anti-human IgM antibody labeled with fluorescein isothiocyanate (FITC) (a product of DAKO) 30-fold with A-PBS, followed by reaction at 4° C. for 30 minutes.

After the reaction, the cells were washed once with A-PBS and were suspended in 1 ml of A-PBS, and those cells (2.8%) with high fluorescence intensity were aseptically separated and recovered by a fluorescence activated cell sorter (EPICS Elite Flow Cytometer manufactured by COULTER) (FIG. 1).

After the recovered cells were cultured and proliferated in PRMI1640 ITPSGF medium containing 0.5 mg/ml G418, those cells with high fluorescence intensity were aseptically separated and recovered in the same procedure as described above. By repeating this procedure again, those cells with high fluorescence intensity were separated and concentrated.

Those cells (1.3%) with high fluorescence intensity were separated and recovered in the second procedure and those cells (1.1%) with high fluorescence intensity in the third procedure (FIG. 1).

Thus, the cells with increased fluorescence intensity, that is, the cells with increased expression of linear poly-N-acetyllactosamine sugar chains were obtained by the above separation procedures (see FIG. 1).

The cells were cultured in RPMI1640 ITPSGF medium containing 0.5 mg/ml G418, and plasmids were recovered from about $2 \times 10^6$ cells by Hirt method [Mol. Cell. Biol., 8, 2837 (1988)].

The plasmids were introduced into *E. coli* MC1061A by the electroporation method [Nucleic Acids Res., 16, 6127 (1988)] whereby ampicillin-resistant transformants were obtained.

From the 75 transformants, plasmids were isolated by use of Automatic Plasmid Isolation System PI-100 (KURABO) and each plasmid was cleaved with restriction enzymes (Hind III and Asp 718) to examine the structure of the cDNA insert therein.

As a result, the resulting plasmids were classified into 18 types.

The 18 types of plasmids were extracted with phenol/chloroform (1:1), precipitated with ethanol, and dissolved in 10 μl of TE buffer, and each plasmid was introduced into Namalwa KJM-1 cells by the electroporation method [Cytotechnology, 3, 133 (1990)].

That is, 3 μl of the plasmid prepared above or 4 μg of pAMo (control plasmid) was introduced into $1.0$-$1.6 \times 10^6$ cells (200 μl), which were then suspended in 8 ml of RPMI1640 ITPSGF medium and were cultured at 37° C. for 24 hours in a $CO_2$ incubator.

After culturing, G418 (Gibco BRL) was added thereto at a concentration of 0.5 mg/ml, and the cells were further cultured for 10 to 14 days to give transformed cells.

Figure 2:
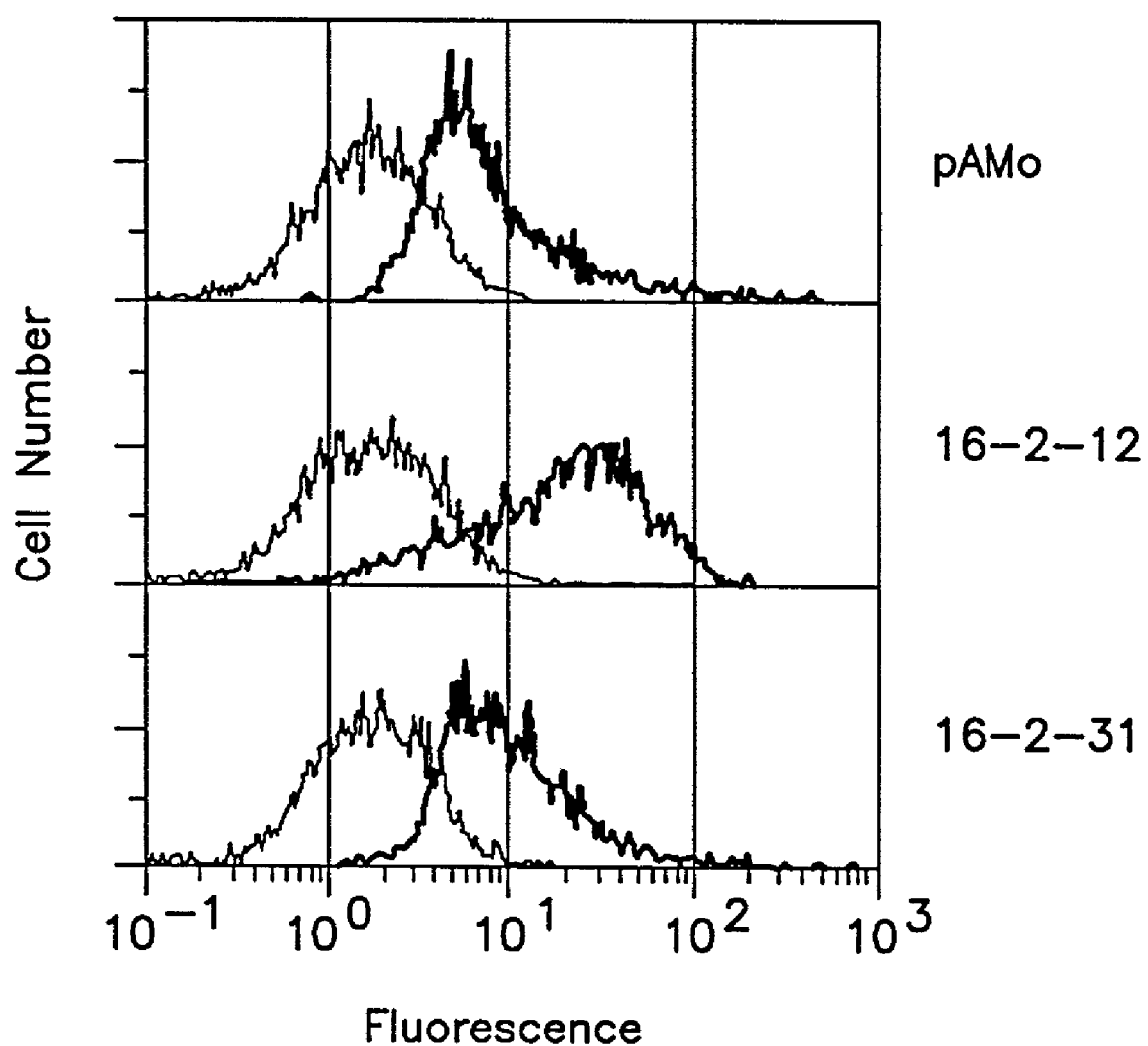
FIG. 2 shows the result of FACS analysis for Namalwa KJM-1 cells which were transformed with plasmids (16-2-12 and 16-2-31) recovered from the cells showing high reactivity with the anti-i antibody and control plasmid pAMo, respectively and were then subjected to indirect fluorescence staining with the anti-i antibody (thick line) or A-PBS (thin line).

When the resulting transformed cells were subjected to indirect fluorescence antibody staining with anti-i antibody (Den), the cells to which the plasmid designated as 16-2-12 had been introduced showed about 7-times higher reactivity (at peak level in a histogram) with the anti-i antibody (Den) than the cells having pAMo introduced therein (FIG. 2). On the other hand, the cells having the other plasmids introduced therein showed almost similar reactivity to that of the cells having the control plasmid (pAMo) introduced therein (FIG. 2).

From the results, it was revealed that the reactivity of the transformed cells to the anti-i antibody (Den) was increased by the cDNA insert in plasmid 16-2-12.

Indirect fluorescence antibody staining with the anti-i antibody (Den) was conducted in the following manner.

About $1 \times 10^6$ transformed cells were placed in a microtube (1.5-ml Eppendorf tube) and centrifuged (550×g, 7 minutes) to collect the cells.

The cells were washed with 0.9 ml of A-PBS, and the washed cells were suspended in 20 μl of anti-i antibody (Den) diluted 100-fold with A-PBS, followed by reaction at 4° C. for 1 hour.

After the reaction, the cells were washed once with 0.9 ml of A-PBS and were suspended in 20 μl of a solution which was prepared by diluting anti-human IgM antibody labeled with FITC (DAKO) 30-fold with A-PBS, followed by reaction at 4° C. for 30 minutes.

After reaction, the cells were washed once with 0.9 ml of A-PBS, then suspended in 0.6 ml of A-PBS and analyzed by a fluorescence activated cell sorter (FACSC aliber available from Becton Dickinson Immunocytometry Systems USA). As a control experiment, the same anlysis was performed using A-PBS in place of the anti-i antibody (Den)(FIG. 2, thin line).

(4) Sequencing of the cDNA Insert in Plasmid 16-2-12

After a restriction enzyme map of the cDNA insert in plasmid 16-2-12 obtained in item (3) above was prepared, DNA fragments derived from this cDNA were subcloned into pBluescript II SK(+), and the whole nucleotide sequence of this cDNA was determined.

Figure 3:
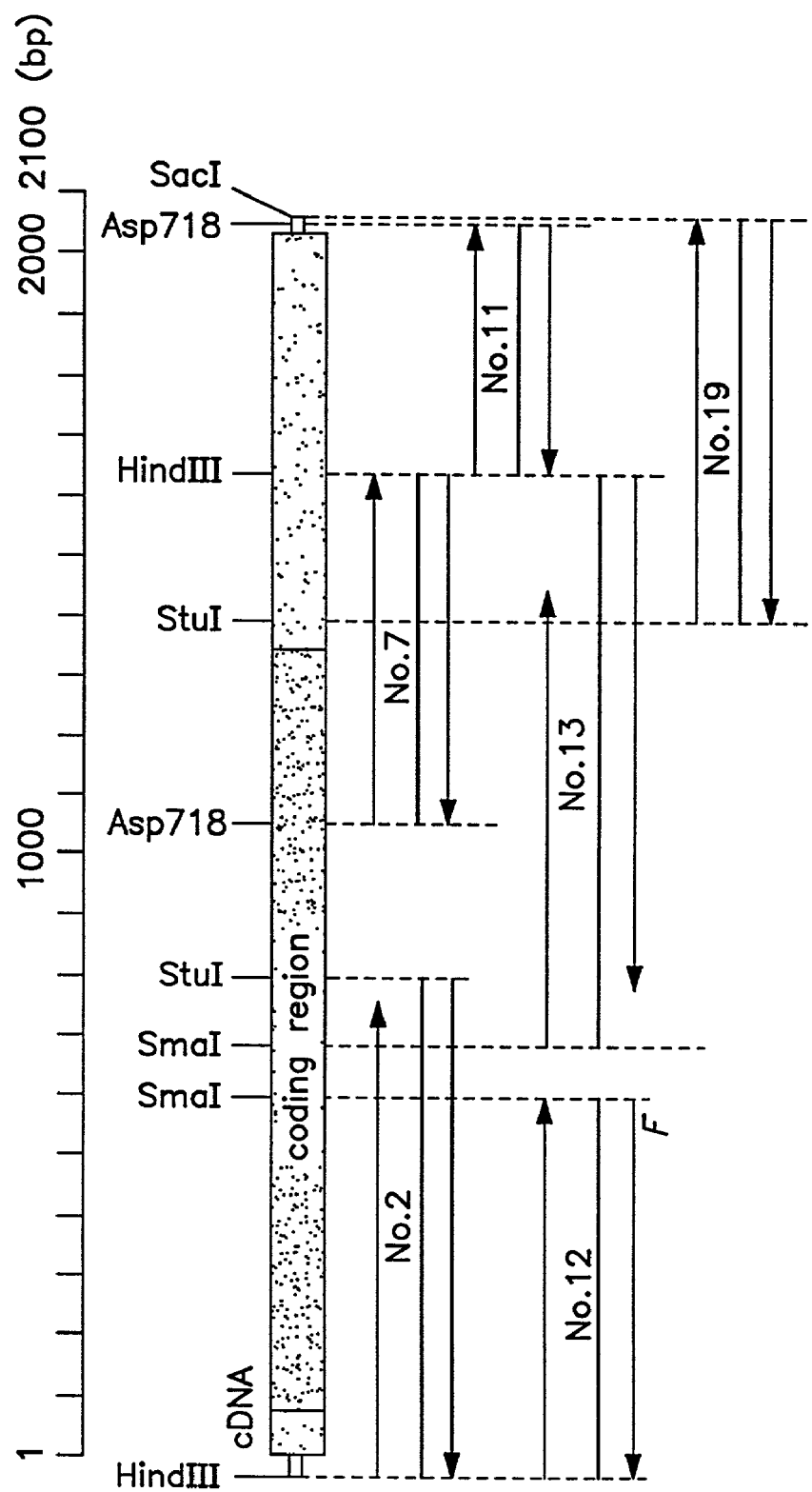
FIG. 3 is a restriction enzyme map of the cDNA insert and regions thereabound (thick lines) in plasmid 16-2-12. The bars with numbers show DNA fragments subcloned into pBluescript IISK(+) to determine the nucleotide sequence of the cDNA. For details, see the text.

That is, plasmid 16-2-12 was prepared using plasmid maxi kit (Product No. 41031) which is a plasmid preparation kit, which produced by Qiagen, and the plasmid was cleaved with various restriction enzymes whereby a restriction enzyme map of the cDNA insert in this plasmid was prepared. The result is shown in FIG. 3.

A Hind III-Stu I fragment (about 0.8 kb: fragment No. 2 in FIG. 3) and a Hind III-Sma I fragment (about 0.6 kb: fragment No. 12 in FIG. 3) were isolated from plasmid 16-2-12 and were subcloned between Hind III-Hinc II sites in pBluescript II SK(+). Furthermore, a Hind III-Sma I fragment (about 1.0 kb: fragment No. 13 in FIG. 3) was isolated from plasmid 16-2-12 and were subcloned between Hind III-Hinc II sites inBluescript II SK(+). Furthermore, a Hind III-Asp 718 fragment (about 0.6 kb: fragment No. 7 in FIG. 3) and a Hind III-Asp 718 fragment (about 0.4 kb: fragment No. 11 in FIG. 3) were isolated from plasmid 16-2-12 and were subcloned between Hind III-Asp 718 sites in pBluescript II SK(+). Furthermore, a Stu I-Sac I fragment (about 0.7 kb: fragment No. 19 in FIG. 3) was isolated from plasmid 16-2-12 and were subcloned between Sac I-Hinc II sites in pBluescript II SK(+).

The nucleotide sequences of the cDNA fragments in the six subcloned plasmids thus constructed were determined using these plasmids as templates by DNA sequencer 377 (Perkin Elmer). For nucleotide sequencing, a kit available from Perkin Elmer was used according to instructions attached to the kit. By combining the results, the whole nucleotide sequence (2011 bp) of the cDNA insert in plasmid 16-2-12 was determined.

The nucleotide sequence of the cDNA is shown in SEQ ID NO:2.

This cDNA codes for a polypeptide consisting of 415 amino acids having a structure characteristic of glycosyltransferase. This polypeptide has no homology to the amino acid sequences of any known proteins. The amino acid sequence of this polypeptide is shown in SEQ ID NO:1.

It is estimated that this polypeptide has a structure in which N-terminal 8 amino acids are located in cytoplasm, subsequent hydrophobic region consisting of 28 amino acids spans membrane, and a large C-terminal region (containig a catalytic domain) is placed in the lumen of the Golgi body.

Hereinafter, said cDNA is referred to as iGnT cDNA, and a protein encoded by said cDNA is referred to as iGnT.

Example 2

Figure 4:
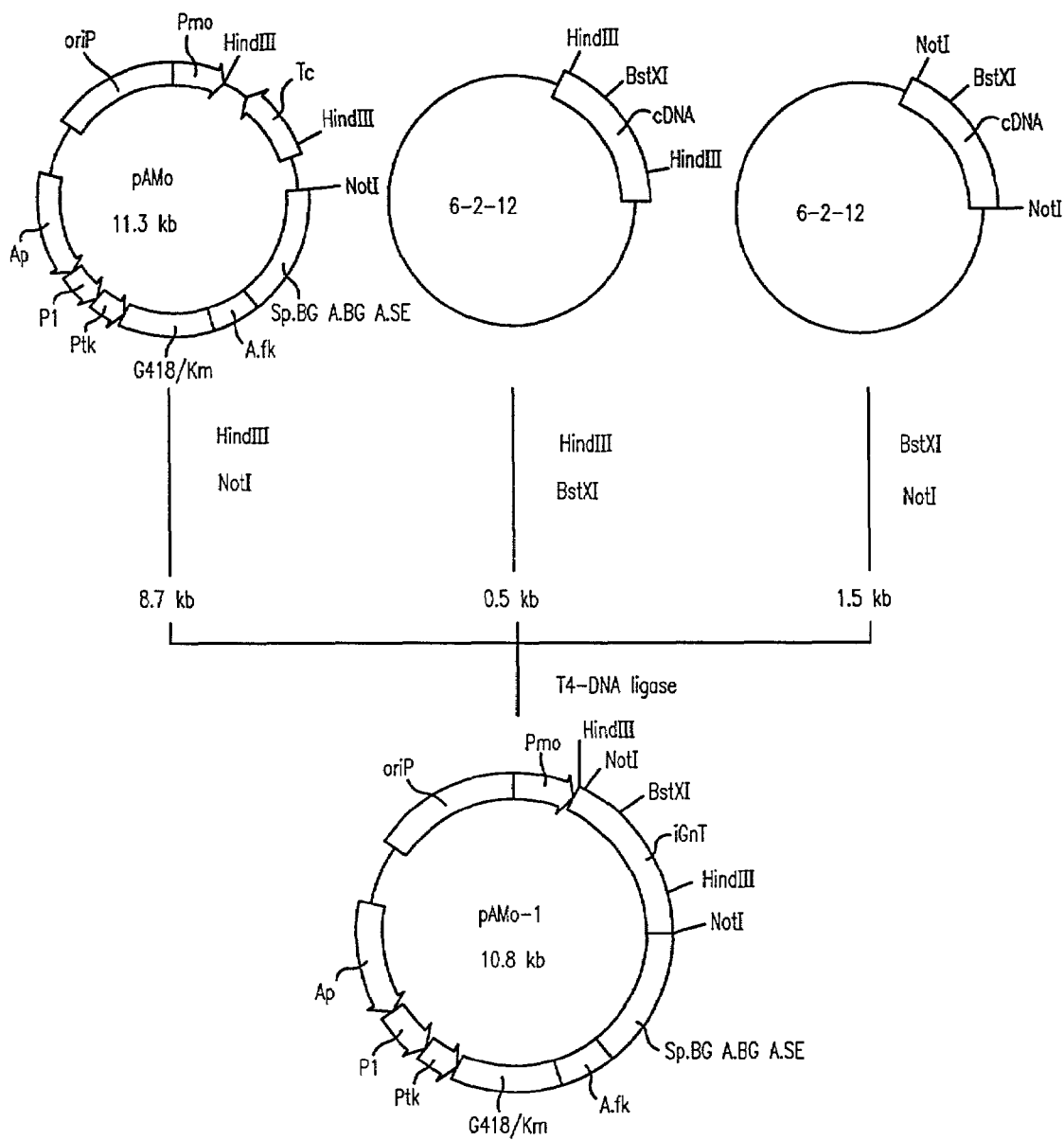
FIG. 4 shows the step of constructing plasmid pAMo-i.

Synthesis of Poly-N-acetyllactosamine Sugar Chains in Namalwa KJM-1 Cells into which an Expression Plasmid for iGnT cDNA Obtained in Example 1 was Introduced (1) Construction of Plasmid pAMo-i for Expression of iGnT cDNA in Animal Cells (FIG. 4)

One microgram of pAMo was dissolved in 20 µl of Y-50 buffer, then 20 U of Hind III was added, followed by digestion reaction at 37° C. for 2 hours.

After reaction, NaCl was added at a concentration of 150 mM and 20 U of Not I was added, followed by further digestion reaction at 37° C. for 2 hours. After the reaction mixture was subjected to agarose gel electrophoresis, about 8.7-kb Hind III-Not I-treated DNA fragment was recovered.

One microgram of plasmid 16-2-12 obtained in Example 1 was dissolved in 20 µl of Y-50 buffer, and 20 U of Hind III was added, followed by digestion reaction at 37° C. for 2 hours.

After reaction, NaCl was added at a concentration of 150 mM, and 20 U of Bst XI was added followed by further digestion reaction at 37° C. for 2 hours. After the reaction mixture was subjected to agarose gel electrophoresis, about 0.5-kb Hind III-Bst XI-treated DNA fragment was recovered.

Furthermore, plasmid 16-2-12 (1 µg) was dissolved in 30 µl of 10 mM Tris-HCl buffer (pH 7.5) containing 6 mM MgCl$_2$, 150 mM NaCl, 6 mM 2-mercaptoethanol (this buffer is referred to hereinafter as Y-150 buffer), and 20 U each of Bst XI and Not I were added, followed by digestion reaction at 37° C. for 2 hours. After the reaction mixture was subjected to agarose gel electrophoresis, about 1.5-kb Bst XI-Not I-treated DNA fragment was recovered.

The resulting 0.02 µg of about 8.7-kb Hind III-Not I-treated DNA fragment, 0.02 µg of about 0.5-kb Hind III-Bst XI-treated DNA fragment and 0.05 µg of about 1.5-kb Bst XI-Not I-treated DNA fragment were dissolved in 20 µl of T4 ligase buffer, and 175 U of T4 DNA ligase was added thereto followed by ligation reaction at 12° C. for 16 hours.

The reaction mixture was used to transform *E. coli* MM294 by the method of Cohen et al. whereby ampicillin-resistant transformants were obtained.

From the transformants, a plasmid was isolated in a usual manner and its structure was confirmed by digestion with restriction enzymes. This plasmid is hereinafter referred to as pAMo-i (FIG. 4).

Figure 5:
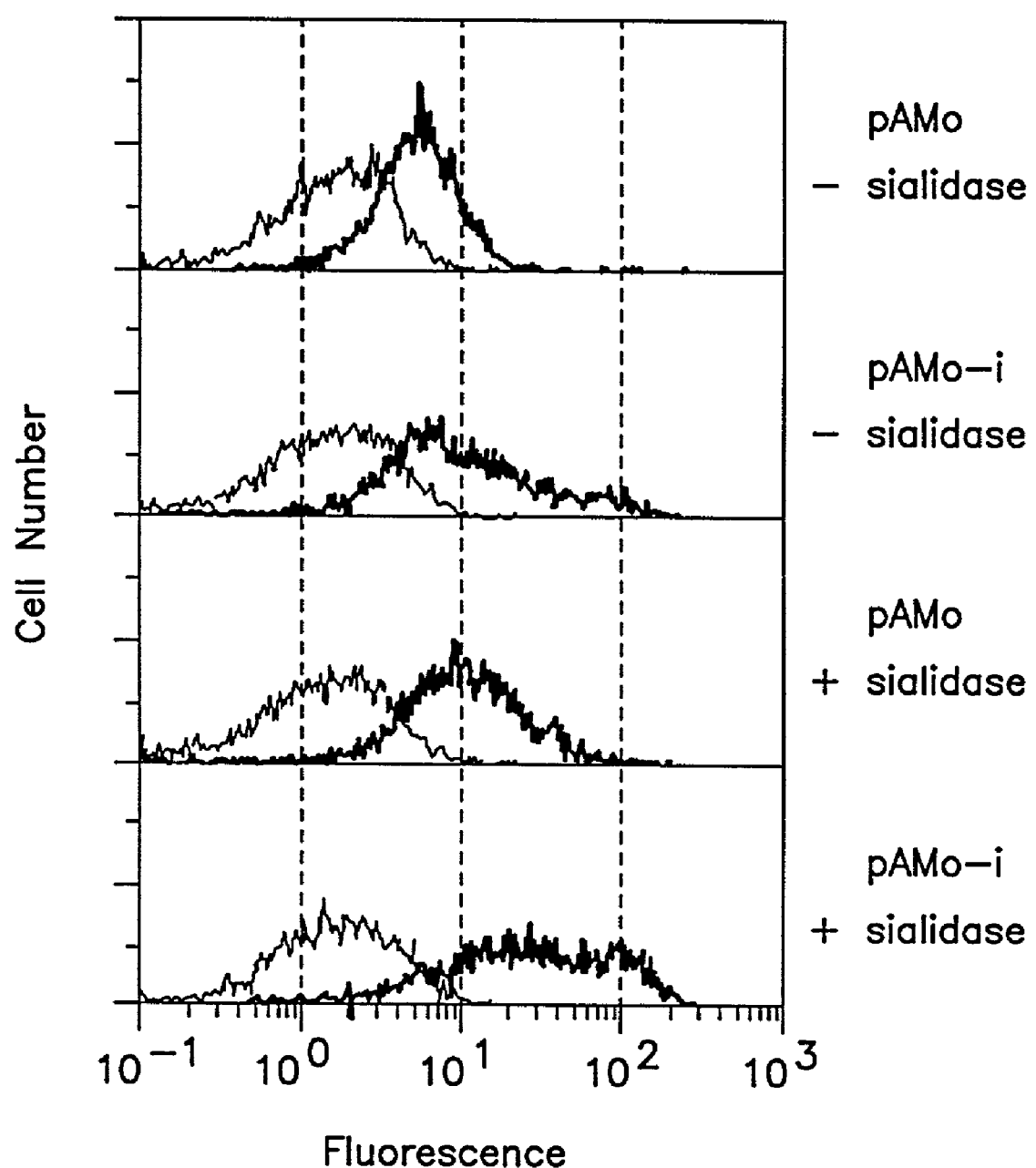
FIG. 5 shows the result of FACS analysis for Namalwa KJM-1 cells which were transformed with iGnT expression plasmid pAMo-i and control plasmid pAMo, respectively and were then subjected to indirect fluorescence staining with anti-i antibody (thick line) or A-PBS (thin line). The reactivity was compared between cells treated with sialidase (+sialidase) before indirect fluorescence antibody staining and non-treated cells (-sialidase).

(2) Synthesis of poly-N-acetyllactosamine Sugar Chains in Namalwa KJM-1 Cells into Which pAMo-i Was Introduced (FIG. 5)

Plasmids pAMo and pAMo-i were dissolved at a concentration of 1 µg/µl respectively in TE buffer and then introduced into Namalwa KJM-1 cells by the lipofection method described in item (3) in Example 1 to give transformed cells.

It is considered that the anti-i antibody (Den), that is, an antibody recognizing linear poly-N-acetyllactosamine sugar chains, hardly recognizes poly-N-acetyllactosamine sugar chains having sialic acid added to the non-reducing terminus thereof [Roelcke et al.: Vox Sanguinis, 48, 181-183 (1985)].

Hence, after the terminal sialic acids were removed by treating the above transformed cells with sialidase, expression of linear poly-N-acetyllactosamine sugar chains on these cells was examined by indirect fluorescence staining with the anti-i antibody (Den).

Namalwa KJM-1 cells ($5 \times 10^6$ cells) into which plasmid pAMo-i or control plasmid pAMo had been introduced were suspended in 100 µl of PBS containing 20 mU neuraminidase (N 2133, Sigma) from *Clostridium perfringens* and were reacted at 37° C. for 1 hour whereby the transformant were treated with sialidase (+sialidase). The control cells were prepared by reaction in neuraminidase-free PBS at 37° C. for 1 hour (−sialidase).

These about $1 \times 10^6$ cells were examined for their expression of linear poly-N-acetyllactosamine sugar chains by indirect fluorescence antibody staining with the anti-i antibody (Den) or A-PBS.

Indirect fluorescence antibody staining was conducted according to the method described in item (3) in Example 1. The results are shown in FIG. 5.

The Namalwa KJM-1 cells transformed with pAMo-i or control plasmid pAMo showed increased reactivity with the anti-i antibody after sialidase treatment, indicating that these transformed cells expressed linear poly-N-acetyllactosamine sugar chains having sialic acids at non-reducing terminus.

In the Namalwa KJM-1 cells transformed with plasmid pAMo, the fluorescence intensity (FIG. 5, thick line) of the cells stained with the anti-i antibody (Den) was stronger than the fluorescence intensity (FIG. 5, thin line) of the control cells stained with A-PBS, demonstrating that Namalwa KMJ-1 cells originally expressed linear poly-N-acetyllactosamine sugar chains.

On the other hand, the Namalwa KJM-1 cells transformed with pAMo-i showed higher reactivity with the anti-i antibody (Den), regardless of whether they were treated with sialidase or not, than that of the Namalwa KJM-1 cells transformed with control plasmid pAMo.

This means that by expressing iGnT cDNA in Namalwa KJM-1 cells, linear poly-N-acetyllactosamine sugar chains are newly synthesized on glycoproteins or glycolipids on cell surface, and it is understood that linear poly-N-acetyllactosamine sugar chains can be newly synthesized even on sugar chains of glycoproteins secreted from cells expressing iGnT cDNA.

These results indicate that by secreting and producing useful glycoproteins using cells expressing the cDNA as a host, poly-N-acetyllactosamine-containing sugar chains can be added to the secreted and produced glycoproteins.

Example 3

Figure 6:
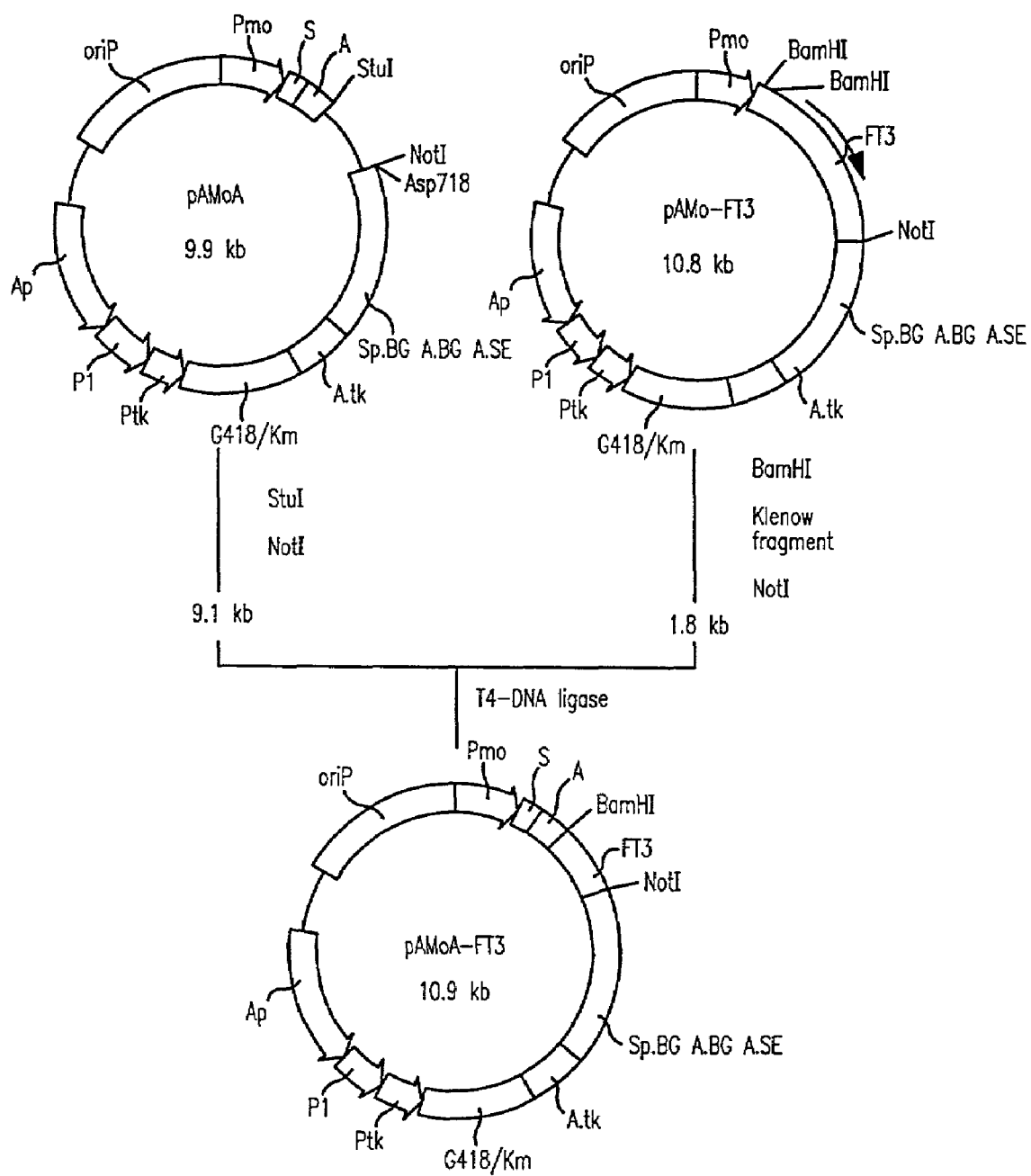
FIG. 6 shows the step of constructing plasmid pAMoA-FT3.
Figure 7:
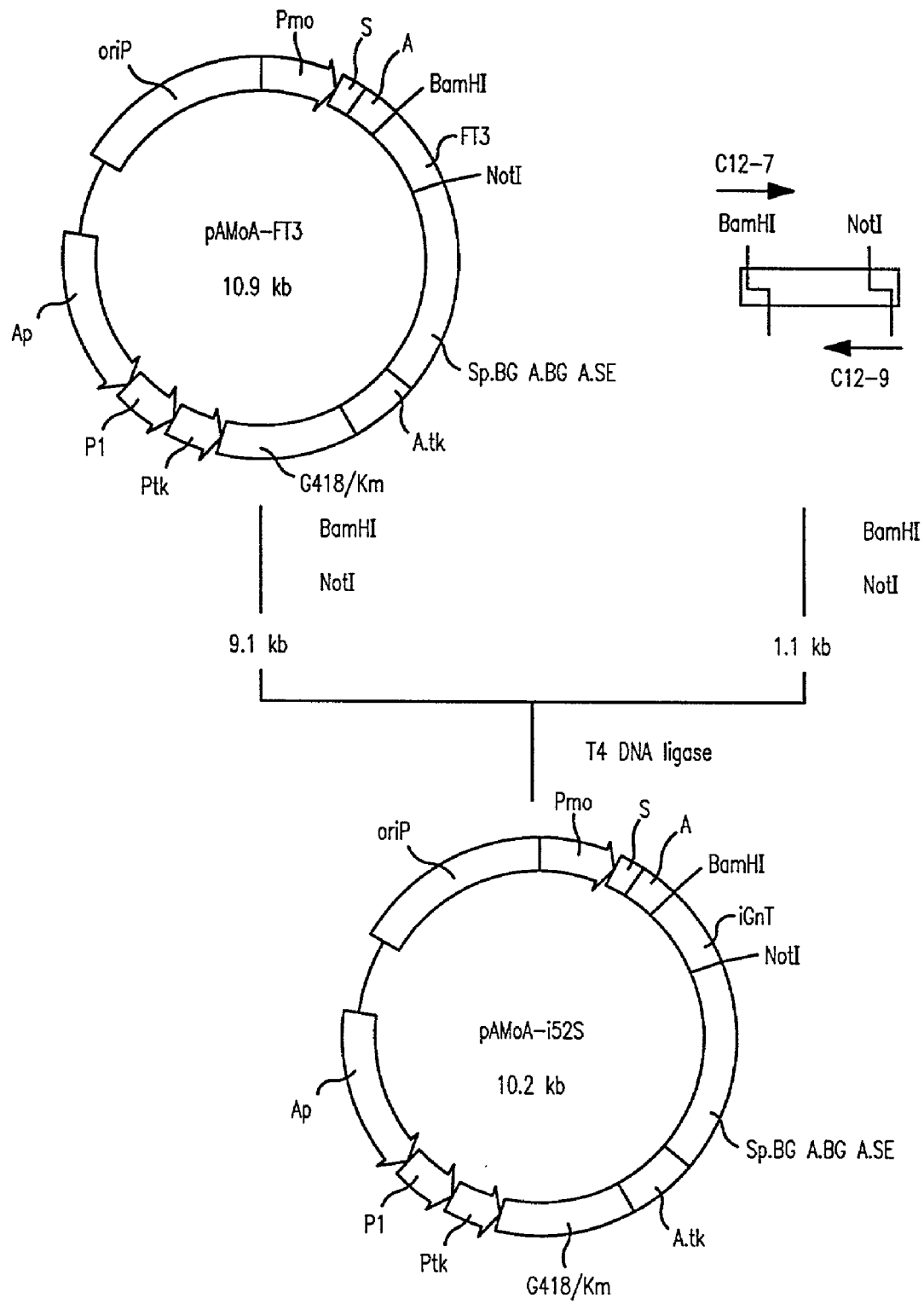
FIG. 7 shows the step of constructing plasmid pAMoA-i52S.

Secretory Production of Protein A-fused iGnT by Namalwa KJM-1 Cells as Host (1) Construction of Plasmid pAMoA-i52S for Secretory Expression of iGnT (FIGS. 6 and 7)

It was estimated from the primary sequence of cloned iGnT that iGnT consists of an N-terminal region (8 amino acids) located in cytoplasm, a subsequent membrane-binding region (28 amino acids) and a C-terminal region (379 amino acids) having catalytic activity. Hence, secretory expression of iGnT was attempted by replacing the N-terminal region located in cytoplasm and the membrane-binding region by a signal sequence of human granular colony stimulating factor and an IgG-binding domain of protein A from *Staphylococcus aureus*.

The region of DNA coding for a region [from Ser 52 to Cys 415 in SEQ ID NO:1] estimated to have catalytic activity was prepared by PCR. Then, a Fuc-TIII gene in pAMoA-FT3, which was a plasmid for secretory expression of α1,3-fucosyltransferase (Fuc-TIII) described below, was replaced by the above DNA encoding putative catalytic domain of iGnT to construct a plasmid pAMoA-i52S for secretory expression of iGnT.

Plasmid pAMoA-FT3 was constructed in the following manner (FIG. 6).

pAMoA (1 µg) was dissolved in 20 µl of buffer containing 10 mM Tris-HCl buffer (pH 7.5), 6 mM $MgCl_2$, 100 mM NaCl and 6 mM 2-mercaptoethanol (this buffer is hereinafter referred to as Y-100), and 20 U of Stu I was added thereto followed by digestion reaction at 37° C. for 2 hours.

After reaction, NaCl was added at a concentration of 150 mM, and 20 U of Not I was added followed by digestion reaction at 37° C. for 2 hours.

After the reaction mixture was subjected to agarose gel electrophoresis, about 9.1-kb Stu I-Not I-treated DNA fragment was recovered.

Separately, 2 µg of pAMo-FT3 [Sasaki et al.: J. Biol. Chem., 269, 14730-14737 (1994)] was dissolved in 20 µl of Y-100 buffer, and 20 U of Bam HI was added followed by digestion reaction at 37° C. for 2 hours.

After reaction, the fragment was precipitated with ethanol, and the resulting precipitate was dissolved in 30 µl of DNA polymerase I buffer, and 6 U of *E. coli* DNA polymerase I Klenow fragment was added thereto followed by reaction at 37° C. for 60 minutes whereby 5'-protruding ends generated by Bam HI digestion were converted to blunt ends.

The reaction was terminated by phenol extraction, and after chloroform extraction and ethanol precipitation, the precipitate was dissolved in 30 µl of Y-150 buffer, and 20 U of Not I was added thereto, followed by digestion reaction at 37° C. for 2 hours.

After the reaction mixture was subjected to agarose gel electrophoresis, about 1.8-kb Bam HI (blunt-ended)-Not I fragment was recovered.

The resulting 0.05 µg of about 9.1-kb Stu I-Not I fragment and 0.05 µg of about 1.8-kb Bam HI (blunt-ended)-Not I fragment were dissolved in 20 µl of T4 ligase buffer, and 175 U of T4 DNA ligase was added thereto, followed by ligation reaction at 12° C. for 16 hours.

The reaction mixture was used to transform *E. coli* MM294 by the method of Cohen et al. whereby ampicillin-resistant transformants were obtained.

From the transformants, a plasmid was isolated in a usual manner and its structure was confirmed by digestion with restriction enzymes. This plasmid was designated as pAMoA-FT3.

Plasmid pAMoA-i52S for secretory expression of iGnT was constructed in the following manner (FIG. 7).

As PCR primers, DNA shown in SEQ ID NO:5 (referred to hereinafter as C12-7) and DNA shown in SEQ ID NO:6 (referred to hereinafter as C12-9) were synthesized (these are also available from Sawaday Technology).

Because C12-7 and C12-9 are designed to have Bam HI and Not I sites, respectively, the DNA fragments amplified by PCR can be inserted between Bam HI and Not I sites in pAMoA-FT3 after digestion with Bam HI and Not I.

PCR was conducted using a kit (GeneAmp™ DNA Amplification Reagent Kit with AmpliTaq™ Recombinant Taq DNA polymerase) manufactured by Takara Shuzo Co., Ltd. A reaction mixture was prepared according to instructions attached to the kit. Perkin Elmer Cetus' DNA Thermal Cycler sold by Takara Shuzo Co., Ltd. was used to perform 10-cycle reaction each cycle consisting of reaction at 94° C. for 30 seconds, at 65° C. for 1 minute, and at 72° C. for 2 minutes, followed by further reaction at 72° C. for 7 minutes. As a template, 10 ng of plasmid pAMo-i constructed in Example 2 was used.

After reaction, the reaction mixture was extracted with chloroform and precipitated with ethanol, and the precipitate was dissolved in 30 µl of Y-150 buffer, and 20 U each of Bam HI and Not I were added thereto, followed by digestion reaction at 37° C. for 3 hours.

After the reaction mixture was subjected to agarose gel electrophoresis, about 1.1-kb DNA fragment was recovered.

Separately, 1 µg of pAMoA-FT3 obtained above was dissolved in 30 µl of Y-150 buffer, and 20 U each of Bam HI and Not I were added thereto, followed by digestion reaction at 37° C. for 2 hours.

After the reaction mixture was subjected to agarose gel electrophoresis, about 9.1-kb Bam HI-Not I-treated DNA fragment was recovered.

The resulting 0.1 µg of about 1.1-kb Bam HI-Not I-treated DNA fragment and 0.1 µg of about 9.1-kb Bam HI-Not I-treated DNA fragment were dissolved in 30 µl of T4 ligase buffer, and 175 U of T4 DNA ligase was added thereto, followed by ligation reaction at 12° C. for 16 hours.

The reaction mixture was used to transform *E. coli* MM294 by the method of Cohen et al. whereby ampicillin-resistant transformants were obtained.

A plasmid was isolated from the transformant in a known method, and its structure was confirmed by digestion with restriction enzymes. This plasmid was designated as pAMoA-i52S.

(2) Expression of Secretion-type iGnT in Namalwa KJM-1 Cells and Acquisition of Secretion-type iGnT Control plasmid pAMoA and plasmid pAMoA-i52S for secretory expression of iGnT constructed above were prepared using plasmid maxi kit (Product No. 41031) that is a plasmid preparation kit produced by Qiagen.

The plasmids thus prepared were precipitated with ethanol and were dissolved at a concentration of 1 µg/µl in TE buffer.

After dissolution, both the plasmids were introduced into Namalwa KJM-1 cells by the lipofection method described in Example 1 whereby transformants were obtained.

The transformants thus obtained were suspended at a density of $5 \times 10^4$ cells/ml in 30 ml of RPMI1640 ITPSGF medium containing 0.5 mg/ml G418 and then cultured at 37° C. for 9 days in a $CO_2$ incubator.

After culturing, the cells were removed by centrifugation at 160×g for 10 minutes and then at 1500×g for 10 minutes, and the supernatant was recovered.

The culture supernatant can be stored at −80° C. and thawed before use.

iGnT encoded by plasmid pAMoA-i52S is to be expressed through secretion as a fusion protein with the IgG-binding domain of protein A derived from *Staphylococcus aureus*, so it can be easily purified by IgG-Sepharose.

Sodium azide was added at a final concentration of 0.1% to the culture supernatant obtained above, and 30 µl of IgG-Sepharose (Pharmacia) pretreated according to manufacture's instructions was added thereto followed by overnight gentle stirring at 4° C.

After stirring, the IgG-Sepharose was recovered by centrifugation at 160×g for 10 minutes and then washed 3 times with 1 ml of buffer containing 50 mM Tris-HCl buffer (pH 7.6), 150 mM NaCl and 0.05% Tween 20.

After washing, the protein adsorbed on the IgG-Sepharose was eluted with 30 μl of 0.5 M acetate buffer (adjusted to pH 3.4 with ammonium acetate), and the IgG-Sepharose was removed by centrifugation at 160×g for 10 minutes.

To the eluate, 9 μl of 2 M Tris was added to adjust its pH to 7.0.

Figure 8:
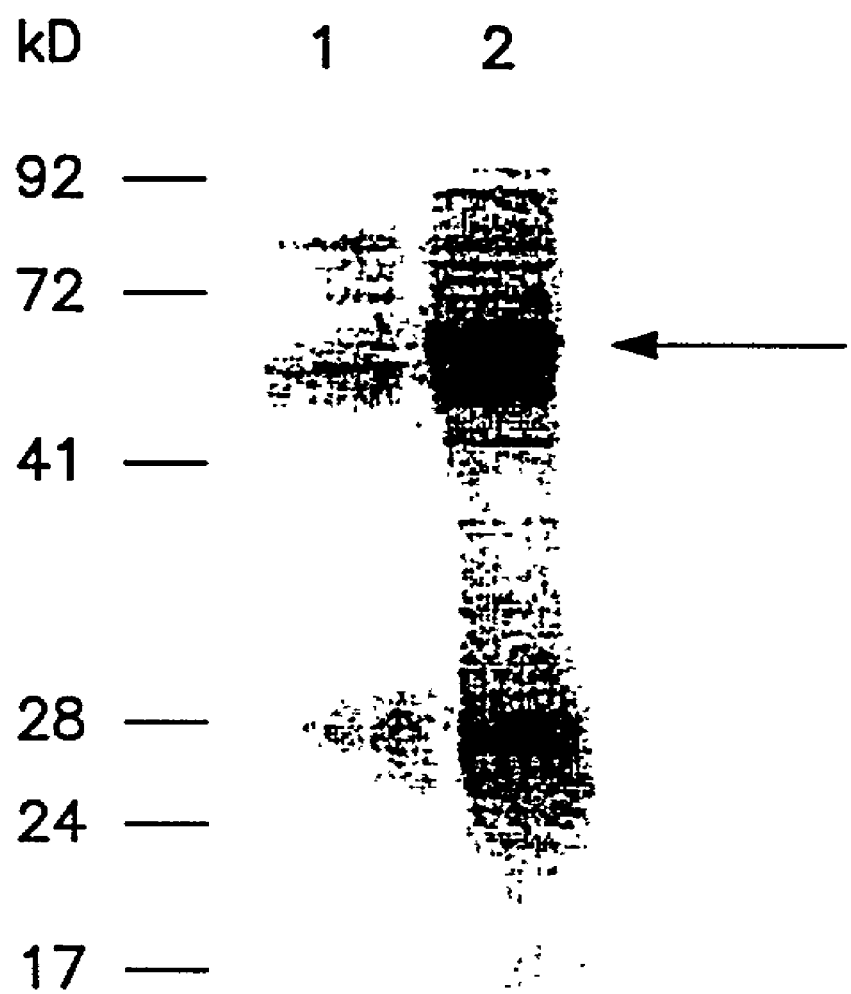
FIG. 8 shows the result of SDS-polyacrylamide gel electrophoresis (lane 2) of protein A-fused, secretion-type iGnT purified by IgG-Sepharose from a culture supernatant of Namalwa KJM-1 cells to which plasmid pAMoA-i52S had been introduced. As the control, a sample was prepared in the same manner from a culture supernatant of Namalwa KJM-1 cells into which pAMoA had been introduced, and it was subjected to SDS-polyacrylamide gel electrophoresis (lane 1).

SDS-PAGE was performed using 15 μl of the eluate thus prepared, followed by silver staining with a silver-staining kit Wako (Wako Pure Chemical Industries, Ltd.) (FIG. 8).

About 57-kD band was observed in the eluate derived from the culture supernatant of the Namalwa KJM-1 cells tranfected with pAMoA-i52S. On the other hand, about 57-kD band was not detected in the eluate derived from the culture supernatant of the Namalwa KJM-1 cells transformed with vector pAMoA.

This result indicated that the secretion-type iGnT can be produced through secretion as a fusion protein with the IgG-binding domain of protein A from *Staphylococcus aureus*, and said fusion protein can be easily purified with IgG-Sepharose.

Example 4

Figure 9:
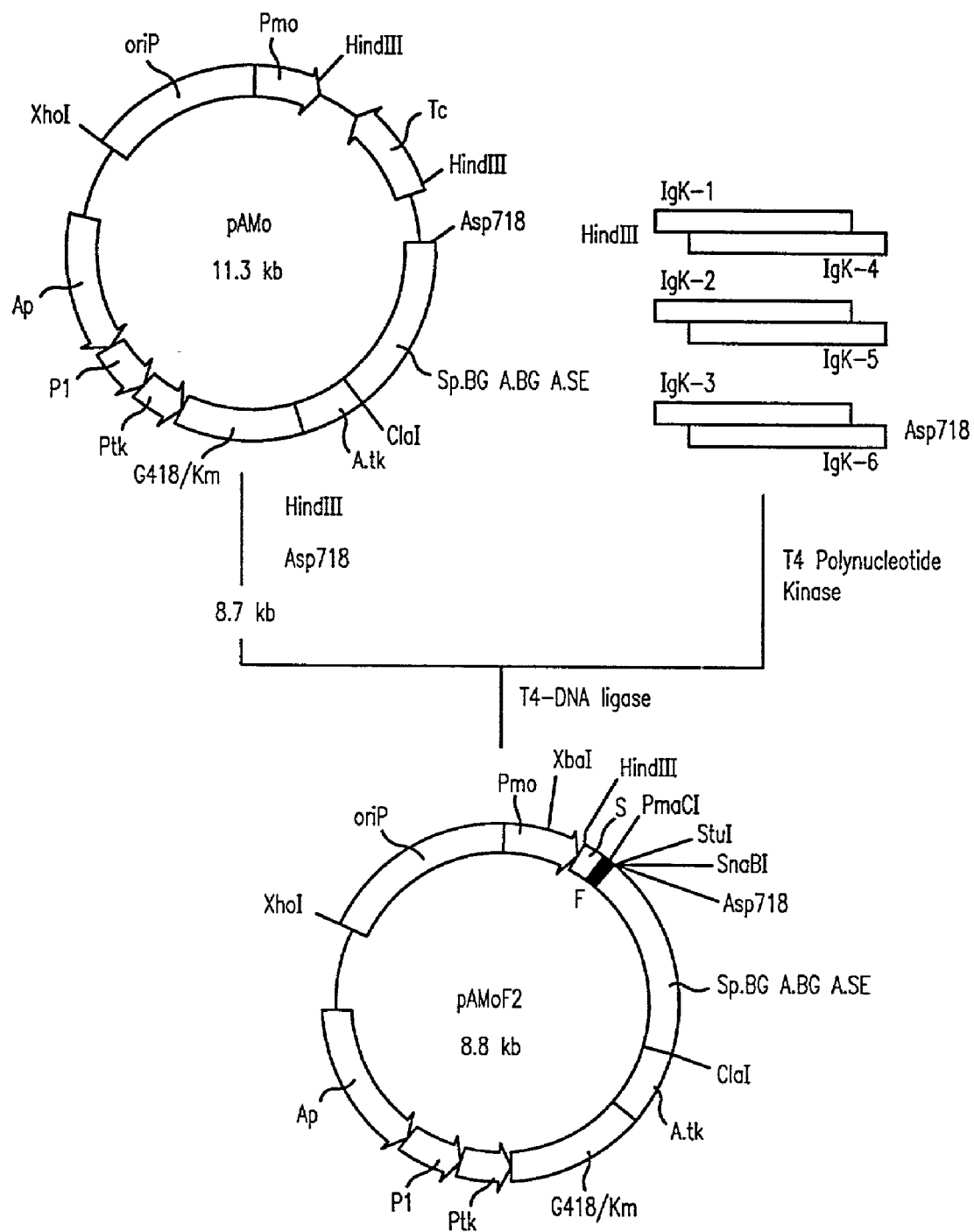
FIG. 9 shows the step of constructing plasmid pAMoF2.

Secretory Production of Flag-fused iGnT by Namalwa KJM-1 Cells as Host (1) Construction of Vector pAMoF2 for Secretory Expression of Flag-fused iGnT (FIG. 9)

Secretion vector pAMoF2, which allowed secretory expression of a protein of interest with a Flag peptide (SEQ ID NO:17) at N-termini, was constructed. DNA encoding a signal sequence of immunoglobulin κ and the Flag peptide was prepared using six kinds of synthetic DNAs.

One microgram of pAMo was dissolved in 20 μl of buffer containing 10 mM Tris-HCl buffer (pH 7.5), 6 mM MgCl$_2$, 80 mM NaCl and 6 mM 2-mercaptoethanol (this buffer is hereinafter referred to as Y-80 buffer), and 20 U each of Hind III and Asp 718 were added thereto, followed by digestion reaction at 37° C. for 2 hours.

After the reaction mixture was subjected to agarose gel electrophoresis, about 8.7-kb Hind III-Asp 718-treated DNA fragment was recovered.

Separately, 6 kinds of DNAs [IgK-1 (SEQ ID NO:7), IgK-2 (SEQ ID NO:8), IgK-3 (SEQ ID NO:9), IgK-4 (SEQ ID NO:10), IgK-5 (SEQ ID NO:11) and IgK-6 (SEQ ID NO:12)] were synthesized as linkers for linking the above Hind III and Asp 718 cleavage sites. The linker constructed by these DNAs has restriction enzyme cleave sites Pma CI, Stu I, and Sna BI. These 6 kinds of DNAs were synthesized in a 380A DNA synthesizer (Applied Biosystems). The synthesized DNAs (0.2 μg each) were dissolved in 20 μl of T4 kinase buffer and were phosphorylated at 37° C. for 2 hours in the presence of 30 U of T4 polynucleotide kinase (which is available from Takara Shuzo Co., Ltd.).

The resulting 6 kinds of phosphorylated synthetic DNAs (5 ng each) and 0.05 μg of about 8.7-kb Hind III-Asp 718-treated DNA fragment were dissolved in 20 μl of T4 ligase buffer and were ligated at 12° C. for 16 hours in the presence of 175 U of T4 DNA ligase.

The reaction mixture was used to transform *E. coli* MM294 by the method of Cohen et al. whereby ampicillin-resistant transformants were obtained.

From the transformants, a plasmid was isolated in a usual manner and its structure was confirmed by digestion with restriction enzymes and nucleotide sequencing. This plasmid is hereinafter referred to as pAMoF2 (FIG. 9).

Figure 10:
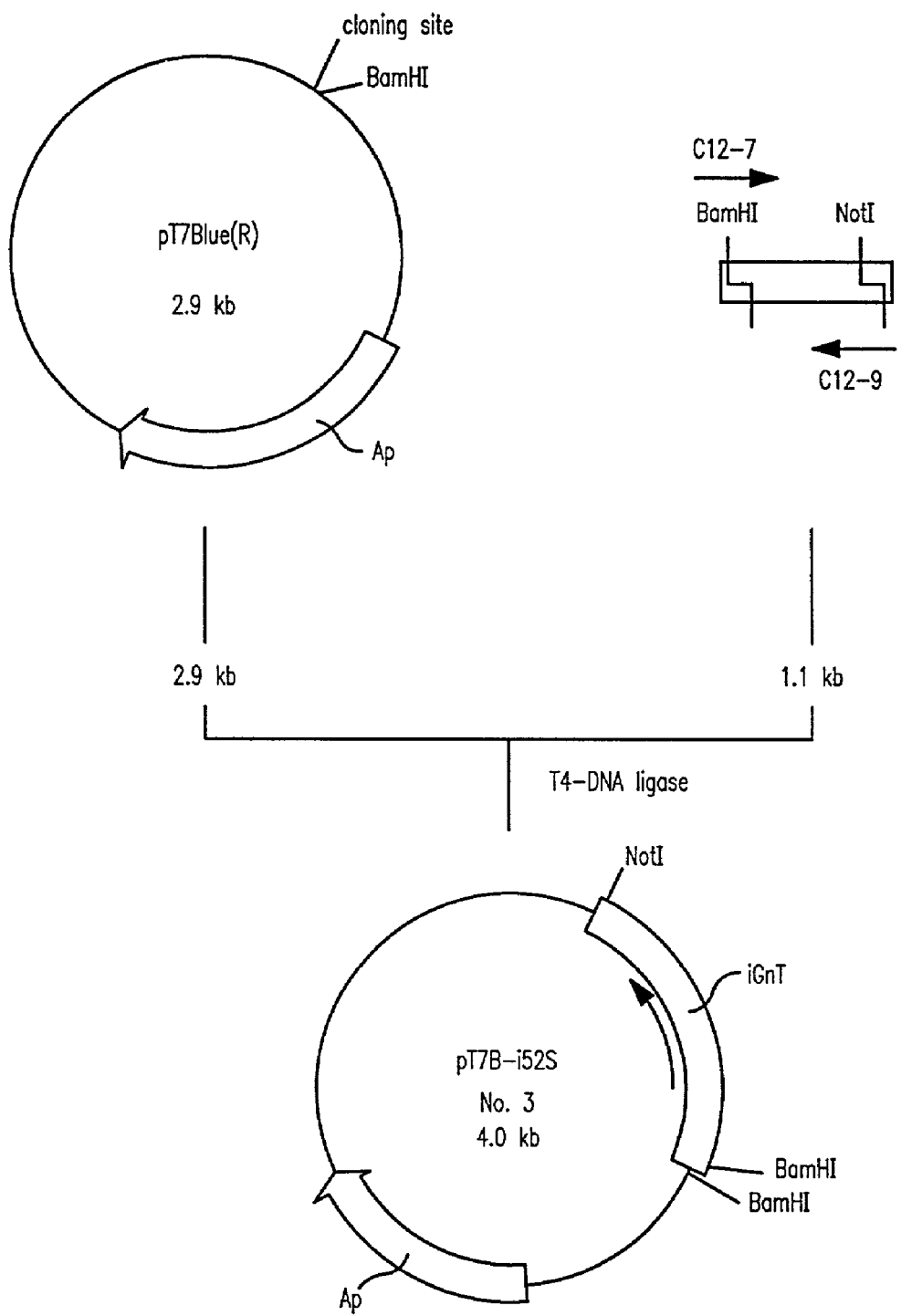
FIG. 10 shows the step of constructing plasmid pT7B-i52S No. 3.
Figure 11:
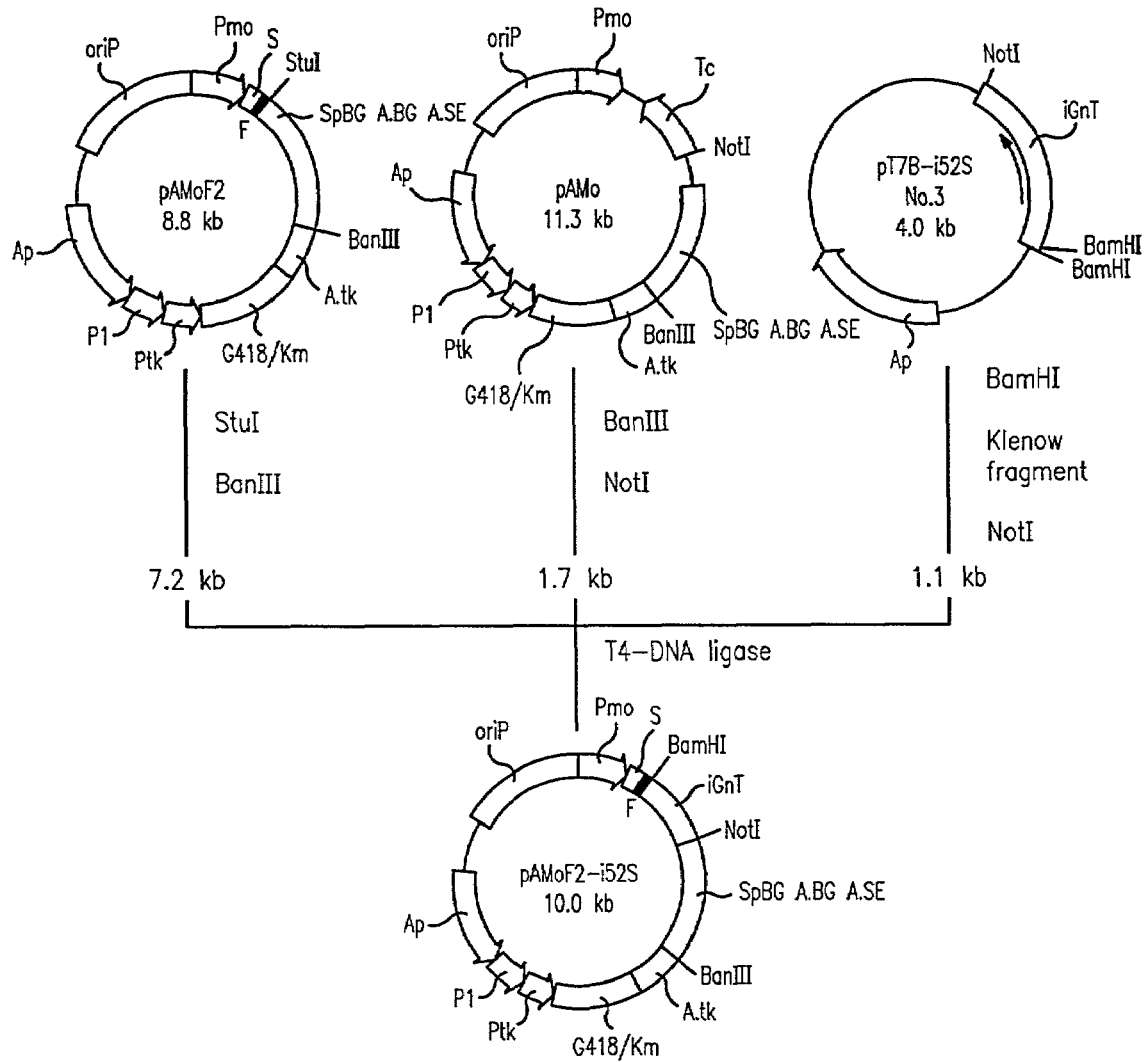
FIG. 11 shows the step of constructing plasmid pAMoF2-i52S.

(2) Construction of Plasmid pAMoF2-i52S for Secretory Expression of Flag-fused iGnT (FIGS. 10 and 11)

It was estimated from the primary sequence of cloned iGnT that iGnT consists of an N-terminal region (8 amino acids) located in cytoplasm, a subsequent membrane-binding region (28 amino acids) and a C-terminal region (379 amino acids) having catalytic activity. Hence, secretory expression of iGnT was attempted by replacing the N-terminal region located in cytoplasm and the membrane-binding region by a signal sequence of immunoglobulin and a Flag peptide.

The DNA fragment (prepared in Example 1) coding for a region [from Ser 52 to Cys 415 in SEQ ID NO:1] estimated to have catalytic activity for iGnT was integrated into T-vector pT7Blue (R) (Novagen) to construct plasmid pT7B-i52S No. 3.

pT7B-i52S No. 3 was constructed in the following manner (FIG. 10).

About 1.1-kb DNA fragment (0.1 μg) amplified by PCR, prepared in item (1) in Example 3, and 0.02 μg of T-vector pT7Blue (R) (Novagen) were dissolved in 30 μl of T4 ligase buffer and were ligated at 12° C. for 16 hours in the presence of 175 U of T4 DNA ligase.

The reaction mixture was used to transforme *E. coli* mM294 by the method of Cohen et al. whereby ampicillin-resistant transformants were obtained.

From the transformants, a plasmid was isolated in a usual manner and its structure was confirmed by digestion with restriction enzymes. This plasmid is hereinafter referred to as pT7B-i52S No. 3 (FIG. 10).

Then, plasmid pAMoF2-i52S for secretory expression of Flag-fused iGnT was constructed (FIG. 11).

One microgram of pAMoF2 was dissolved in 20 μl of Y-100 buffer, and 20 U each of Stu I and Ban III were added thereto, followed by digestion reaction at 37° C. for 2 hours.

After the reaction mixture was subjected to agarose gel electrophoresis, about 7.2-kb Stu I-Ban III-treated DNA fragment was recovered.

Separately, 1 μg of pAMo was dissolved in 20 μl of Y-100 buffer, and 20 U of Ban III was added thereto, followed by digestion reaction at 37° C. for 2 hours.

After reaction, 150 mM NaCl was added thereto, and 20 U of Not I was added thereto, followed by digestion reaction at 37° C. for 2 hours.

After the reaction mixture was subjected to agarose gel electrophoresis, about 1.7-kb Ban III-Not I-treated DNA fragment was recovered.

Separately, 1 μg of pT7B-i52S No. 3 was dissolved in 20 μl of Y-100 buffer, and 20 U of Bam III was added thereto, followed by digestion reaction at 37° C. for 2 hours.

After reaction, the fragment was precipitated with ethanol, and the resulting precipitate was dissolved in 30 μl of DNA polymerase I buffer, and 6 U of *E. coli* DNA polymerase I Klenow fragment was added thereto followed by reaction at 37° C. for 60 minutes whereby the 5'-protruding ends generated by Bam HI digestion were converted to blunt ends.

The reaction was terminated by phenol extraction, and after chloroform extraction and ethanol precipitation, the precipitate was dissolved in 30 μl of Y-150 buffer, and 20 U of Not I was added thereto, followed by digestion reaction at 37° C. for 2 hours.

After the reaction mixture was subjected to agarose gel electrophoresis, about 1.1-kb Bam HI (blunt-ended)-Not I-treated fragment was recovered.

The resulting 0.05 μg of about 7.2-kb Stu I-Ban III-treated fragment, 0.01 μg of about 1.7-kb Ban III-Not I-treated DNA fragment and 0.05 μg of about 1.1-kb Bam HI (blunt-ended)-Not I fragment were dissolved in 20 μl of T4 ligase buffer, and 175 U of T4 DNA ligase was added thereto, followed by ligation reaction at 12° C. for 16 hours.

The reaction mixture was used to transform *E. coli* MM294 by the method of Cohen et al. whereby ampicillin-resistant transformants were obtained.

From the transformants, a plasmid was isolated in a usual manner and its structure was confirmed by digestion with restriction enzymes. This plasmid was designated as pAMoF2-i52S (FIG. 11).

(2) Secretory Expression of Flag-fused iGnT in Namalwa KJM-1 Cells

Control plasmid pAMoF2 and plasmid pAMoF2-i52S constructed above for secretory expression of Flag-fused iGnT were prepared using a plasmid maxi kit (Product No. 41031) that is a plasmid preparation kit produced by Qiagen.

The plasmids thus prepared were precipitated with ethanol and were dissolved at a concentration of 1 μg/μl in TE buffer.

After dissolution, both the plasmids were introduced into Namalwa KJM-1 cells by the lipofection method described in Example 1 whereby transformants were obtained.

The transformant thus obtained was suspended at a density of $5 \times 10^4$ cells/ml in 30 ml of RPMI1640 medium containing 0.5 mg/ml G418 and 2% fetal bovine serum and then cultured at 37° C. for 9 days in a $CO_2$ incubator.

After culturing, the cells were removed by centrifugation at 160×g for 10 minutes and then at 1500×g for 10 minutes, and the supernatant was recovered.

The culture supernatant can be stored at −80° C. and thawed before use.

Because iGnT encoded by plasmid pAMoF2-i5254S is to be secreted and expressed as a fusion protein with the Flag peptide, it can be easily purified using anti-Flag M1 affinity gel (Cosmo Bio).

Sodium azide, sodium chloride and calcium chloride were added thereto at final concentrations of 0.1%, 150 mM and 2 mM, respectively, and 30 μl of anti-Flag M1 affinity gel (Cosmo Bio) was added thereto and slowly stirred at 4° C. overnight.

After stirring, the anti-Flag M1 affinity gel was recovered by centrifugation at 160×g for 10 minutes and then washed twice with 1 ml of buffer containing 50 mM Tris-HCl buffer (pH 7.4), 150 mM NaCl and 1 mM calcium chloride.

After washing, the protein adsorbed on the gel was eluted at 4° C. for 30 minutes with 30 μl of buffer containing 50 mM Tris-HCl (pH 7.4), 150 mM NaCl and 2 mM EDTA. Thereafter, the supernatant was recovered by centrifugation at 160×g for 10 minutes. The gel was treated again at 4° C. for 10 minutes with 30 μl of containing 50 mM Tris-HCl (pH 7.4), 150 mM NaCl and 2 mM EDTA, followed by centrifugation at 160×g for 10 minutes to give a supernatant. Thereafter, the same procedure as above was repeated, and in this way the elution procedure was repeated 3 times in total.

1 mM calcium chloride was added at a final concentration of 4 mM to the eluate.

Figure 12:
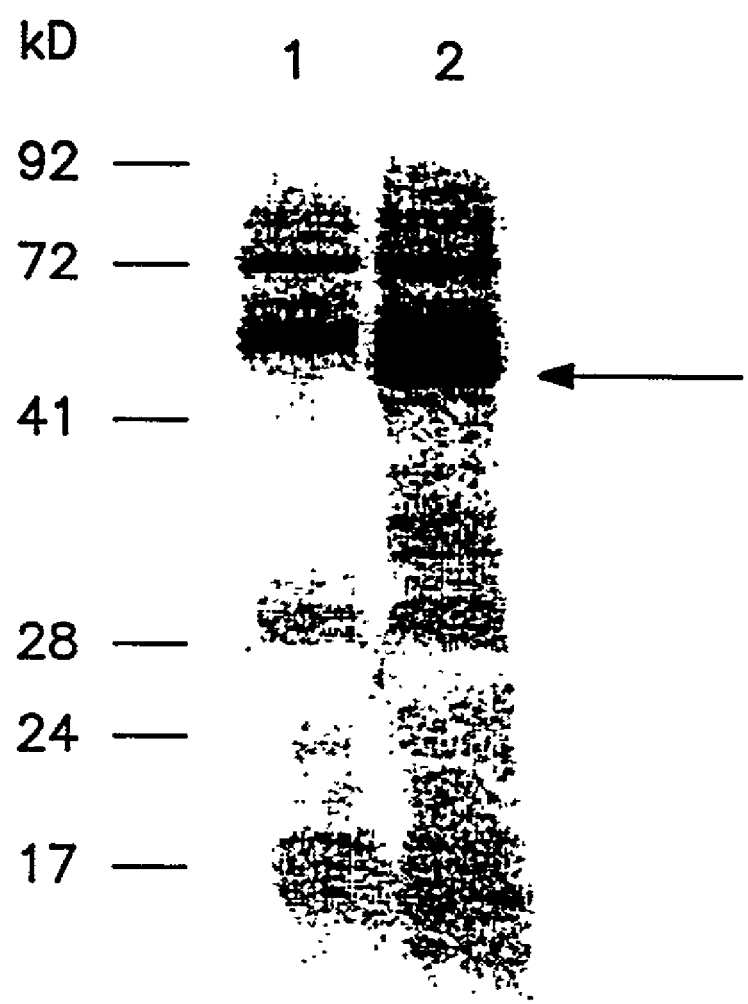
FIG. 12 shows the result of SDS-polyacrylamide gel electrophoresis (lane 2) of Flag peptide-fused, secretion-type iGnT purified by anti-Flag M1 affinity gel from a culture supernatant of Namalwa KJM-1 cells to which plasmid pAMoF2-i52S had been introduced. As the control, a sample was prepared in the same manner from a culture supernatant of Namalwa KJM-1 cells into which pAMoF2 had been introduced, and it was subjected to SDS-polyacrylamide gel electrophoresis (lane 1).

SDS-PAGE was performed using 15 μl of the first eluate prepared above, followed by silver staining with a silver-staining kit Wako (Wako Pure Chemical Industries, Ltd.) (FIG. 12).

About 49-kD band was observed in the eluate derived from the culture supernatant of the Namalwa KJM-1 cells transformed with pAMoA-i52S. On the other hand, about 49-kD band was not detected in the eluate derived from the culture supernatant of the Namalwa KJM-1 cells transformed with vector pAMoF2.

These results indicate that the Flag-fused iGnT can be secreted and produced and easily purified with the anti-Flag M1 affinity gel.

Example 5

Preparation of Recombinant Virus Solution for Production of iGnT in Insect Cells as Host (1) Preparation of a Recombinant Virus for Expression of iGnT in Insect Cells A recombinant virus was prepared by the following two steps: a step to integrate DNA encoing the objective protein into a special plasmid called transfer vector (step 1); and a step to prepare a recombinant virus by homologous recombination after co-transfection of insect cells with the transfer vector having the objective DNA integrated therein, as constructed in step 1, and a wild-type virus (step 2).

These steps were conducted using Baculo Gold Starter Kit (Product No. PM-21001K) (Pharmingen) according to instructions attached to the kit, as follows.

Figure 13:
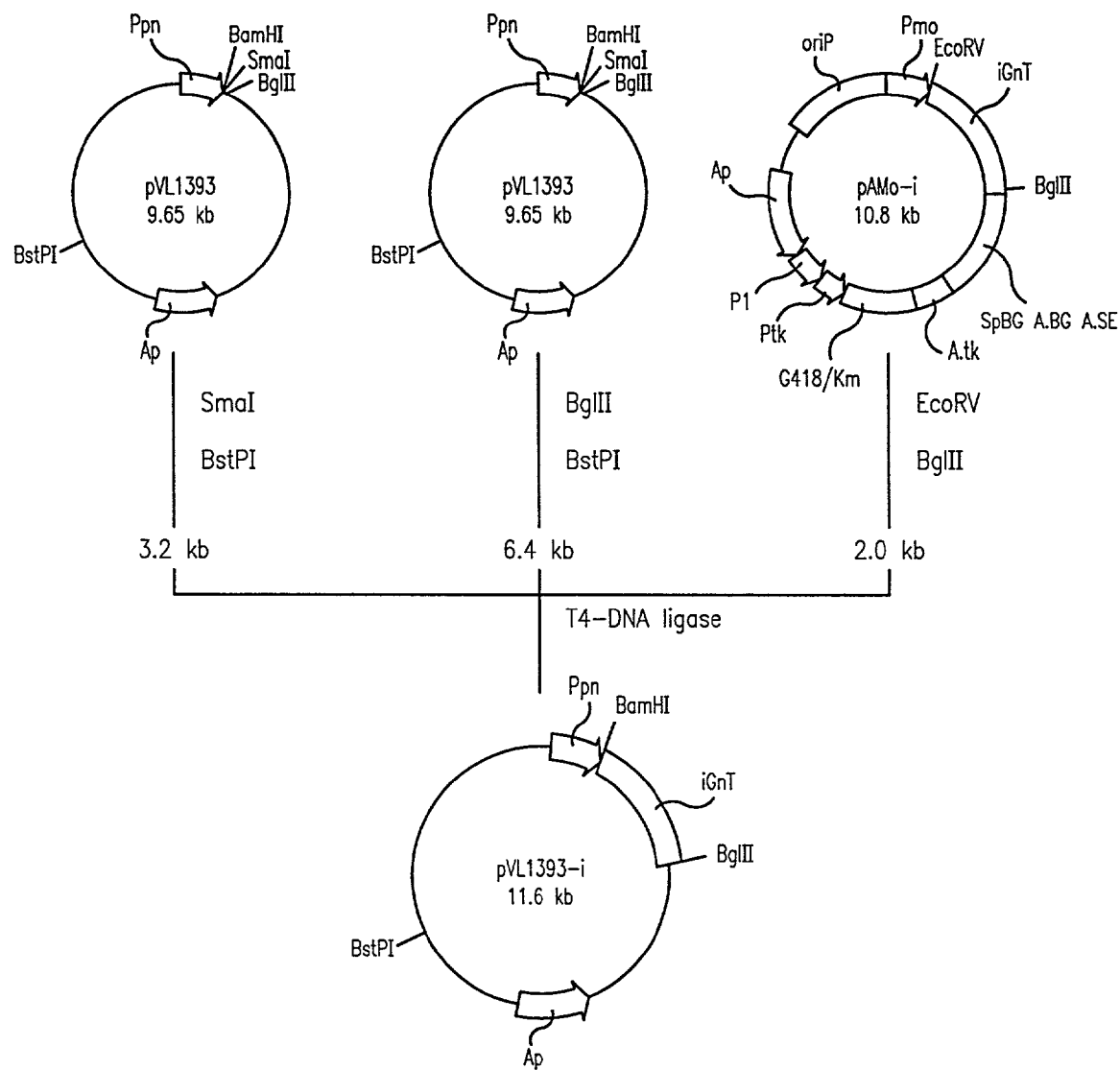
FIG. 13 shows the step of constructing plasmid pVL1393-i.

(Step 1) Integration of iGnT cDNA into the Transfer Vector (FIG. 13)

PlasmidpVL1393-i having iGnT cDNA integrated between Sma I and Bal II sites in transfer vector pVL1393 was constructed as follows.

One microgram of pVL1393 was dissolved in 25 μl of buffer containing 10 mM Tris-HCl (pH 7.5), 6 mM $MgCl_2$, 20 mM KCl and 6 mM 2-mercaptoethanol (this buffer is hereinafter to as K-20 buffer), and 20 U of Sma I was added thereto followed by digestion reaction at 37° C. for 2 hours.

After reaction, NaCl was added thereto at a concentration of 80 mM, and 20 U of Bst PI was added thereto followed by digestion reaction at 60° C. for 2 hours.

After the reaction mixture was subjected to agarose gel electrophoresis, about 3.2-kb Sma I-Bst PI-treated DNA fragment was recovered.

Separately, 1 μg of pVL1393 was dissolved in 25 μl of Y-80 buffer, 20 U of Bgl II was added thereto, followed by digestion reaction at 370° C. for 2 hours.

After reaction, 20 U of Bst PI was added thereto followed by further digestion reaction at 60° C. for 2 hours.

After the reaction mixture was subjected to agarose gel electrophoresis, about 6.4-kb Bal II-Bst PI-treated DNA fragment was recovered.

Separately, 1 μg of pAMo-i was dissolved in 25 μl of Y-150 buffer, 20 U each of Bal II and Eco RV were added thereto, followed by digestion reaction at 37° C. for 2 hours.

After the reaction mixture was subjected to agarose gel electrophoresis, about 2.0-kb Eco RV-Bgl II-treated DNA fragment was recovered.

The resulting 0.1 pg of about 3.2-kb Sma I-Bst PI-treated DNA fragment derived from pVL1393, 0.2 μg of about 6.4-kb Bgl II-Bst PI-treated DNA fragment derived from pVL1393, and 0.2 µg of about 2.0-kb Eco RV-Bgl II-treated DNA fragment derived from pAMo-i were dissolved in 30 µl of T4 ligase buffer and were ligated at 12° C. for 16 hours in the presence of 175 U of T4 DNA ligase.

The reaction mixture was used to transform *E. coli* MM294 by the method of Cohen et al. whereby ampicillin-resistant transformants were obtained. From the transformants, a plasmid was isolated in a usual manner. This plasmid was designated as pVL1393-i and its structure was confirmed by digestion with restriction enzymes (FIG. 13).

(Step 2) Preparation of a Recombinant Virus

Linear baculovirus DNA (BaculoGold baculovirus DNA available from Pharmingen) and the above plasmid pVL1393-i were introduced by the lipofectin method [Tanpakushitu Kakusan Koso (Enzyme, Nucleic Acid & Enzyme), 37, 2701 (1992)] into insect cell Sf9 (Pharmingen) cultured in TNF-FH insect medium (Pharmingen) to prepare a recombinant baculovirus, as follows:

After 1-5 µg of pVL1393-i and 15 ng of linear baculovirus DNA were dissolved in 12 µl of distilled water, a solution consisting of 6 µl (6 µg) of lipofection (Gibco BRL) and 6 µl of distilled water was added thereto and left at room temperature for 15 minute.

About $2 \times 10^6$ Sf9 cells were suspended in 2 ml of Sf900-II medium (Gibco BRL) and were placed in a cell-culture plastic plate of 35 mm in diameter and then the mixture of pVL1393-i, linear baculovirus DNA and lipofectin was added thereto followed by culturing at 27° C. for 3 days.

From the culture, 1 ml of supernatant containing the recombinant virus was collected.

One milliliter of TNM-FH insect medium was added to the plate from which the supernatant was collected, followed by further culturing at 27° C. for 4 days. After culturing, 1.5 ml of supernatant containing the recombinant virus was obtained in the same manner from the culture.

(2) Acquisition of a Recombinant Virus Solution

About $8 \times 10^6$ Sf9 cells were suspended in 5 ml of Sf900-II medium, then placed in a 75-cm² flask (Grainer), and left at room temperature for 30 minutes to allow the cells to adhere to the flask. Then, the supernatant was removed and 1 ml of Sf900-II medium and 1 ml of the supernatant obtained in item (1) above containing the recombinant virus were added to said flask.

After addition, the flask was gently shaken at room temperature for 1 hour so that the cells were adequately contacted with the virus, and 4 ml of TNM-FH insect medium was added thereto, followed by incubation at 27° C. for 4 days.

The culture was centrifuged at 1500×g for 10 minutes whereby 5.5 ml of solution containing the recombinant virus and age Sf9 cells infected with the recombinant virus were obtained.

About $2 \times 10^7$ Sf9 cells were suspended in 15 ml of Sf900-II medium, then placed in a 75-cm² flask (Grainer) and left at room temperature for 30 minutes to allow the cells to adhere to the flask. Then, the supernatant was removed and 5 ml of Sf900-II medium and 1 ml of the recombinant virus solution obtained above were added to the flask.

After addition, the flask was gently shaken at room temperature for 1 hour so that the cells were adequately contacted with the virus, and 10 ml of TNM-FH insect medium was added thereto, followed by incubation at 27° C. for 4 days.

The culture was centrifuged at 1500×g for 10 minutes whereby 15 ml of solution containing the recombinant virus and Sf9 cells infected with the recombinant virus were obtained.

The titer of this recombinant virus solution was calculated as follows [Baculo Gold Starter Kit Manual, Pharmingen].

About $6 \times 10^6$ Sf9 cells were suspended in 4 ml of Sf900-II medium, then placed in a cell-culture plastic plate of 60 mm in diameter, and left at room temperature for 30 minutes to allow the cells to adhere to the plate. Then, the supernatant was removed and 400 µl of Sf900-II medium and 100 µl of the above recombinant virus solution diluted at 10-4 or 10-5 with Sf900-II medium were added to the plate.

After addition, the plate was gently shaken at room temperature for 1 hour so that the cells were adequately contacted with the virus.

After they were contacted, the medium was removed from the plate, and a mixture of 2 ml of Sf900-II medium (maintained at 42° C.) containing 2% low-melting-point agarose (agarplaque agarose, Pharmingen) and 2 ml of TNM-FH insect medium (maintained at 42° C.) was poured into the plate, and the plate was left room temperature for 15 minutes.

Then, a vinyl tape was wound around the plate to prevent drying, then the plate was placed in a plastic container capable of being closed, and the cells were cultured therein at 27° C. for 5 days.

After culturing, 1 ml of PBS buffer containing 0.01% Neutral Red was added to the plate, and the cells were further cultured for 1 day, and the number of appeared plaques was counted.

By the above procedure, it was found that the recombinant virus solution contained the virus in an amount of about $1.2 \times 10^8$ plaque forming units (PFU)/ml.

Further, transfer vector pVL1393 was used to prepare a control recombinant virus and Sf9 cells infected with said virus. The control recombinant virus solution was found to contain the virus in an amount of about $1.4 \times 10^8$ plaque forming units (PFU)/ml.

Example 6

Secretory Production of Protein A-fused iGnT by Insect Cells as Host

The protein A-fused iGnT shown in Example 3 was expressed via secretion in insect cells.

Figure 14:
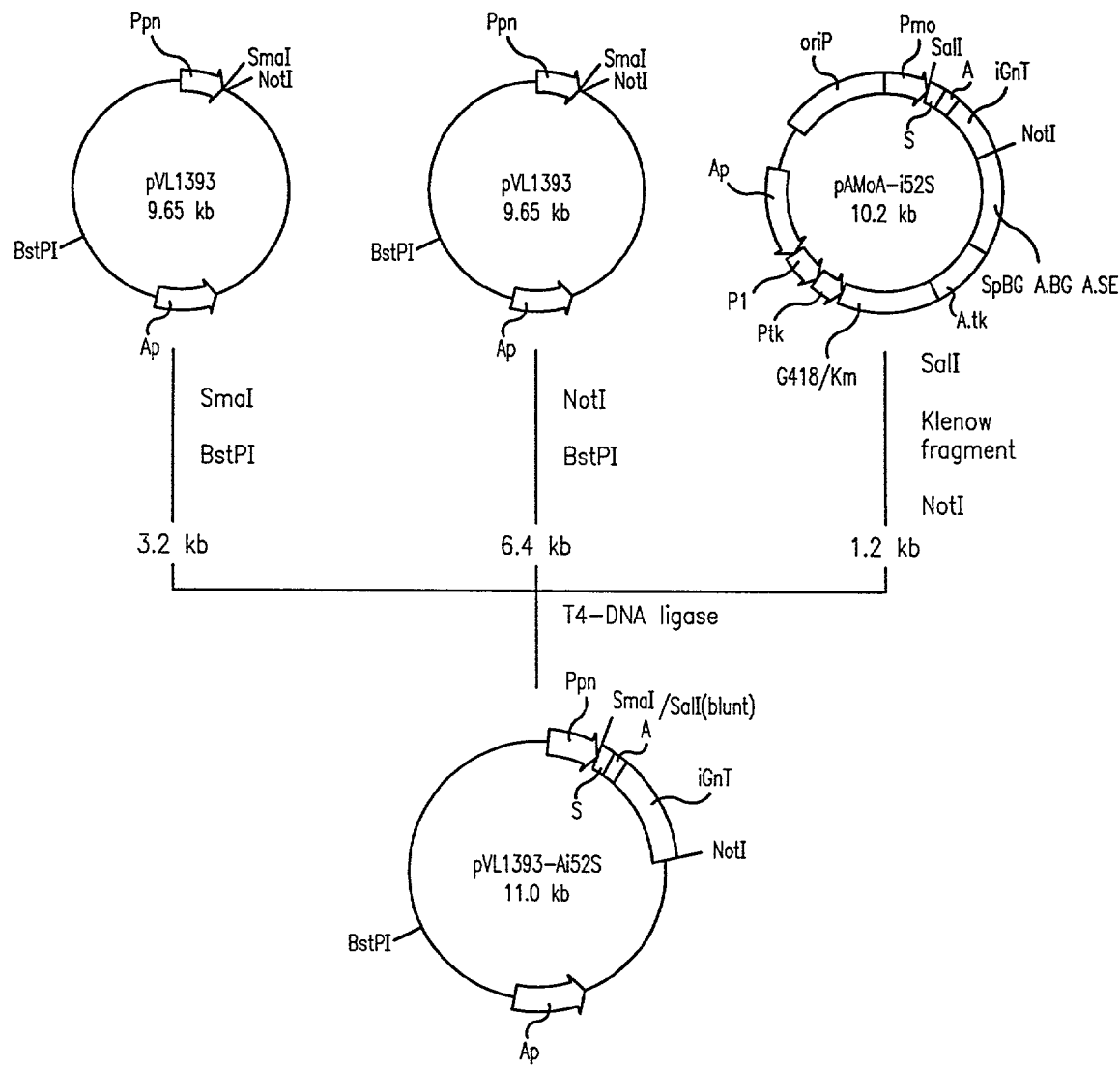
FIG. 14 shows the step of constructing plasmid pVL1393-Ai52S.

(1) Preparation of Recombinant Virus for Secretory Expression of Protein A-Fused iGnT in Insect Cells (Step 1) Integration of DNA Coding for Protein A-fused iGnT into a Transfer Vector (FIG. 14)

Plasmid pVL1393-Ai52S having DNA coding for secretion-type protein A-fused iGnT shown in Example 3 inserted between Sma I and Not I sites in multi-cloning sites in transfer vector pVL1393 was constructed as follows.

One microgram of pVL1393 was dissolved in K-20 buffer, and 20 U of Sma I was added thereto, followed by digestion reaction at 37° C. for 2 hours.

After reaction, NaCl was added thereto at a concentration of 80 mM, and 20 U of Bst PI was added thereto followed by digestion reaction at 60° C. for 2 hours.

After the reaction mixture was subjected to agarose gel electrophoresis, about 3.2-kb Sma I-Bst PI-treated DNA fragment was recovered.

Separately, 1 μg of pVL1393 was dissolved in 25 μl of Y-80 buffer, and 20 U of Bst PI was added thereto followed by digestion reaction at 60° C. for 2 hours.

After reaction, NaCl was added thereto at a concentration of 150 mM, and 20 U of Not I was added thereto followed by digestion reaction at 37° C. for 2 hours.

After the reaction was subjected to agarose gel electrophoresis, about 6.4-kb Not I-Bst PI-treated DNA fragment was recovered.

One microgram of pAMoA-i52S (prepared in Example 3) was dissolved in 25 μl of Y-100 buffer, and 20 U of SalI was added thereto, followed by digestion reaction at 37° C. for 2 hours.

After reaction, the fragment was precipitated with ethanol, and the resulting precipitate was dissolved in 30 μl of DNA polymerase I buffer, and 6 U of *E. coli* DNA polymerase Klenow fragment was added thereto followed by reaction at 37° C. for 60 minutes whereby the 5'-protruding ends generated by Sal I digestion was converted to blunt ends.

The reaction was terminated by phenol extraction, and after chloroform extraction and ethanol precipitation, the precipitate was dissolved in 30 μl of Y-150 buffer, and 20 U of Not I was added thereto, followed by digestion reaction at 37° C. for 2 hours.

After the reaction mixture was subjected to agarose gel electrophoresis, about 1.4-kb Sal I (blunt-ended)-Not I-treated DNA fragment was recovered.

The resulting 0.1 μg of about 3.2-kb Sma I-Bst PI-treated DNA fragment derived from pVL1393, 0.2 μg of about 6.4-kb Not I-Bst PI-treated DNA fragment derived from pVL1393, and 0.2 μg of about 1.4-kb Sal I (blunt-ended)-Not I-treated DNA fragment derived from pAMoA-i52S were dissolved in 30 μl of T4 ligase buffer, and 175 U of T4 DNA ligase was added thereto, followed by ligation reaction at 12° C. for 16 hours.

The reaction mixture was used to transform *E. coli* MM294 by the method of Cohen et al. whereby ampicillin-resistant transformants were obtained. From the transformants, a plasmid was isolated in a usual manner. This plasmid was designated as pVL1393-Ai52S and its structure was confirmed by digestion with restriction enzymes (FIG. 14).

(Step 2) Preparation of a Recombinant Virus

A recombinant baculovirus solution (1.5 ml) derived from pVL1393-Ai52S was obtained in the same manner as in (Step 2) in Example 5.

(2) Acquisition of Sf9 Cells Infected with the Recombinant Virus and the Recombinant Virus Solution About 8×10⁶ Sf9 cells were infected in the same manner as in item (2) in Example 5 with the recombinant virus obtained in item (1) above, whereby 5.5 ml of the recombinant virus solution and Sf9 cells infected with the recombinant virus were obtained.

About 2×10⁷ Sf9 cells were infected in the same manner as in item (2) in Example 5 with the recombinant virus obtained above, whereby 15 ml of the recombinant virus solution and Sf9 cells infected with the recombinant virus were obtained.

Separately, transfer vector pVL1393 was used to prepare a control recombinant virus and Sf9 cells infected with the control recombinant virus.

(3) Secretory Production and Purification of Protein A-fused iGnT Polypeptide

Because iGnT encoded by the recombinant virus derived from plasmid pVL1393-Ai52S is to be secreted and expressed as a fusion protein with the IgG-binding domain of protein A from *Staphylococcus aureus*, it can be easily purified using IgG-Sepharose.

About 2×10⁷ Sf21 cells were suspended in 15 ml of Sf900-II medium, then placed in a 75-cm² flask (Grainer) and left at room temperature for 30 minutes whereby the cells adhered to the flask. Then, the supernatant was removed and 5 ml of Sf900-II medium and 1 ml of the recombinant virus solution obtained in item (2) above were added to the flask.

After addition, the flask was gently shaken at room temperature for 1 hour so that the cells were adequately contacted with the virus, and 10 ml of TNM-FH insect medium was added thereto, followed by incubation at 27° C. for 4 days.

The culture was centrifuged at 1500×g for 10 minutes whereby 15 ml of culture supernatant estimated to contain secretion-type iGnT was obtained.

Sodium azide was added at a concentration of 0.1% to the 10 ml of the culture supernatant obtained above, and 100 μl of IgG-Sepharose (Pharmacia) pretreated according to manufacturer's instructions was added thereto and slowly stirred at 4° C. overnight.

After stirring, the IgG-Sepharose was recovered by centrifugation at 160×g for 10 minutes and then washed 3 times with 1 ml of buffer containing 50 mM Tris-HClb(pH 7.6), 150 mM NaCl and 0.05% Tween 20.

After washing, the protein adsorbed on the IgG-Sepharose was eluted with 100 μl of 0.5 M acetate buffer (adjusted to pH 3.4 with ammonium acetate), and the IgG-Sepharose was removed by centrifugation at 160×g for 10 minutes.

To the eluate, 30 μl of 2 M Tris was added to adjust its pH to 7.0.

Figure 15:
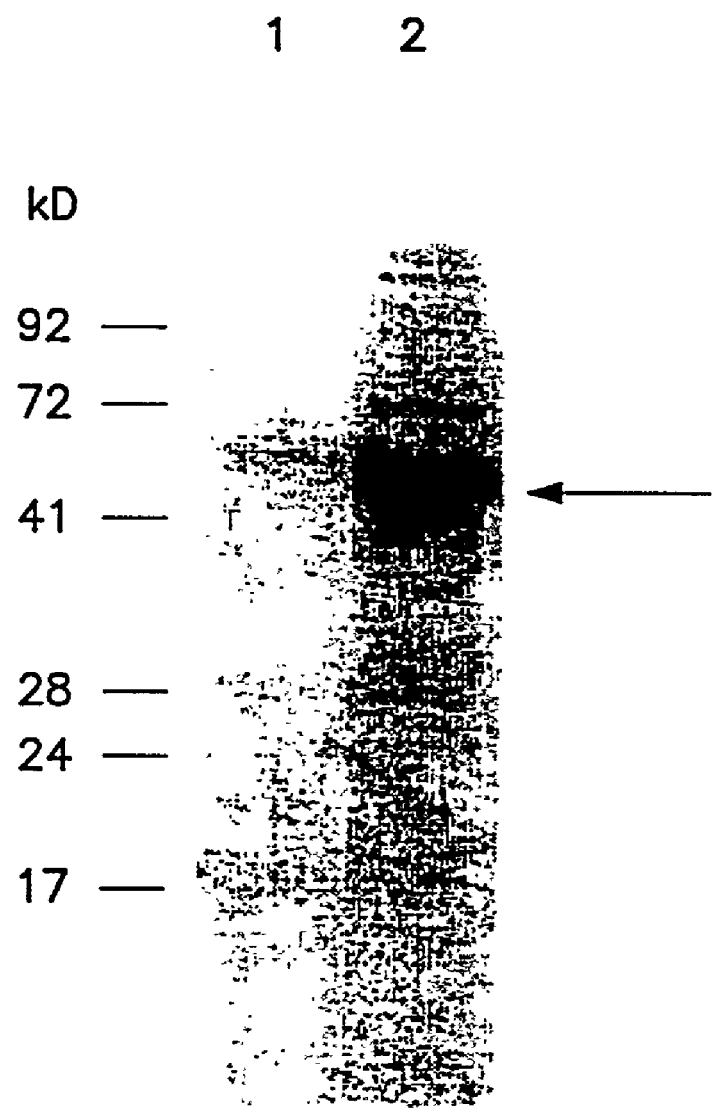
FIG. 15 shows the result of SDS-polyacrylamide gel electrophoresis (lane 2) of protein A-fused, secretion-type iGnT purified by IgG-Sepharose from a culture supernatant of Sf21 cells infected with a recombinant virus derived from plasmid pVL1393-Ai52S. As the control, a sample was prepared in the same manner from a culture supernatant of Sf21 cells infected with a recombinant virus derived from plasmid pVL1393, and it was subjected to SDS-polyacrylamide gel electrophoresis (lane 1).

SDS-PAGE was performed using 15 μl of the eluate thus adjusted, followed by staining with Coomassie Brilliant Blue (FIG. 15).

About 50-kD band was observed in the eluate derived from the culture supernatant of Sf21 infected with the recombinant virus derived from pVL1393-Ai52S. On the other hand, about 50-kD band was not detected in the eluate derived from the culture supernatant of Sf21 infected with the recombinant virus derived from vector pVL1393.

These results indicate that the secretion-type iGnT can be produced through secretion as a fusion protein with the IgG-binding domain of protein A from *Staphylococcus aureus* and can be easily purified by use of IgG-Sepharose.

Example 7

Secretory Production of Flag Peptide-fused iGnT by Insect Cells as Host

The Flag peptide-fused iGnT shown in Example 4 was expressed via secretion in insect cells.

Figure 16:
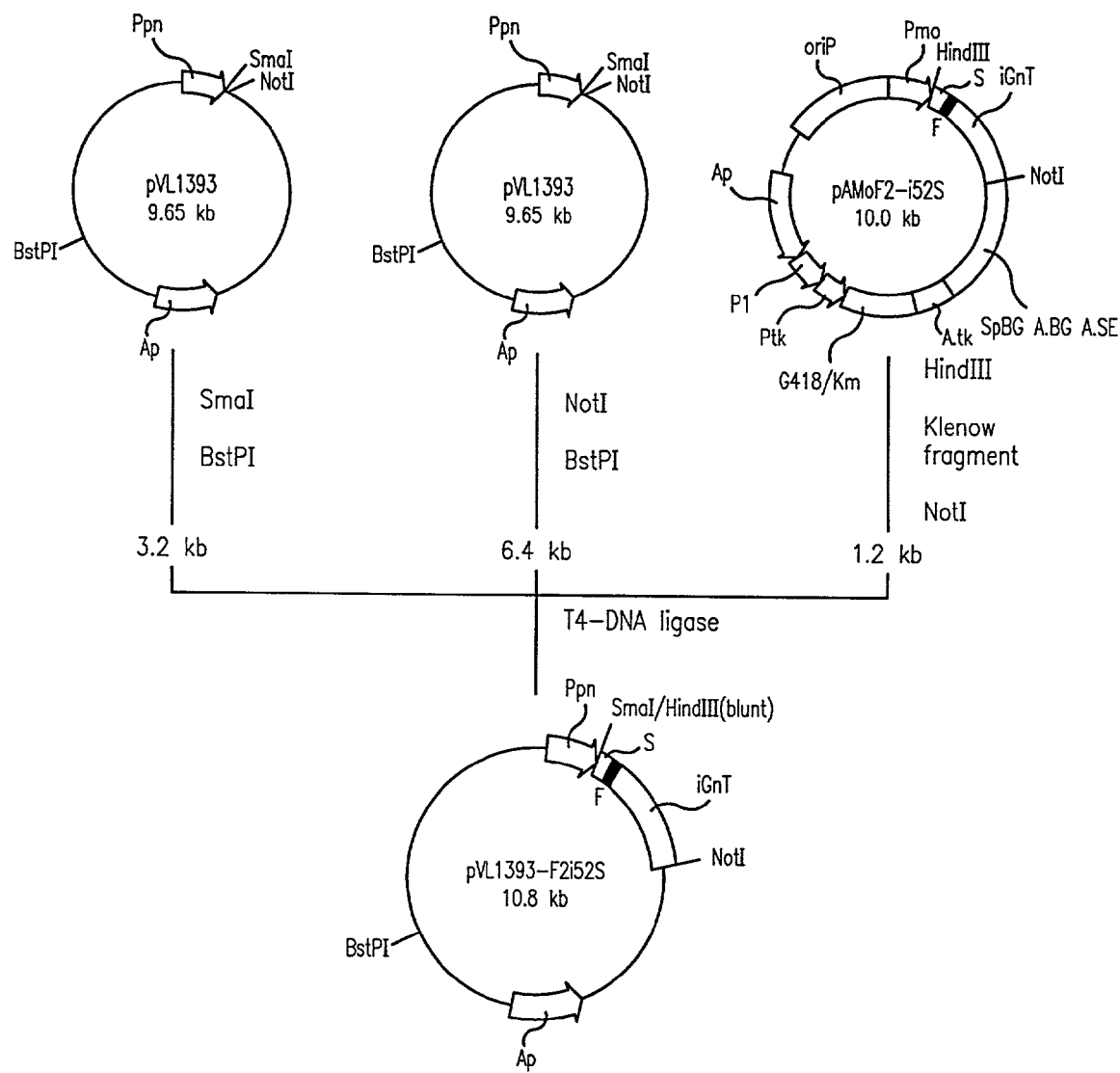
FIG. 16 shows the step of constructing plasmid pVL1393-F2i52S.

(1) Preparation of a Recombinant Virus for Secretory Expression of Flag Peptide-fused iGnT in Insect Cells (Step 1) Integration of DNA Coding for Flag Peptide-fused iGnT into a Transfer Vector (FIG. 16)

Plasmid pVL1393-F2i52S having the DNA coding for Flag peptide-fused iGnT shown in Example 4 inserted between Sma I and Not I sites in multi-cloning sites in transfer vector pVL1393 was constructed.

One microgram of pAMoF2-i52S prepared in Example 4 was dissolved in 25 μl of Y-80 buffer, and 20 U of Hind III was added thereto, followed by digestion reaction at 37° C. for 2 hours.

After reaction, the fragment was precipitated with ethanol, and the resulting precipitate was dissolved in 30 μl of DNA polymerase I buffer, and 6 U of *E. coli* DNA polymerase Klenow fragment was added thereto followed by reaction at 37° C. for 60 minutes whereby the 5'-protruding ends generated by Hind III digestion was converted to blunt ends.

The reaction was terminated by phenol extraction, and after chloroform extraction and ethanol precipitation, the precipitate was dissolved in 30 μl of Y-150 buffer, and 20 U of Not I was added thereto, followed by digestion reaction at 37° C. for 2 hours.

After the reaction mixture was subjected to agarose gel electrophoresis, about 1.2-kb Hind III (blunt-ended)-Not I-treated DNA fragment was recovered.

The resulting 0.2 μg of about 1.2-kb Hind III (blunt-ended)-Not I-treated DNA fragment, 0.1 μg of about 3.2-kb Sma I-Bst PI-treated DNA fragment derived from pVL1393 obtained in item (1) in Example 5, and 0.2 μg of about 6.4-kb Not I-Bst PI-treated DNA fragment derived from pVL1393 obtained in item (1) in Example 5 were dissolved in 30 μl of T4 ligase buffer, and 175 U of T4 DNA ligase was added thereto, followed by ligation reaction at 12° C. for 16 hours.

The reaction mixture was used to transform *E. coli* MM294 by the method of Cohen et al. whereby ampicillin-resistant transformants were obtained. From the transformants, a plasmid was isolated in a usual manner. This plasmid was designated as pVL1393-F2i52S (FIG. 16) and its structure was confirmed by digestion with restriction enzymes.

(Step 2) Preparation of a Recombinant Virus

A recombinant baculovirus solution (1.5 ml) derived from pVL1393-F2i52S was obtained in the same manner as in (Step 2) of Example 5.

(2) Acquisition of Sf9 Cells Infected with the Recombinant Virus and the Recombinant Virus Solution About 8×10⁶ Sf9 cells were infected in the same manner as in item (2) in Example 5 with the recombinant virus obtained in item (1) above, whereby 5.5 ml of the recombinant virus solution and Sf9 cells infected with the recombinant virus were obtained.

About 2×10⁷ Sf9 cells were infected in the same manner as in item (2) in Example 5 with the recombinant virus obtained above, whereby 15 ml of the recombinant virus solution and Sf9 cells infected with the recombinant virus were obtained.

Separately, transfer vector pVL1393 was used to prepare a control recombinant virus and Sf9 cells infected with the control recombinant virus.

(3) Secretory Production and Purification of the Flag Peptide-fused iGnT Polypeptide Because iGnT encoded by the recombinant virus derived from plasmid pVL1393-F2i52S is to be secreted and expressed as a fusion protein with the Flag peptide, it can be easily purified using anti-Flag M1 affinity gel (Cosmo Bio).

About 2×10⁷ Sf21 cells were suspended in 15 ml of Sf900-II medium in a 75-cm² flask (Grainer) and left at room temperature for 30 minutes whereby the cells adhered to the flask. Then, the supernatant was removed and 5 ml of Sf900-II medium and 1 ml of the recombinant virus solution obtained in item (2) above were added to the flask.

After addition, the flask was gently shaken at room temperature for 1 hour so that the cells were adequately contacted with the virus, and 10 ml of TNM-FH insect medium was added thereto, followed by incubation at 27° C. for 4 days. The culture was centrifuged at 1500×g for 10 minutes whereby 15 ml of culture supernatant estimated to contain secretion-type iGnT was obtained.

Sodium azide, sodium chloride and calcium chloride were added to the culture supernatant at final concentrations of 0.1%, 150 mM and 2 mM, respectively, and 80 μl of anti-Flag M1 affinity gel (Cosmo Bio) was added thereto and slowly stirred at 4° C. overnight.

After stirring, the anti-Flag M1 affinity gel was recovered by centrifugation at 160×g for 10 minutes and then washed twice with 1 ml of buffer containing 50 mM Tris-HCl (pH 7.4), 150 mM NaCl and 1 mM calcium chloride.

After washing, the protein adsorbed on the gel was eluted at 4° C. for 30 minutes with 80 μl of buffer containing 50 mM Tris-HCl (pH 7.4), 150 mM NaCl and 2 mM EDTA. Thereafter, the supernatant was recovered by centrifugation at 160×g for 10 minutes. The gel was treated again at 4° C. for 10 minutes with 80 μl of buffer containing 50 mM Tris-HCl (pH 7.4), 150 mM NaCl and 2 mM EDTA, followed by centrifugation at 160×g for 10 minutes to give a supernatant. Thereafter, the same procedure as above was repeated, and the elution procedure was repeated 3 times in total.

To the eluate, 1 M calcium chloride was added at a final concentration of 4 mM.

Figure 17:
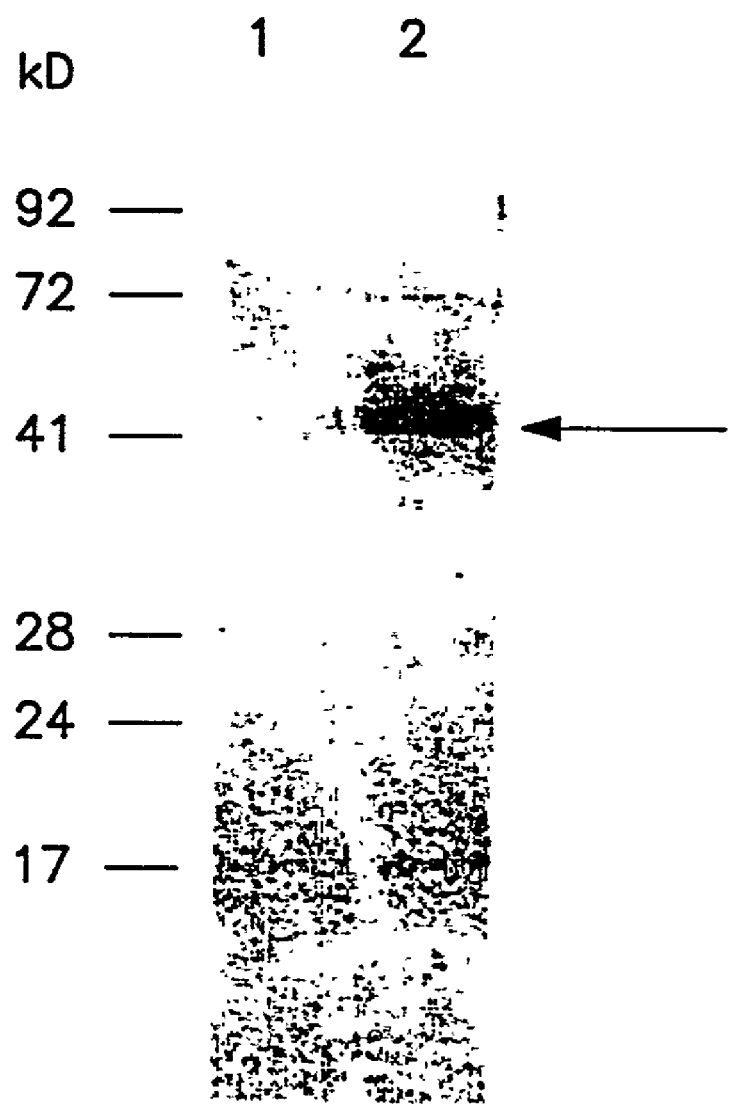
FIG. 17 shows the result of SDS-polyacrylamide gel electrophoresis (lane 2) of Flag peptide-fused, secretion-type iGnT purified by anti-Flag M1 affinity gel from a culture supernatant of Sf21 cells infected with a recombinant virus derived from plasmid pVL1393-F2i52S. As the control, a sample was prepared in the same manner from a culture supernatant of Sf21 cells infected with a recombinant virus derived from plasmid pVL1393 and it was subjected to SDS-polyacrylamide gel electrophoresis (lane 1).

SDS-PAGE was performed using 15 μl of the first eluate thus prepared, followed by staining with Coomassie Brilliant Blue (FIG. 17).

About 43-kD band was observed in the eluate derived from the culture supernatant of Sf21 transformed with the recombinant virus derived from pVL1393-F2i52S. On the other hand, about 43-kD band was not detected in the eluate derived from the culture supernatant of Sf21 infected with the recombinant virus derived from vector pVL1393.

These results indicate that the Flag-fused iGnT can be produced through secretion and can be easily purified by use of anti-Flag M1 affinity gel.

Example 8

Establishment of a Method for Determination of iGnT Transcripts Using PCR and Examination of the Expression Level in Various Cells Determination of the iGnT transcripts was conducted according to quantitative PCR [Proc. Natl. Acad. Sci. USA, 87, 2725 (1990)]. The amount of the iGnT transcripts in various cells and cell lines was expressed as a relative value with the amount of β-actin transcripts, which is considered to be expressed in similar degrees in any cells, being taken as 100%.

Figure 18:
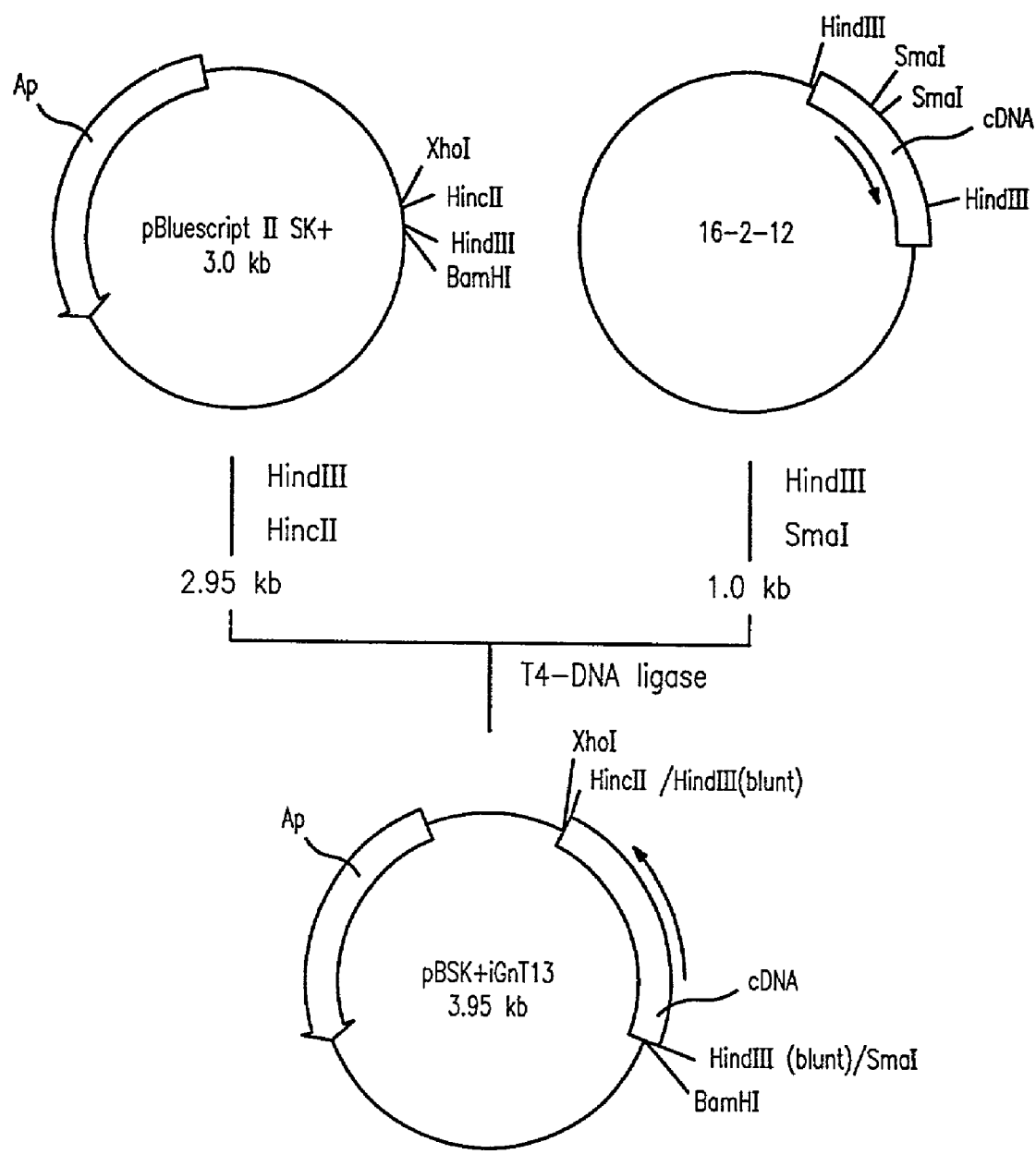
FIG. 18 shows the step of constructing plasmid pBSK+ iGnT13.

(1) Construction of Standard Plasmid pBSK+iGnT13 (FIG. 18)

A plasmid (designated as pBSK+iGnT13), which was constructed for sequencing of iGnT cDNA in item (4) in Example 1, was used as a standard plasmid. This plasmid was constructed by subcloning a Hind III-Sma I fragment (about 1.0 kb, fragment No. 13 in FIG. 3) derived from plasmid 16-2-12 between Hind III-Hinc II sites in pBluescript II SK(+). A method of constructing this plasmid is as follows:

One microgram of plasmid 16-2-12 was dissolved in 25 μl of buffer containing 10 mM Tris-HCl (pH 7.5), 6 mM MgCl$_2$, 60 mM KCl, and 6 mM 2-mercaptoethanol, and 20 U each of Hind III and Sma I were added thereto, followed by digestion reaction at 37° C. for 2 hours.

After the reaction mixture was subjected to agarose gel electrophoresis, about 1.0-kb Hind III-Sma I-treated DNA fragment was recovered.

One microgram of pBluescript II SK(+) was dissolved in 25 μl of Y-50 buffer, and 20 U each of Hind III and Hinc II were added thereto, followed by digestion reaction at 37° C. for 2 hours.

After the reaction mixture was subjected to agarose gel electrophoresis, about 2.95-kb Hind III-Hinc II-treated DNA fragment was recovered.

The resulting 0.1 μg of about 1.0-kb Hind III-Sma I-treated DNA fragment and 0.05 μg of about 2.95-kb Hind III-Hinc III-treated DNA fragment were dissolved in 20 μl of T4 ligase buffer, and 175 U of T4 DNA ligase was added thereto, followed by ligation reaction at 12° C. for 16 hours.

The reaction mixture was used to transform *E. coli* JM105 by the method of Cohen et al. whereby ampicillin-resistant transformants were obtained.

From the transformants, a plasmid was isolated in a usual manner.

This plasmid was designated as pBSK+iGnT13, and its structure was confirmed by restriction enzyme digestion and nucleotide sequencing. The structure of this plasmid is shown in FIG. 18.

Figure 19:
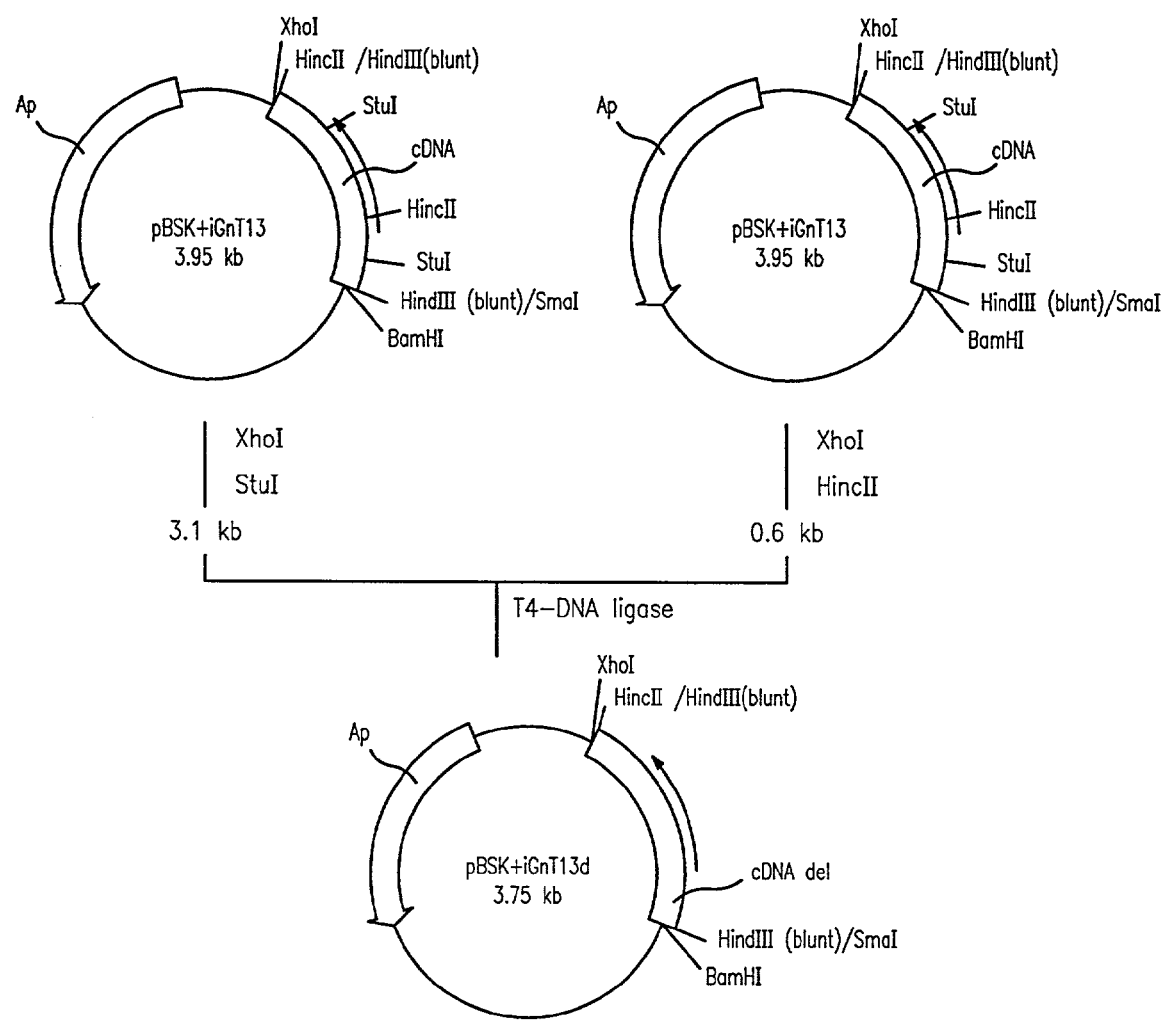
FIG. 19 shows the step of constructing plasmid pBSK+ iGnT13d.

(2) Construction of Internal Control Plasmid pBSK+iGnT13d (FIG. 19)

Plasmid pBSK+iGnT13d having a deletion mutation within the iGnT cDNA in pBSK+iGnT13 constructed in item (1) above was constructed.

One microgram of pBSK+iGnT13 was dissolved in 25 μl of Y-100 buffer, and 20 U each of Xho I and Stu I were added thereto, followed by digestion reaction at 37° C. for 2 hours.

After the reaction mixture was subjected to agarose gel electrophoresis, about 3.1-kb Xho I-Stu I-treated DNA fragment was recovered.

One microgram of pBSK+iGnT13 was dissolved in 25 μl of Y-100 buffer, and 20 U each of Xho I and Hinc II were added thereto, followed by digestion reaction at 37° C. for 2 hours.

After the reaction mixture was subjected to agarose gel electrophoresis, about 0.6-kb Xho I-Hinc II-treated DNA fragment was recovered.

The resulting 0.05 μg of about 3.1-kb Xho I-Stu I-treated DNA fragment and 0.1 μg of about 0.6-kb Xho I-Hinc II-treated DNA fragment were dissolved in 20 μl of T4 ligase buffer, and 175 U of T4 DNA ligase was added thereto, followed by ligation reaction at 12° C. for 16 hours.

The reaction mixture was used to transform *E. coli* MM294 by the method of Cohen et al. whereby ampicillin-resistant transformants were obtained.

From the transformants, a plasmid was isolated in a usual manner.

This plasmid was designated as pBSK+iGnT13d, and its structure was confirmed by digestion with restriction enzymes. The structure of this plasmid is shown in FIG. 19.

(3) Determination of the iGnT Transcripts in Various Cells and Cell Lines by Quantitative PCR Techniques (a) Synthesis of Single-Stranded cDNAs Derived from Various Cells and Cell Lines (Used as Templates for Quantitative PCR)

The cell lines used were Namalwa KJM-1 cells, WM266-4 cells, THP-1 cells, HL-60 cells, U-937 cells, Colo205 cells, LS180 cells, SW1116 cells and Jurkat cells. WM266-4 cells, THP-1 cell, HL-60 cells, U-937 cells, Colo205 cells and LS180 cells were obtained from American Type Culture Collection (ATCC). SW1116 cells (available from ATCC) and Jurkat cells (available from Riken Gene Bank) were obtained from Dr. Takahashi, Aichi Pref. Cancer Center.

Polymorphonuclear leukocytes and mononuclear cells were separated and obtained from peripheral blood from the healthy adult donors by use of a Polymorphprep™ kit (Nycomed Pharma).

According to aconventional method [J. Immunol., 130, 706 (1983)], the mononuclear cells were further separated into monocytes and lymphocytes.

Total RNAs from the respective cells were prepared according to a conventional method [Biochemistry, 18, 5294 (1977)].

From the total RNA, single-stranded cDNA was synthesized using a kit Superscript™ Preamplification System (BRL).

For synthesis of the single-stranded cDNA, 5 μg of total RNA was used in the case of the cell lines and 1 μg of total RNA in the case of the blood cells, and the resulting single-stranded cDNAs were used as templates for PCR after diluting with water 50- and 10-fold,respectively.

(b) Preparation of a Standard and an Internal Control for Quantitative PCR pBSK+iGnT13 and pBSK+iGnT13d obtained in items (1) and (2) above were linearized by cleavage with restriction enzymes to take the cDNA insert therefrom, and then used as a standard and an internal control for determination of the iGnT transcripts.

One microgram each of pBSK+iGnT13 and pBSK+iGnT13d were dissolved in 36 μl of Y-100 buffer, and 20 U each of Xho I and Bam HI were added thereto, followed by digestion reaction at 37° C. for 2 hours.

An aliquot (10 μl) of the reaction mixture was subjected to agarose gel electrophoresis to confirm complete cleavage, and the reaction mixture was used after stepwise dilution with water containing 1 μg/ml yeast transfer RNA.

As the standard for determination of the β-actin transcripts, a linear DNA was prepared by cleaving pUC119-ACT with restriction enzymes (Hind III and Asp 718) to take the cDNA insert [J. Biol. Chem., 269, 14730 (1994), Japanese Published Unexamined Patent Application No. 181759/94].

As the internal control for determination of the β-actin transcripts, a linear DNA was prepared by cleaving pUC119-ACTd with restriction enzymes (Hind III and Asp 718) to take the cDNA insert [J. Biol. Chem., 269, 14730 (1994), Japanese Published Unexamined Patent Application No. 181759/94].

(c) Determination of the iGnT Transcripts by Quantitative PCR Techniques

In the presence of 5 μg of the internal control (pBSK+iGnT13d cleaved with Xho I and Bam HI) prepared in item (b), PCR was conducted using single-stranded cDNAs derived from various cells and cell lines as templates, which were prepared in item (a).

As PCR primers, DNA (abbreviated hereinafter to C12-3) shown in SEQ ID NO:13 and DNA (abbreviated hereinafter to C12-4) shown in SEQ ID NO:14 were synthesized (these were also available from Sawaday Technology).

PCR was conducted using a kit (GeneAmp™ DNA Amplification Reagent Kit with AmpliTaq™ Recombinant Taq DNA Polymerase) available from Takara Shuzo Co., Ltd.

The reaction mixture was prepared according to instructions attached to the kit. In this preparation, dimethyl sulfoxide was added at a final concentration of 5%.

The reaction mixture (29 μl) containing all reagents except for Taq DNA polymerase was treated at 97° C. for 5 minutes using Perkin Elmer Cetus' DNA Thermal Cycler (distributed by Takara Shuzo Co., Ltd.) and then rapidly cooled on ice.

After rapid cooling, 1 μl of 6.7-fold diluted Taq DNA polymerase was added to the reaction mixture, and 27-cycle reaction each cycle consisting of reaction at 94° C. for 30 seconds, at 60° C. for 1 minute, and at 72° C. for 2 minutes was performed using Perkin Elmer Cetus' DNA Thermal Cycler (Takara Shuzo Co., Ltd.).

After 7 μl of the reaction mixture was subjected to agarose gel electrophoresis, the gel was stained with SYBR™ Green I (Molecular Probes Ltd.).

The profile of the amplified DNA fragment was analyzed by Fluor Imager SI (Molecular Dynamics) to examine the amount of the amplified DNA.

Furthermore, PCR was conducted similarly using the standard (pBSK+iGnT13 cleaved with Xho I and Bam HI) as a template in place of single-stranded cDNAs derived from various cells and cell lines was conducted to prepare a calibration curve.

The size of the DNA fragment derived from the iGnT transcripts and the standard was 615 bp and the size of the DNA fragment derived from the internal control was 416 bp, and the amount (number of moles) of the iGnT transcripts was calculated based on the ratio of the amount of both the DNA fragments. For more accurate determination of the transcript, each sample was subjected again to PCR using the internal control in an amount near to the amount of the transcript determined above. The number of cycles in PCR was varied depending on the amount of the internal control.

Determination of the β-actin transcripts was also conducted similarly using two-step PCR. The internal control used was pUC119-ACTd cleaved with Hind III and Asp 718 as described in (b) above, and the standard was pUC119-ACT cleaved with Hind III and Asp 718 as described in (b).

The PCR primers used were DNA shown in SEQ ID NO:15 (hereinafter abbreviated to Ac-1) and DNA shown in SEQ ID NO:16 (hereinafter abbreviated to Ac-3) which were synthesized in a 380A DNA synthesizer (Applied Biosystems).

The first PCR was conducted using 10 μg of the internal control for 17 cycles. In the case of β-actin, dimethyl sulfoxide was not added to the PCR reaction mixture.

The expressn level of the iGnT transcripts was finally determined as a relative value (%) with the amount of the β-actin transcripts being taken as 100.

The results are shown in Table 1.

It was revealed that the amount of the iGnT transcripts can be determined by the method described above.

TABLE 1

| Cells | Expression level (%) |
|---|---|
| Namalwa KJM-1 | 0.37 |
| WM266-4 | 0.76 |
| THP-1 | 0.03 |
| HL-60 | 0.12 |
| U-937 | 0.13 |
| Jurkat | 0.29 |
| Colo205 | 0.27 |
| SW1116 | 0.31 |
| LS180 | 0.72 |
| Polymorphonuclear leukocytes | 0.02 |
| Monocytes | 0.03 |
| Lymphocytes | 0.14 |

According to the present invention, there can be provided a polypeptide having poly-N-acetyllactosamine sugar chains synthesis-related activity, a process for producing the polypeptide, DNA coding for the polypeptide, a process for producing the DNA, a recombinant vector having the DNA integrated therein, a transformant carrying the recombinant vector, an antibody recognizing the polypeptide, a process for producing poly-N-acetyllactosamine sugar chains by use of the DNA or the polypeptide, diagnosis and treatment of diseases such as inflammations, cancers etc. by use of the DNA, the polypeptide or the antibody, determination and immunostaining of the polypeptide of the present invention by use of the antibody, a method for screening a compound varying the expression of a gene coding for the polypeptide, and a method for screening a substance varying the activity of the polypeptide.

What is claimed is:

1. An isolated DNA coding for a polypeptide having the amino acid sequence of SEQ ID NO: 1.

2. An isolated DNA which has a nucleotide sequence having 95% or more homology with the nucleotide sequence coding for a polypeptide having the amino acid sequence of SEQ ID NO: 1, and codes for a polypeptide having poly-N-acetyllactosamine sugar chains synthesis activity.

3. An isolated DNA, which hybridizes under a stringent condition to a DNA coding for a polypeptide having the amino acid sequence of SEQ ID NO: 1, and which codes for a polypeptide having poly-N-acetyllactosamine sugar chains synthesis activity, wherein the stringent condition comprises hybridization at 65° in the presence of 0.7 to 1.0 M NaCl and washing at 65° C. with a 0.1 to 2×SSC solution.

4. An isolated DNA according to any of claims 1-3 wherein the DNA comprises nucleotides 80 to 1324 of SEQ ID NO:2.

5. A recombinant DNA prepared by integrating the DNA according to claims 1-3 into a vector.

6. A recombinant DNA prepared by integrating the DNA according to claim 4 into a vector.

7. A recombinant DNA according to claim 5 wherein the recombinant DNA is plasmid pVL1393-i.

8. A recombinant DNA according to claim 6 wherein the recombinant DNA is plasmid pVL1393-i.

9. A process for isolating the DNA according to claims 1-3, which comprises inserting a cDNA synthesized using an mRNA extracted from an animal cell as a template into an expression cloning vector to construct a cDNA library, introducing the cDNA library into cells, screening the resulting cells to select those reacting with an antibody (anti-i antibody) against poly-N-acetyllactosamine sugar chains, and recovering, from the selected cells, a DNA coding for a polypeptide having poly-N-acetyllactosamine sugar chains synthesis activity.

10. A process for isolating the DNA according to claim 4, which comprises inserting a cDNA synthesized using an mRNA extracted from an animal cell as a template into an expression cloning vector to construct a cDNA library, introducing the cDNA library into cells, screening the resulting cells to select those reacting with an antibody (anti-i antibody) against poly-N-acetyllactosamine sugar chains, and recovering, from the selected cells, a DNA coding for a polypeptide having poly-N-acetyllactosamine sugar chains synthesis activity.

11. A method for determining expression level of a gene comprising DNA according to claims 1-3, comprising the steps of assaying the amount of a transcript of the gene using said DNA.

12. A method for determining expression level of a gene comprising DNA according to claims 1-3, comprising the steps of assaying the amount of a transcript of the gene using a DNA comprising nucleotides 80 to 1324 of SEQ ID NO:2.

13. A method for determining expression level of a gene comprising a DNA according to claims 1-3, comprising the steps of assaying the amount of a transcript of the gene using a DNA comprising at least 10 consecutive nucleotides in any single DNA selected from the group consisting of (i) said DNA according to claims 1-3, (ii) the nucleotide sequence of SEQ ID NO:2 and (iii) a DNA having a sequence complementary to the sequence of said (i) or (ii).

14. A method for determining expression level of a gene comprising a DNA according to claims 1-3, comprising the steps of assaying the amount of a transcript of the gene using a derivative of a DNA comprising at least 10 consecutive nucleotides in any single DNA selected from the group consisting of (i) said DNA according to claims 1-3, (ii) the nucleotide sequence of SEQ ID NO:2 and (iii) a DNA having a nucleotide sequence complementary to the sequence of said (i) or (ii), wherein the derivative is selected from the group consisting of DNA in which the diphosphate bond has been converted into a phosphorothioate bond, DNA in which the diphosphate bond has been converted into an N3'-P5' phosphoamidate bond, DNA in which the ribose and the diphosphate bond have been converted into a peptide-nucleic acid bond, DNA in which the uracil has been substituted with a C-5 propynyluracil, DNA in which the uracil has been substituted with a C-5 thiazolyluracil, DNA in which the cytosine has been substituted with a C-5 propynylcytosine, DNA in which the cytosine has been substituted with a phenoxazine-modified cytosine, DNA in which the ribose has been substituted with a 2'O-propylribose, and DNA in which the ribose has been substituted with a 2'-methoxyethoxyribose.

15. A method for detecting inflammations or cancers, comprising:

determining the expression level of a transcript of a gene comprising a DNA according to claims 1-3 using a DNA comprising at least 10 consecutive nucleotides in any single DNA selected from the group consisting of (i) said DNA according to claims 1-3, (ii) the nucleotide sequence of SEQ ID NO:2 and (iii) a DNA having a sequence complementary to the sequence of said (i) or (ii); and correlating said expression level with said inflammation or cancer.

16. A method for detecting inflammations or cancers according to claim 15, wherein the DNA is selected from the group consisting of DNA in which the diphosphate bond has been converted into a phosphorothioate bond, DNA in which the diphosphate bond has been converted into an N3'-P5'-phosphoamidate bond, DNA in which the ribose and the diphosphate bond have been converted into a peptide-nucleic acid bond, DNA in which the uracil has been substituted with a C-5 propynyluracil, DNA in which the uracil has been substituted with a C-5 thiazolyluracil, DNA in which the cytosine has been substituted with a C-5 propynylcytosine, DNA in which the cytosine has been substituted with a phenoxazine-modified cytosine, DNA in which the ribose has been substituted with a 2'-O-propylribose, and DNA in which the ribose has been substituted with a 2'-methoxyethoxyribose.

17. A method of inhibiting in vivo transcription of DNA coding for a polypeptide having poly-N-acetyllactosamine sugar chains synthesis activity, or translation of corresponding mRNA, comprising the steps of administering DNA that is anti-sense to the DNA of claims 1-3.

18. A method of inhibiting in vivo transcription of DNA coding for a polypeptide having poly-N-acetyllactosamine sugar chains synthesis activity, or translation of corresponding mRNA, comprising the steps of administering DNA that is anti-sense to the DNA according to claim 4.

19. A method of inhibiting in vivo transcription of DNA coding for a polypeptide having poly-N-acetyllactosamine sugar chains synthesis activity, or translation of corresponding mRNA, comprising the steps of administering a DNA comprising at least 10 consecutive nucleotides in any single DNA selected from the group consisting of (i) said DNAs of claims 1-3, (ii) the nucleotide sequence of SEQ ID NO:2 and (iii) a DNA having a sequence complementary to the sequence of said (i) or (ii).

20. A method of inhibiting in vivo transcription of DNA coding for a polypeptide having poly-N-acetyllactosamine sugar chains synthesis activity, or translation of corresponding mRNA, comprising the steps of administering a derivative of DNA comprising at least 10 consecutive nucleotides in any single DNA selected from the group consisting of (i) the DNAs of claims 1-3, (ii) the nucleotide sequence of SEQ ID NO:2 and (iii) a DNA having a sequence complementary to the sequence of said (i) or (ii), wherein the derivative is selected from the group consisting of DNA in which the diphosphate bond has been converted into a phosphorothioate bond, DNA in which the diphosphate bond has been converted into N3'-P5' phosphoamidate bond, DNA in which the ribose and the diphosphate bond have been converted into a peptide-nucleic acid bond, DNA in which the uracil has been substituted with a C-5 propynyluracil, DNA in which the uracil has been substituted with a C-5 thiazolyluracil, DNA in which the cytosine has been substituted with a C-5 propynylcytosine, DNA in which the cytosine has been substituted with a phenoxazine-modified cytosine, DNA in which the ribose has been substituted with a 2'-O-propylribose, and DNA in which the ribose has been substituted with a 2'-methoxyethoxyribose.

21. A non-human transformant transformed with the recombinant DNA according to claim 6.

22. A transformant according to claim 21, wherein the transformant is a microorganism belonging to the genus *Eseherichia*.

23. A transformant according to claim 21, wherein the transformant is an animal cell or an insect cell.

* * * * *